(12) United States Patent
Furusako et al.

(10) Patent No.: US 6,251,873 B1
(45) Date of Patent: Jun. 26, 2001

(54) ANTISENSE COMPOUNDS TO CD14

(75) Inventors: Shoji Furusako; Yoshifumi Horisawa; Takeshi Kusuyama, all of Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/180,437

(22) PCT Filed: Mar. 9, 1998

(86) PCT No.: PCT/JP98/00953

§ 371 Date: Nov. 6, 1998

§ 102(e) Date: Nov. 6, 1998

(87) PCT Pub. No.: WO98/39438

PCT Pub. Date: Sep. 11, 1998

(30) Foreign Application Priority Data

Mar. 7, 1997 (JP) .................................................. 9-053578

(51) Int. Cl.[7] .............................. A61K 48/00; C12Q 1/68; C07H 21/04
(52) U.S. Cl. ................................. 514/44; 435/6; 536/23.1; 536/24.3; 536/24.5
(58) Field of Search ............................... 536/23.1, 24.31, 536/24.5; 514/44; 435/6

(56) References Cited

U.S. PATENT DOCUMENTS

| | | | |
|---|---|---|---|
| 5,543,303 | 8/1996 | Goyert | 435/69.1 |
| 5,585,479 | * 12/1996 | Hoke et al. | 536/24.5 |

FOREIGN PATENT DOCUMENTS

| | | |
|---|---|---|
| 9620957 | 7/1996 | (WO) . |
| 9319772 | 10/1998 | (WO) . |

OTHER PUBLICATIONS

Stein, Hybridization gets to first base, Nature Biotechnology, vol. 17, pp. 751–752, Aug. 1999.*

Sanghvi, Heterocyclic base modifications in nucleic acids and their applications in antisense oligonucleotides, Antisense Research and Applications, chapter 15, pp. 273–288, 1993.*

James, Towards gene–inhibition therapy,: a review of progress and prospects in the field of antiviral antisense nucleic acids and ribozymes, Antiviral Chemistry and Chemotherapy, vol. 2 (4), pp. 191–214, 1991.*

NEB Catalog, pp. 60–62, 1986/1987.*

Rojanasakul, Antisense oligonucleotide therapeutics: Drug delivery and targeting, Advanced Drug Delivery Reviews, vol. 18, pp. 115–131, 1996.*

Gewirtz et al., Facilitating oligonucleotide delivery: Helping antisense deliver on its promise, PNAS, vol. 93, pp. 3161–3163, Apr. 1996.*

Branch, A good antisense is hard to find, TIBS, vol. 23, pp. 45–50, 1988.*

E Ferro et al., *Nucleic Acids Research*, vol. 16, No. 9, p. 4173 (1988).

M. Setoguchi et al., *Cell Mol. Genet.*, vol. 14, No. 5, pp. 427–438 (1995).

S. D. Wright et al., *Science*, vol. 249, pp. 1431–1433 (1990).

D. Gupta et al., *J. Biol. Chem.*, vol. 271, No. 38, pp. 23310–23316 (1996).

J. Pugin et al., *Immunity*, vol. 1, pp. 509–516 (1994).

P. Bufler et al., *Eur. J. Immunol.*, vol. 25, pp. 604–610 (1995).

M. M. Wurfel et al., *J. Exp. Med.*, vol. 181, pp. 1743–1754 (1995).

S. Yoko et al., *Gan to Kagakuryoho*, vol. 20, pp. 1899–1907 (1993) (Abstract attached).

R. O. Dempcy et al., *Proc. Natl. Acad. Sci., USA*, vol. 92, pp. 6097–6101 (1995).

J. Bertrand, Jr. et al., *Biochem. Biophys. Res. Comm.*, vol. 164, No. 1 pp. 311–318 (1989).

G. Degols et al., *Nucleic Acids Research*, vol. 17, No. 22, pp. 9341–9350 (1989).

A. W. McConnaughie et al., *J. Med. Chem.*, vol. 38, pp. 3488–3501 (1995).

G. Godard et al., *Eur. J. Biochem.*, vol. 232, pp. 404–410 (1995).

A. A. Padmapriya et al., *Antisense Research and Development*, vol. 4, pp. 185–199 (1994).

R. L. Delude et al., *Proc. Natl. Acad. Sci., USA*, vol. 92, pp. 9288–9292 (1995).

* cited by examiner

*Primary Examiner*—Andrew Wang
(74) *Attorney, Agent, or Firm*—Birch, Stewart Kolasch & Birch, LLP

(57) ABSTRACT

The present invention relates to an oligonucleotide and derivatives, hybridizable with or being complementary to at least a part of a gene encoding human CD14; and to pharmaceutical compositions, comprising the oligonucleotide or derivatives thereof as effective ingredient; and is utilisable of cure of systemic inflammatory response sydorome, etc., by the use of the pharmaceutical composition.

20 Claims, 12 Drawing Sheets

Effect of SM0105A on GPT activity in endotoxin shock model

FIG. 10

```
5'                                                                          3'
     103                                                              137
human   A CUU AUC GAC CAU GGA GCG CGC GUC CUG CUU GUU G
mouse   A UCU ACC GAC CAU GGA GCG UGU GCU UGG CUU GUU G
```

Sequence of consensus oligonucleotide

```
3'                                                                          5'
     103                                                              137
     T XXA TXG CTG GTA CCT CGC XCX CXX XXC GAA CAA C
```

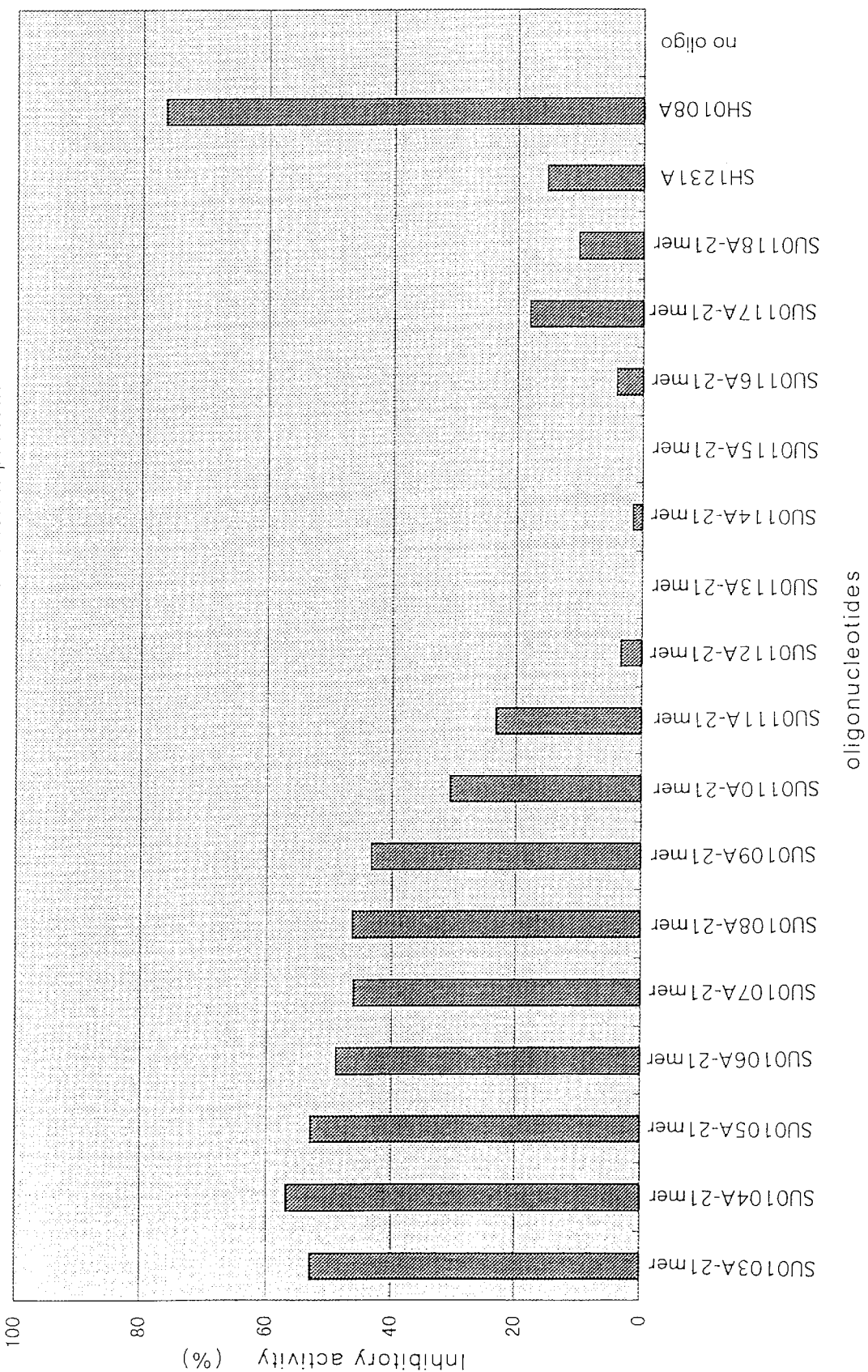

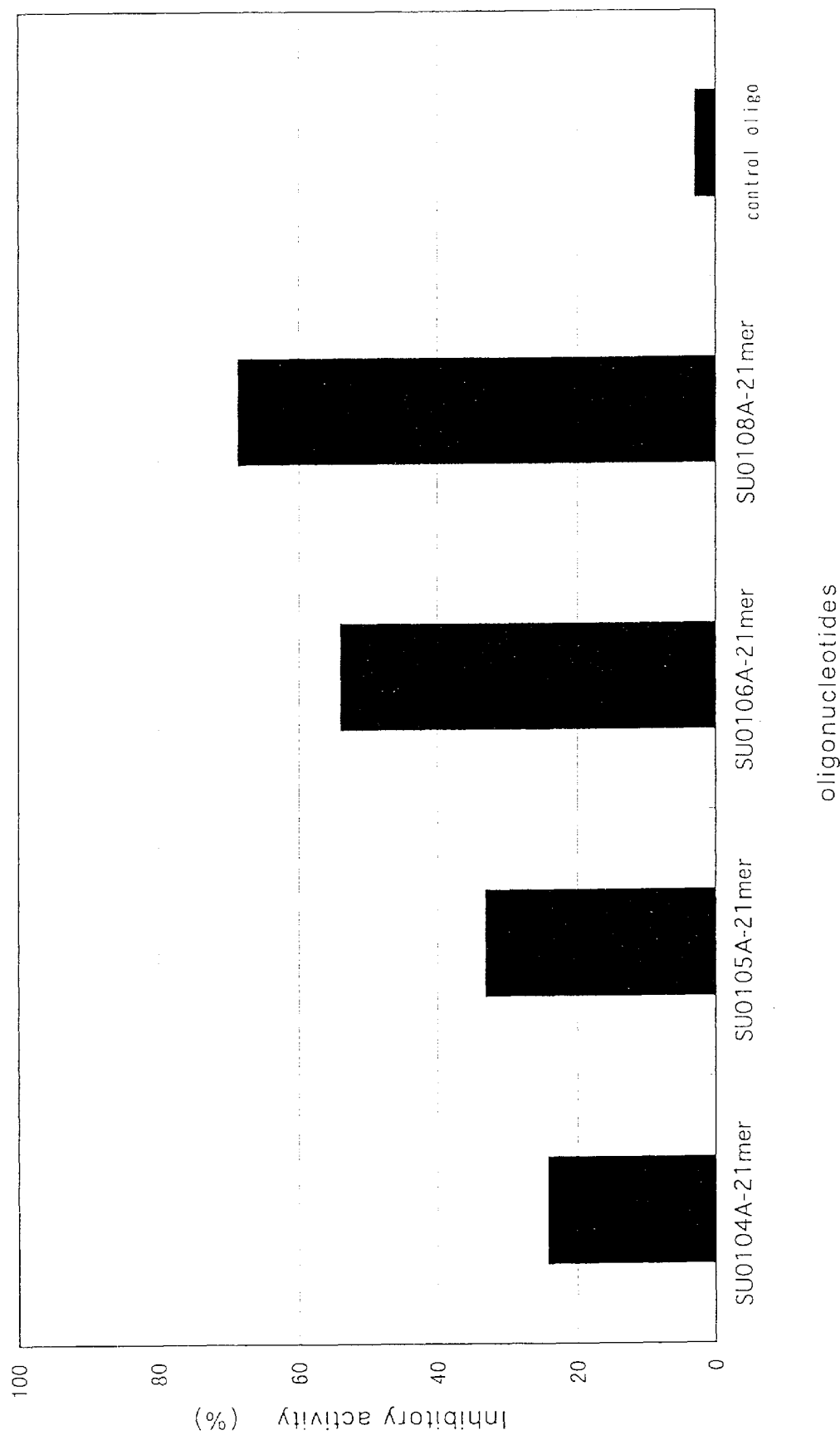

SEQUENCE LISTING

<160> NUMBER OF SEQ ID NOS: 289

<210> SEQ ID NO: 1
<211> LENGTH: 1351
<212> TYPE: DNA
<213> ORGANISM: Homo sapiens

<400> SEQUENCE: 1

| gaagaguuca | caagugugaa | gccuggaagc | cgccggguge | cgcuguguag | gaaagaagcu | 60 |
| aaagcacuuc | cagagccugu | ccggagcuca | gagguucgga | agacuuaucg | accauggagc | 120 |
| gcgcguccug | cuuguugcug | cugcugcugc | cgcuggugca | cgucucugcg | accacgccag | 180 |
| aaccuuguga | gcuggacgau | gaagauuucc | gcugcgucug | caacuucucc | gaaccucagc | 240 |
| ccgacgguc | cgaagccuuc | cagugugugu | cugcaguaga | gguggagauc | caugccggcg | 300 |
| gucucaaccu | agagccguuu | cuaaagcgcg | ucgaugcgga | cgccgacccg | cggcaguaug | 360 |
| cugacacggu | caaggcucuc | cgcgugcggc | ggcucacagu | gggagccgca | cagguuccug | 420 |
| cucagcuacu | gguaggcgcc | cugcgugugc | uagcguacuc | ccgccucaag | gaacugacgc | 480 |
| ucgaggaccu | aaagauaacc | ggcaccaugc | cuccgcugcc | ucuggaagcc | acaggacuug | 540 |
| cacuuccag | cuugcgccua | cgcaacgugu | cgugggcgac | agggcguucu | uggcucgccg | 600 |
| agcugcagca | guggcucaag | ccaggccuca | agguacugag | cauugcccaa | gcacacucgc | 660 |
| cugccuuuuc | cuacgaacag | guucgcgccu | ucccggcccu | uaccagccua | gaccugucug | 720 |
| acaauccugg | acugggcgaa | cgcggacuga | uggcggcucu | cuguccccac | aaguucccgg | 780 |
| ccauccagaa | ucuagcgcug | cgcaacacag | gaauggagac | gcccacaggc | gugugcgccg | 840 |
| cacuggcggc | ggcaggugug | cagccccaca | gccuagaccu | cagccacaac | ucgcugcgcg | 900 |
| ccaccguaaa | cccuagcgcu | ccgagaugca | uguggugccag | cgcccugaac | ucccucaauc | 960 |
| ugucguucgc | ugggcuggaa | caggugccua | aggacugcc | agccaagcuc | agagugcucg | 1020 |
| aucucagcug | caacagacug | aacagggcgc | cgcagccuga | cgagcugccc | gagguggaua | 1080 |
| accugacacu | ggacgggaau | cccuuccugg | ucccuggaac | ugcccucccc | cacgagggcu | 1140 |
| caaugaacuc | cggcguggnc | ccagccugug | cacguucgac | ccugucggug | ggggugucgg | 1200 |
| gaacccuggu | gcugcuccaa | ggggcccggg | gcuuugccua | agauccaaga | cagaauaaug | 1260 |
| aauggacuca | aacugccuug | gcuucagggg | agucccguca | ggacguugag | gacuuuucga | 1320 |
| ccaauucaac | ccuuugcccc | accuuuauua | a | | | 1351 |

<210> SEQ ID NO: 2
<211> LENGTH: 1570
<212> TYPE: DNA
<213> ORGANISM: Homo sapiens

<400> SEQUENCE: 2

| cagaatgaca | tcccaggatt | acataaactg | tcagaggcag | ccgaagagtt | cacaagtgtg | 60 |
| aagcctggaa | gccgccgggt | gccgctgtgt | aggaaagaag | ctaaagcact | tccagagcct | 120 |
| gtccggagct | cagaggttcg | gaagacttat | cgaccatggt | gagtgtaggg | tcttggggtc | 180 |
| gaacgcgtgc | cactcgggag | ccacagggt | tggatggggc | ctcctagacc | tctgctctct | 240 |
| ccccaggagc | gcgcgtcctg | cttgttgctg | ctgctgctgc | cgctggtgca | cgtctctgcg | 300 |
| accacgccag | aaccttgtga | gctggacgat | gaagatttcc | gctgcgtctg | caacttctcc | 360 |
| gaacctcagc | ccgactggtc | cgaagccttc | cagtgtgtgt | ctgcagtaga | ggtggagatc | 420 |

```
catgccggcg gtctcaacct agagccgttt ctaaagcgcg tcgatgcgga cgccgacccg    480
cggcagtatg ctgacacggt caaggctctc cgcgtgcggc ggctcacagt gggagccgca    540
caggttcctg ctcagctact ggtaggcgcc ctgcgtgtgc tagcgtactc ccgcctcaag    600
gaactgacgc tcgaggacct aaagataacc ggcaccatgc ctccgctgcc tctggaagcc    660
acaggacttg cactttccag cttgcgccta cgcaacgtgt cgtgggcgac agggcgttct    720
tggctcgccg agctgcagca gtggctcaag ccaggcctca aggtactgag cattgcccaa    780
gcacactcgc ctgccttttc ctacgaacag gttcgcgcct cccggccct taccagccta    840 gacctgtctg acaatcctgg actgggcgaa cgcggactga tggcggctct ctgtccccac    900
aagttcccgg ccatccagaa tctagcgctg cgcaacacag gaatggagac gcccacaggc    960
gtgtgcgccg cactggcggc ggcaggtgtg cagccccaca gcctagacct cagccacaac   1020
tcgctgcgcg ccaccgtaaa ccctagcgct ccgagatgca tgtggtccag cgccctgaac   1080
tccctcaatc tgtcgttcgc tgggctggaa caggtgccta aggactgcc agccaagctc   1140 agagtgctcg atctcagctg caacagactg aacaggcgc cgcagcctga cgagctgccc   1200
gaggtggata acctgacact ggacgggaat cccttcctgg tccctggaac tgccctcccc   1260
cacgagggct caatgaactc cggcgtggtc ccagcctgtg cacgttcgac cctgtcggtg   1320
ggggtgtcgg gaaccctggt gctgctccaa ggggcccggg gctttgccta agatccaaga   1380
cagaataatg aatggactca aactgccttg gcttcagggg agtcccgtca ggacgttgag   1440
gacttttcga ccaattcaac cctttgcccc acctttatta aatcttaaa caacggttcc   1500 gtgtcattca tttaacagac ctttattgga tgtctgctat gtgctgggca cagtactgga   1560
tggggaattc                                                          1570

<210> SEQ ID NO: 3
<211> LENGTH: 1447
<212> TYPE: DNA
<213> ORGANISM: Mus sp.

<400> SEQUENCE: 3
cgaacaagcc cguggaaccu ggaagccaga gaacaccacc gcuguaaagg aaagaaacug     60
aagccuuucu cggagccuau cugggcugcu caaacuuuca gaaucuaccg accauggagc    120
gugugcuugg cuuguugcug uugcuucugg ugcacgccuc uccgccccca ccagagcccu    180
gcgagcuaga cgaggaaagu uguuccugca acuucucaga uccgaagcca gauuggucca    240
gcgcuuucaa uuguuggggg cggcagaug uggaauugua cggcggcggc cgcagccugg    300
aauaccuucu aaaagcgugug gacacggaag cagaucuggg gcaguucacu gauauuauca    360
agucucuguc cuuaaagcgg cuuacggugc gggccgcgcg gauuccuagu cggauucuau    420
ucggagcccu gcgugugcuc gggauuuccg gccuccagga acugacucuu gaaaaucucg    480
agguaaccgg caccgcgccg ccaccgcuuc uggaagccac cggacccgau cucaacaucu    540
ugaaccuccg caacgugucg ugggcaacaa gggaugccug gcucgcagaa cugcagcagu    600
ggcuaaagcc uggacucaag guacugagua uugcccaagc acacucacuc aacuuuuccu    660
gcgaacaggu ccgcgucuuc ccugcccucu ccaccuuaga ccugcugac aauccugaau    720 ugggcgagag aggacugauc ucagcccucu gucccucaa guucccgacc cuccaaguuu    780
uagcgcugcu uaacgcgggg augggagacg ccagcggcgu gugcucugcg cuggccgcag    840 caagggguaca gcugcaagga cuagaccuua gucacaauuc acugcgggau gcugcaggcg    900
```

-continued

| | |
|---|---|
| cuccgaguug ugacuggccc agucagcuaa acucgcucaa ucugucuuuc acugggcuga | 960 |
| agcagguacc uaaagggcug ccagccaagc ucagcgugcu ggaucucagu acaacaggc | 1020 |
| uggauaggaa cccuagccca gaugagcugc cccaaguggg gaaccuguca cuuaaaggaa | 1080 |
| aucccuuuuu ggacucugaa ucccacucgg agaaguuuaa cucggcgua gucaccgccg | 1140 |
| gagcuccauc aucccaagca guggccuugu caggaacucu ggcuuugcuc cuaggagauc | 1200 |
| gccucuuugu uuaaggaaca uuugcauccu ccugguuucu gagggccuc gucaacgaau | 1260 |
| ccucugcuuu aaauuuauua aaaucuuaau ccacgaugua aggaaagaaa ggcagucaag | 1320 |
| augguucagu ggguaaaagc cagcaaacuu gaccccugau uuuaacccuc aggauccaca | 1380 |
| cggaagggga aaacucacuc cugaaaguug uccaucugug cucacaaaua aauauuuuuu | 1440 |
| aaaauaa | 1447 |

<210> SEQ ID NO: 4
<211> LENGTH: 2404
<212> TYPE: DNA
<213> ORGANISM: Mus sp.

<400> SEQUENCE: 4

| | |
|---|---|
| cctagcattt gggaggcaga ggcaggagga aaatcatgcg tttcaggcta ggctagattg | 60 |
| ggttactaga ctgagatatc atgggagaa tggagaggta gagagtggga gaagaatgaa | 120 |
| ttaataaaga actgaataag atgggaagaa gggagaatta tttttcatat taactctcaa | 180 |
| ctttgagctt tattctctgc ctggaatcta tagataagtt cacaatcttt ccacaaatgt | 240 |
| ccaattacat tcaaagaaaa tcaagagctg gatttgaacg gtgggaaatt gctagcaact | 300 |
| aagactaggg gaaatggagg tgaatcaatg ggactgagca acagaataat gatctaaggc | 360 |
| actaggtgtg attcactctt ttcctgtacg caccagacaa gtccggggct cataggtcat | 420 |
| cctcctggca cagaatgccc taatgccact ctgaattctt cctgttttc gtccctccct | 480 |
| aaaaaacact tccttgcaat atttactaga agtgagtagg gctgttagga ggaagagaag | 540 |
| tggagacgca attagaattc acagaggaag ggacagggtg acaccccagg attacataaa | 600 |
| tttacagggg ctgccgaatt ggtcgaacaa gcccgtggaa cctggaagcc agagaacacc | 660 |
| atcgctgtaa aggaaagaaa ctgaagcttt tctcggagcc tatctgggct gctcaaactt | 720 |
| tcagaatcta ccgaccatgg tgagtcagac agactgtctt ggggtggaac tggagccaac | 780 |
| ctgaggaatc tcagggtctg gcaggagtct ccctgacccc tactttctcc tcaggagcgt | 840 |
| gtgcttggct tgttgctgtt gcttctggtg cacgcctctc ccgcccacc agagccctgc | 900 |
| gagctagaca aggaaagttg ttcctgcaac ttctcagatc cgaagccaga ttggtccagc | 960 |
| gctttcaatt gtttggggc ggcagatgtg gaattgtacg gcggcggccg cagcctggaa | 1020 |
| taccttctaa agcgtgtgga cacggaagca gatctgggc agttcactga tattatcaag | 1080 |
| tctctgtcct taaagcggct tacggtgcgg gccgcgcgga ttcctagtcg gattctattc | 1140 |
| ggagccctgc gtgtgctcgg gatttccggc tccaggaac tgactcttga aaatctcgag | 1200 |
| gtaaccggca ccgcgccgcc accgcttctg gaagccaccg gacccgatct caacatcttg | 1260 |
| aacctccgca acgtgtcgtg ggcaacaagg gatgcctggc tcgcagaact gcagcagtgg | 1320 |
| ctaaagcctg gactcaaggt actgagtatt gcccaagcac actcactcaa cttttcctgc | 1380 |
| gaacaggtcc gcgtcttccc tgccctctcc accttagacc tgtctgacaa tcctgaattg | 1440 |
| ggcgagagag gactgatctc agccctctgt ccctcaagt tcccgaccct caagttttta | 1500 |
| gcgctgcgta acgcggggat ggagacgccc agcggcgtgt gctctgcgct ggccgcagca | 1560 |

```
aggglacagc tgcaaggact agaccttagt cacaattcac tgcgggatgc tgcaggcgct    1620
ccgagttgtg actggcccag tcagctaaac tcgctcaatc tgtctttcac tgggctgaag    1680
caggtaccta aagggctgcc agccaagctc agcgtgctgg atctcagtta caacaggctg    1740
gataggaacc ctagcccaga tgagctgccc caagtgggga acctgtcact taaggaaat     1800 cccttttgg actctgaatc ccactcggag aagtttaact ctggcgtagt caccgccgga     1860
gctccatcat cccaagcagt ggccttgtca ggaactctgg ctttgctcct aggagatcgc    1920
ctctttgttt aaggaacatt tgcatcctcc tggtttctga gggtcctcgt caacgaatcc    1980
tctgctttaa atttattaaa atcttaatcc acgatgtaag gaaagaaagg cagtcaagat    2040
ggttcagtgg gtaaaagcca gcaaacttga cccctgattt taaccctcag gatccacacg    2100 gaagggaaa actcactcct gaaagttgtc catctgtgct cacaaataaa tattttttaa     2160
aataacaatg tgtttgttgg ttttgttttt gtttgggttt tgttgtggtt ttgtttgttt    2220
tgttttgttt ttgagacagt ctggctatgt atccttggct ggcctcaaac tcataaagat    2280
caagatcggc ctgcctctac ctccaaatgc tctggttaaa gggatgtgcc tccatgccca    2340
gttgaagtca tcctgaacca cgagtccagg ccactcactc tttactaaga tctttactaa    2400
gtat                                                                 2404

<210> SEQ ID NO: 5
<211> LENGTH: 32
<212> TYPE: DNA
<213> ORGANISM: Artificial Sequence
<220> FEATURE:
<223> OTHER INFORMATION: Description of Artificial Sequence: sense
      primer

<400> SEQUENCE: 5
acgcgtcgac gagttcacaa gtgtgaagcc tg                              32

<210> SEQ ID NO: 6
<211> LENGTH: 32
<212> TYPE: DNA
<213> ORGANISM: Artificial Sequence
<220> FEATURE:
<223> OTHER INFORMATION: Description of Artificial Sequence: antisense
      primer

<400> SEQUENCE: 6
acatgcatgc ttaataaagg tggggcaaag gg                              32

<210> SEQ ID NO: 7
<211> LENGTH: 33
<212> TYPE: DNA
<213> ORGANISM: Artificial Sequence
<220> FEATURE:
<223> OTHER INFORMATION: Description of Artificial Sequence: sense
      primer

<400> SEQUENCE: 7
cccaagctta agtgtgaagc ctgaagccgc cgg                             33

<210> SEQ ID NO: 8
<211> LENGTH: 44
<212> TYPE: DNA
<213> ORGANISM: Artificial Sequence
<220> FEATURE:
<223> OTHER INFORMATION: Description of Artificial Sequence: antisense
      primer
```

<400> SEQUENCE: 8
atggcgccgg gcctttcttt atgtttttgg cgtcttccag ttgg             44

<210> SEQ ID NO: 9
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 9
cggcttccag gcttcacact                                        20

<210> SEQ ID NO: 10
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 10
cggcacccgg cggcttccag                                        20

<210> SEQ ID NO: 11
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 11
tcctacacag cggcacccgg                                        20

<210> SEQ ID NO: 12
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 12
ttctttccta cacagcggca                                        20

<210> SEQ ID NO: 13
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 13
ttagcttctt tcctacacag                                        20

<210> SEQ ID NO: 14
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 14

```
gtgctttagc ttctttccta                                              20

<210> SEQ ID NO: 15
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 15
tggaagtgct ttagcttctt                                              20

<210> SEQ ID NO: 16
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 16
ggacaggctc tggaagtgct                                              20

<210> SEQ ID NO: 17
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 17
tctgagctcc ggacaggctc                                              20

<210> SEQ ID NO: 18
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 18
cttccgaacc tctgagctcc                                              20

<210> SEQ ID NO: 19
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 19
gtcgataagt cttccgaacc                                              20

<210> SEQ ID NO: 20
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 20
```

```
atggtcgata agtcttccga                                              20

<210> SEQ ID NO: 21
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 21
tccatggtcg ataagtcttc                                              20

<210> SEQ ID NO: 22
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 22
cgctccatgg tcgataagtc                                              20

<210> SEQ ID NO: 23
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 23
cgcgctccat ggtcgataag                                              20

<210> SEQ ID NO: 24
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 24
gcgcgctcca tggtcgataa                                              20

<210> SEQ ID NO: 25
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 25
cgcgcgctcc atggtcgata                                              20

<210> SEQ ID NO: 26
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 26
acgcgcgctc catggtcgat                                              20
```

<210> SEQ ID NO: 27
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 27
gacgcgcgct ccatggtcga                                          20

<210> SEQ ID NO: 28
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 28
ggacgcgcgc tccatggtcg                                          20

<210> SEQ ID NO: 29
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 29
gcaggacgcg cgctccatgg                                          20

<210> SEQ ID NO: 30
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 30
aagcaggacg cgcgctccat                                          20

<210> SEQ ID NO: 31
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 31
acaagcagga cgcgcgctcc                                          20

<210> SEQ ID NO: 32
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 32
aacaagcagg acgcgcgctc                                          20

```
<210> SEQ ID NO: 33
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 33
caacaagcag gacgcgcgct                                              20

<210> SEQ ID NO: 34
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 34
agcaacaagc aggacgcgcg                                              20

<210> SEQ ID NO: 35
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 35
gcagcaacaa gcaggacgcg                                              20

<210> SEQ ID NO: 36
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 36
cagcagcaac aagcaggacg                                              20

<210> SEQ ID NO: 37
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 37
agcagcagca acaagcagga                                              20

<210> SEQ ID NO: 38
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 38
tcttggatct taggcaaagc                                              20
```

<210> SEQ ID NO: 39
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 39
cattattctg tcttggatct                                              20

<210> SEQ ID NO: 40
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 40
cagtttgagt ccattcatta                                              20

<210> SEQ ID NO: 41
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 41
aggcagtttg agtccattca                                              20

<210> SEQ ID NO: 42
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 42
caaggcagtt tgagtccatt                                              20

<210> SEQ ID NO: 43
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 43
ccaaggcagt ttgagtccat                                              20

<210> SEQ ID NO: 44
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 44
gccaaggcag tttgagtcca                                              20

<210> SEQ ID NO: 45

```
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 45
agccaaggca gtttgagtcc                                                  20

<210> SEQ ID NO: 46
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 46
aagccaaggc agtttgagtc                                                  20

<210> SEQ ID NO: 47
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 47
gaagccaagg cagtttgagt                                                  20

<210> SEQ ID NO: 48
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 48
tgaagccaag gcagtttgag                                                  20

<210> SEQ ID NO: 49
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 49
ctgaagccaa ggcagtttga                                                  20

<210> SEQ ID NO: 50
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 50
cctgaagcca aggcagtttg                                                  20

<210> SEQ ID NO: 51
<211> LENGTH: 20
```

```
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 51
ccctgaagcc aaggcagttt                                              20

<210> SEQ ID NO: 52
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 52
ccctgaagcc aaggcagttt                                              20

<210> SEQ ID NO: 53
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 53
ctcccctgaa gccaaggcag                                              20

<210> SEQ ID NO: 54
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 54
ggactcccct gaagccaagg                                              20

<210> SEQ ID NO: 55
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 55
tgacgggact ccctgaagc                                               20

<210> SEQ ID NO: 56
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 56
ctcaacgtcc tgacgggact                                              20

<210> SEQ ID NO: 57
<211> LENGTH: 20
<212> TYPE: DNA
```

```
<213> ORGANISM: Artificial Sequence
<220> FEATURE:
<223> OTHER INFORMATION: Description of Artificial Sequence: other
      nucleic acid, synthetic DNA

<400> SEQUENCE: 57
tcgaaaagtc ctcaacgtcc                                                 20

<210> SEQ ID NO: 58
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 58
gttgaattgg tcgaaaagtc                                                 20

<210> SEQ ID NO: 59
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 59
taataaaggt ggggcaaagg                                                 20

<210> SEQ ID NO: 60
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 60
cggcttccag gcttcacact                                                 20

<210> SEQ ID NO: 61
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 61
cggcacccgg cggcttccag                                                 20

<210> SEQ ID NO: 62
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 62
tcctacacag cggcacccgg                                                 20

<210> SEQ ID NO: 63
<211> LENGTH: 20
<212> TYPE: DNA
<213> ORGANISM: Artificial Sequence
```

```
<220> FEATURE:
<223> OTHER INFORMATION: Description of Artificial Sequence: other
      nucleic acid, synthetic DNA

<400> SEQUENCE: 63
ttagcttctt tcctacacag                                                    20

<210> SEQ ID NO: 64
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 64
tggaagtgct ttagcttctt                                                    20

<210> SEQ ID NO: 65
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 65
ggacaggctc tggaagtgct                                                    20

<210> SEQ ID NO: 66
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 66
tctgagctcc ggacaggctc                                                    20

<210> SEQ ID NO: 67
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 67
cttccgaacc tctgagctcc                                                    20

<210> SEQ ID NO: 68
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 68
gtcgataagt cttccgaacc                                                    20

<210> SEQ ID NO: 69
<211> LENGTH: 20
<212> TYPE: DNA
<213> ORGANISM: Artificial Sequence
<220> FEATURE:
```

<223> OTHER INFORMATION: Description of Artificial Sequence: other
      nucleic acid, synthetic DNA

<400> SEQUENCE: 69
atggtcgata agtcttccga                                              20

<210> SEQ ID NO: 70
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 70
tccatggtcg ataagtcttc                                              20

<210> SEQ ID NO: 71
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 71
cgctccatgg tcgataagtc                                              20

<210> SEQ ID NO: 72
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 72
gcgctccatg gtcgataagt                                              20

<210> SEQ ID NO: 73
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 73
cgcgctccat ggtcgataag                                              20

<210> SEQ ID NO: 74
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 74
gcgcgctcca tggtcgataa                                              20

<210> SEQ ID NO: 75
<211> LENGTH: 20
<212> TYPE: DNA
<213> ORGANISM: Artificial Sequence
<220> FEATURE:
<223> OTHER INFORMATION: Description of Artificial Sequence: other nucleic acid, synthetic DNA

<400> SEQUENCE: 75
cgcgcgctcc atggtcgata                                           20

<210> SEQ ID NO: 76
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 76
acgcgcgctc catggtcgat                                           20

<210> SEQ ID NO: 77
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 77
gacgcgcgct ccatggtcga                                           20

<210> SEQ ID NO: 78
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 78
ggacgcgcgc tccatggtcg                                           20

<210> SEQ ID NO: 79
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 79
aggacgcgcg ctccatggtc                                           20

<210> SEQ ID NO: 80
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 80
caggacgcgc gctccatggt                                           20

<210> SEQ ID NO: 81
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 81
gcaggacgcg cgctccatgg                                          20

<210> SEQ ID NO: 82
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 82
agcaggacgc gcgctccatg                                          20

<210> SEQ ID NO: 83
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 83
aagcaggacg cgcgctccat                                          20

<210> SEQ ID NO: 84
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 84
caacaagcag gacgcgcgct                                          20

<210> SEQ ID NO: 85
<211> LENGTH: 15
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 85
catggtcgat aagtc                                               15

<210> SEQ ID NO: 86
<211> LENGTH: 18
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 86
ctccatggtc gataagtc                                            18

<210> SEQ ID NO: 87
<211> LENGTH: 19
<212> TYPE: DNA
<213> ORGANISM: Artificial Sequence
<220> FEATURE:
<223> OTHER INFORMATION: Description of Artificial Sequence: other
      nucleic acid, synthetic DNA

```
<400> SEQUENCE: 87
gctccatggt cgataagtc                                                  19

<210> SEQ ID NO: 88
<211> LENGTH: 21
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 88
gcgctccatg gtcgataagt c                                               21

<210> SEQ ID NO: 89
<211> LENGTH: 22
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 89
cgcgctccat ggtcgataag tc                                              22

<210> SEQ ID NO: 90
<211> LENGTH: 25
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 90
acgcgcgctc catggtcgat aagtc                                           25

<210> SEQ ID NO: 91
<211> LENGTH: 20
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 91
catggtcggt agattctgaa                                                 20

<210> SEQ ID NO: 92
<211> LENGTH: 25
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 92
cacacgctcc atggtcggta gattc                                           25

<210> SEQ ID NO: 93
<211> LENGTH: 25
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 93
```
gcacacgctc catggtcggt agatt                                           25

<210> SEQ ID NO: 94
<211> LENGTH: 25
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 94
agcacacgct ccatggtcgg tagat                                           25

<210> SEQ ID NO: 95
<211> LENGTH: 25
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 95
aagcacacgc tccatggtcg gtaga                                           25

<210> SEQ ID NO: 96
<211> LENGTH: 25
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 96
caagcacacg ctccatggtc ggtag                                           25

<210> SEQ ID NO: 97
<211> LENGTH: 25
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 97
ccaagcacac gctccatggt cggta                                           25

<210> SEQ ID NO: 98
<211> LENGTH: 25
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 98
gccaagcaca cgctccatgg tcggt                                           25

<210> SEQ ID NO: 99
<211> LENGTH: 25
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 99

```
aagccaagca cacgctccat ggtcg                                            25
```

<210> SEQ ID NO: 100
<211> LENGTH: 25
<212> TYPE: DNA
<213> ORGANISM: Artificial Sequence
<220> FEATURE:
<223> OTHER INFORMATION: Description of Artificial Sequence: other
      nucleic acid, synthetic DNA

<400> SEQUENCE: 100

```
acaagccaag cacacgctcc atggt                                            25
```

<210> SEQ ID NO: 101
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 101

```
gaacctctga gctcc                                                       15
```

<210> SEQ ID NO: 102
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 102

```
tccatggtcg ataag                                                       15
```

<210> SEQ ID NO: 103
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 103

```
ggacgcgcgc tccat                                                       15
```

<210> SEQ ID NO: 104
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 104

```
agcagcagca gcaac                                                       15
```

<210> SEQ ID NO: 105
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 105

```
caccagcggc agcag                                                       15
```

<210> SEQ ID NO: 106
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 106
cagagacgtg cacca                                              15

<210> SEQ ID NO: 107
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 107
ggcgtggtcg cagag                                              15

<210> SEQ ID NO: 108
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 108
acaaggttct ggcgt                                              15

<210> SEQ ID NO: 109
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 109
cgtccagctc acaag                                              15

<210> SEQ ID NO: 110
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 110
aaatcttcat cgtcc                                              15

<210> SEQ ID NO: 111
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 111
gacgcagcgg aaatc                                              15

```
<210> SEQ ID NO: 112
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 112
agaagttgca gacgc                                                    15

<210> SEQ ID NO: 113
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 113
tgaggttcgg agaag                                                    15

<210> SEQ ID NO: 114
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 114
ccagtcgggc tgagg                                                    15

<210> SEQ ID NO: 115
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 115
aggcttcgga ccagt                                                    15

<210> SEQ ID NO: 116
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 116
acacactgga aggct                                                    15

<210> SEQ ID NO: 117
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 117
tactgcagac acaca                                                    15
```

```
<210> SEQ ID NO: 118
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 118
tctccacctc tactg                                                    15

<210> SEQ ID NO: 119
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 119
ccggcatgga tctcc                                                    15

<210> SEQ ID NO: 120
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 120
gttgagaccg ccggc                                                    15

<210> SEQ ID NO: 121
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 121
acggctctag gttga                                                    15

<210> SEQ ID NO: 122
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 122
cgctttagaa acggc                                                    15

<210> SEQ ID NO: 123
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 123
cgcatcgacg cgctt                                                    15

<210> SEQ ID NO: 124
```

```
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 124
ggtcggcgtc cgcat                                                        15

<210> SEQ ID NO: 125
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 125
tactgccgcg ggtcg                                                        15

<210> SEQ ID NO: 126
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 126
cgtgtcagca tactg                                                        15

<210> SEQ ID NO: 127
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 127
gagccttgac cgtgt                                                        15

<210> SEQ ID NO: 128
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 128
cgcacgcgga gagcc                                                        15

<210> SEQ ID NO: 129
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 129
tgtgagccgc cgcac                                                        15

<210> SEQ ID NO: 130
<211> LENGTH: 15
```

```
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 130
cggctcccac tgtga                                                    15

<210> SEQ ID NO: 131
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 131
ggaacctgtg cggct                                                    15

<210> SEQ ID NO: 132
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 132
tagctgagca ggaac                                                    15

<210> SEQ ID NO: 133
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 133
cgcctaccag tagct                                                    15

<210> SEQ ID NO: 134
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 134
acacgcaggg cgcct                                                    15

<210> SEQ ID NO: 135
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 135
gtacgctagc acacg                                                    15

<210> SEQ ID NO: 136
<211> LENGTH: 15
<212> TYPE: DNA
```

<213> ORGANISM: Artificial Sequence
<220> FEATURE:
<223> OTHER INFORMATION: Description of Artificial Sequence: other
      nucleic acid

<400> SEQUENCE: 136
tgaggcggga gtacg                                              15

<210> SEQ ID NO; 137
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 137
gtcagttcct tgagg                                              15

<210> SEQ ID NO: 138
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 138
gtcctcgagc gtcag                                              15

<210> SEQ ID NO: 139
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 139
ttatctttag gtcct                                              15

<210> SEQ ID NO: 140
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 140
atggtgccgg ttatc                                              15

<210> SEQ ID NO: 141
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 141
cagcggaggc atggt                                              15

<210> SEQ ID NO: 142
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 142
cttccagagg cagcg                                                    15

<210> SEQ ID NO: 143
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 143
agtcctgtgg cttcc                                                    15

<210> SEQ ID NO: 144
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 144
ggaaagtgca agtcc                                                    15

<210> SEQ ID NO; 145
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 145
ggcgcaagct ggaaa                                                    15

<210> SEQ ID NO: 146
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 146
acgttgcgta ggcgc                                                    15

<210> SEQ ID NO: 147
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 147
cgcccacgac acgtt                                                    15

<210> SEQ ID NO: 148
<211> LENGTH: 15
<212> TYPE: DNA
<213> ORGANISM: Artificial Sequence
<220> FEATURE:

```
<223> OTHER INFORMATION: Description of Artificial Sequence: other
      nucleic acid

<400> SEQUENCE: 148
aacgccctgt cgccc                                                        15

<210> SEQ ID NO: 149
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 149
gcgagccaag aacgc                                                        15

<210> SEQ ID NO: 150
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 150
gcgagccaag aacgc                                                        15

<210> SEQ ID NO; 151
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 151
tgagccactg ctgca                                                        15

<210> SEQ ID NO; 152
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 152
aggcctggct tgagc                                                        15

<210> SEQ ID NO: 153
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 153
cagtaccttg aggcc                                                        15

<210> SEQ ID NO: 154
<211> LENGTH: 15
<212> TYPE: DNA
<213> ORGANISM: Artificial Sequence
<220> FEATURE:
<223> OTHER INFORMATION: Description of Artificial Sequence: other
```

```
        nucleic acid

<400> SEQUENCE: 154
gggcaatgct cagta                                                    15

<210> SEQ ID NO: 155
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 155
gagtgtgctt gggca                                                    15

<210> SEQ ID NO: 156
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 156
aaaggcaggc gagtg                                                    15

<210> SEQ ID NO: 157
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 157
gttcgtagga aaagg                                                    15

<210> SEQ ID NO: 158
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 158
gcgcgaacct gttcg                                                    15

<210> SEQ ID NO: 159
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 159
ggccgggaag gcgcg                                                    15

<210> SEQ ID NO: 160
<211> LENGTH: 15
<212> TYPE: DNA
<213> ORGANISM: Artificial Sequence
<220> FEATURE:
<223> OTHER INFORMATION: Description of Artificial Sequence: other
      nucleic acid
```

<400> SEQUENCE: 160
ggctggtaag ggccg                                               15

<210> SEQ ID NO: 161
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 161
gacaggtcta ggctg                                               15

<210> SEQ ID NO: 162
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 162
aggattgtca gacag                                               15

<210> SEQ ID NO: 163
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 163
cgcccagtcc aggat                                               15

<210> SEQ ID NO: 164
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 164
agtccgcgtt cgccc                                               15

<210> SEQ ID NO: 165
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 165
agccgccatc agtcc                                               15

<210> SEQ ID NO: 166
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 166
ggggacagag agccg                                              15

<210> SEQ ID NO: 167
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 167
gggaacttgt gggga                                              15

<210> SEQ ID NO: 168
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 168
ctggatggcc gggaa                                              15

<210> SEQ ID NO: 169
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 169
gcgctagatt ctgga                                              15

<210> SEQ ID NO: 170
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 170
gtgttgcgca gcgct                                              15

<210> SEQ ID NO: 171
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 171
ctccattcct gtgtt                                              15

<210> SEQ ID NO: 172
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 172
ctgtgggcgt ctcca                        15

<210> SEQ ID NO: 173
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 173
gcgcacacgc ctgtg                        15

<210> SEQ ID NO: 174
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 174
cgccagtgcg gcgca                        15

<210> SEQ ID NO: 175
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 175
cacctgccgc cgcca                        15

<210> SEQ ID NO: 176
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 176
tggggctgca cacct                        15

<210> SEQ ID NO: 177
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 177
gtctaggctg tgggg                        15

<210> SEQ ID NO: 178
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 178

```
tgtggctgag gtcta                                                    15

<210> SEQ ID NO: 179
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 179
cgcagcgagt tgtgg                                                    15

<210> SEQ ID NO: 180
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 180
tacggtggcg cgcag                                                    15

<210> SEQ ID NO: 181
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 181
cgctagggtt tacgg                                                    15

<210> SEQ ID NO: 182
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 182
catctcggag cgcta                                                    15

<210> SEQ ID NO: 183
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 183
ggaccacatg catct                                                    15

<210> SEQ ID NO: 184
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 184
tcagggcgct ggacc                                                    15
```

-continued

<210> SEQ ID NO: 185
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 185
ttgagggagt tcagg                                                      15

<210> SEQ ID NO: 186
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 186
gaacgacaga ttgag                                                      15

<210> SEQ ID NO: 187
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 187
ccagcccagc gaacg                                                      15

<210> SEQ ID NO: 188
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 188
ggcacctgtt ccagc                                                      15

<210> SEQ ID NO: 189
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 189 cagtcccttta ggcac                                                     15

<210> SEQ ID NO: 190
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 190
gcttggctgg cagtc                                                      15

```
<210> SEQ ID NO: 191
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 191
agcactctga gcttg                                                    15

<210> SEQ ID NO: 192
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 192
gctgagatcg agcac                                                    15

<210> SEQ ID NO: 193
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 193
gtctgttgca gctga                                                    15

<210> SEQ ID NO: 194
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 194
gccctgttca gtctg                                                    15

<210> SEQ ID NO: 195
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 195
gcagctcgtc aggct                                                    15

<210> SEQ ID NO: 196
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 196
tccacctcgg gcagc                                                    15
```

```
<210> SEQ ID NO: 197
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 197
tgtcaggtta tccac                                                     15

<210> SEQ ID NO: 198
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 198
tcccgtccag tgtca                                                     15

<210> SEQ ID NO: 199
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 199
aggaagggat tcccg                                                     15

<210> SEQ ID NO: 200
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 200
tccagggacc aggaa                                                     15

<210> SEQ ID NO: 201
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 201
ggagggcagt tccag                                                     15

<210> SEQ ID NO: 202
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 202
ccctcgtggg ggagg                                                     15

<210> SEQ ID NO: 203
```

<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 203
gttcattgag ccctc                                                     15

<210> SEQ ID NO: 204
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 204
ccacgccgga gttca                                                     15

<210> SEQ ID NO: 205
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 205
caggctggga ccacg                                                     15

<210> SEQ ID NO: 206
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 206
cgaacgtgca caggc                                                     15

<210> SEQ ID NO: 207
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 207
ccgacagggt cgaac                                                     15

<210> SEQ ID NO: 208
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 208
gacaccccca ccgac                                                     15

<210> SEQ ID NO: 209
<211> LENGTH: 15

```
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 209
cagggttccc gacac                                                          15

<210> SEQ ID NO: 210
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 210
ggagcagcac caggg                                                          15

<210> SEQ ID NO: 211
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 211
cgggcccctt ggagc                                                          15

<210> SEQ ID NO: 212
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 212
ggcaaagccc cgggc                                                          15

<210> SEQ ID NO: 213
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 213
ttggatctta ggcaa                                                          15

<210> SEQ ID NO: 214
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 214
ttattctgtc ttgga                                                          15

<210> SEQ ID NO: 215
<211> LENGTH: 15
<212> TYPE: DNA
```

```
<213> ORGANISM: Artificial Sequence
<220> FEATURE:
<223> OTHER INFORMATION: Description of Artificial Sequence: other
      nucleic acid

<400> SEQUENCE: 215
agtccattca ttatt                                                    15

<210> SEQ ID NO: 216
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 216
aggcagtttg agtcc                                                    15

<210> SEQ ID NO: 217
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 217
cctgaagcca aggca                                                    15

<210> SEQ ID NO: 218
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 218
acgggactcc cctga                                                    15

<210> SEQ ID NO: 219
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 219
caacgtcctg acggg                                                    15

<210> SEQ ID NO: 220
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 220
gaaaagtcct caacg                                                    15

<210> SEQ ID NO: 221
<211> LENGTH: 15
<212> TYPE: DNA
<213> ORGANISM: Artificial Sequence
```

```
<220> FEATURE:
<223> OTHER INFORMATION: Description of Artificial Sequence: other
      nucleic acid

<400> SEQUENCE: 221
tgaattggtc gaaaa                                                      15

<210> SEQ ID NO: 222
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 222
ggcaaagggt tgaat                                                      15

<210> SEQ ID NO: 223
<211> LENGTH: 15
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 223
ataaaggtgg ggcaa                                                      15

<210> SEQ ID NO: 224
<211> LENGTH: 30
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 224
gcaggacgcg cgctccatgg tcgataagtc                                      30

<210> SEQ ID NO: 225
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 225
ttcatcgtcc agctcacaag                                                 20

<210> SEQ ID NO: 226
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 226
gcgtccgcat cgacgcgctt                                                 20

<210> SEQ ID NO: 227
<211> LENGTH: 20
<212> TYPE: DNA
<213> ORGANISM: Artificial Sequence
<220> FEATURE:
```

```
<223> OTHER INFORMATION: Description of Artificial Sequence: other
      nucleic acid

<400> SEQUENCE: 227
ctgtgcggct cccactgtga                                                  20

<210> SEQ ID NO: 228
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 228
cgggagtacg ctagcacacg                                                  20

<210> SEQ ID NO: 229
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 229
cagttccttg aggcgggagt                                                  20

<210> SEQ ID NO: 230
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 230
ggtcctcgag cgtcagttcc                                                  20

<210> SEQ ID NO: 231
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 231
aagctggaaa gtgcaagtcc                                                  20

<210> SEQ ID NO: 232
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 232
aaaggcaggc gagtgtgctt                                                  20

<210> SEQ ID NO: 233
<211> LENGTH: 20
<212> TYPE: DNA
<213> ORGANISM: Artificial Sequence
<220> FEATURE:
<223> OTHER INFORMATION: Description of Artificial Sequence: other
``` nucleic acid

<400> SEQUENCE: 233
agtccaggat tgtcagacag                                               20

<210> SEQ ID NO: 234
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 234
tcgcccagtc caggattgtc                                               20

<210> SEQ ID NO: 235
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 235
ctgtgggcgt ctccattcct                                               20

<210> SEQ ID NO: 236
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 236
ctgaggtcta ggctgtgggg                                               20

<210> SEQ ID NO: 237
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 237
cgctagggtt tacggtggcg                                               20

<210> SEQ ID NO: 238
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 238
ttgcagctga gatcgagcac                                               20

<210> SEQ ID NO: 239
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 239
tccagtgtca ggttatccac                                            20

<210> SEQ ID NO: 240
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 240
ggagcagcac cagggttccc                                            20

<210> SEQ ID NO: 241
<211> LENGTH: 20
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 241
cccttggagc agcaccaggg                                            20

<210> SEQ ID NO: 242
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
      nucleic acid

<400> SEQUENCE: 242
cncgctccat ggtcgntann t                                          21

<210> SEQ ID NO: 243
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
      nucleic acid

<400> SEQUENCE: 243
ncncgctcca tggtcgntan n                                          21

<210> SEQ ID NO: 244
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
      nucleic acid

<400> SEQUENCE: 244
cncncgctcc atggtcgnta n                                              21

<210> SEQ ID NO: 245
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
      nucleic acid

<400> SEQUENCE: 245
ncncncgctc catggtcgnt a                                              21

<210> SEQ ID NO: 246
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
      nucleic acid

<400> SEQUENCE: 246
nncncncgct ccatggtcgn t                                              21

<210> SEQ ID NO: 247
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
      nucleic acid

<400> SEQUENCE: 247
nnncncncgc tccatggtcg n                                              21

<210> SEQ ID NO: 248
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
      nucleic acid

<400> SEQUENCE: 248
nnnncncncg ctccatggtc g                                              21

<210> SEQ ID NO: 249
<211> LENGTH: 21
<212> TYPE: DNA
<213> ORGANISM: Artificial Sequence
<220> FEATURE:
<221> NAME/KEY: modified_base
<222> LOCATION: (1)..(21)

<223> OTHER INFORMATION: N=inosine
<220> FEATURE:
<223> OTHER INFORMATION: Description of Artificial Sequence: other
     nucleic acid

<400> SEQUENCE: 249
cnnnncncnc gctccatggt c                                      21

<210> SEQ ID NO: 250
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
     nucleic acid

<400> SEQUENCE: 250
gcnnnncncn cgctccatgg t                                      21

<210> SEQ ID NO: 251
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
     nucleic acid

<400> SEQUENCE: 251
agcnnnncnc ncgctccatg g                                      21

<210> SEQ ID NO: 252
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
     nucleic acid

<400> SEQUENCE: 252
aagcnnnncn cncgctccat g                                      21

<210> SEQ ID NO: 253
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
     nucleic acid

<400> SEQUENCE: 253
caagcnnnnc ncncgctcca t                                      21

<210> SEQ ID NO: 254

```
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
      nucleic acid

<400> SEQUENCE: 254
acaagcnnnn cncncgctcc a                                              21

<210> SEQ ID NO: 255
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
      nucleic acid

<400> SEQUENCE: 255
aacaagcnnn ncncncgctc c                                              21

<210> SEQ ID NO: 256
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
      nucleic acid

<400> SEQUENCE: 256
caacaagcnn nncncncgct c                                              21

<210> SEQ ID NO: 257
<211> LENGTH: 21
<212> TYPE: DNA
<213> ORGANISM: Artificial Sequence
<220> FEATURE:
<221> NAME/KEY: modified_base
<222> LOCATION: (1)..(21)
<223> OTHER INFORMATION: N=inosine
<220> FEATURE:
<223> OTHER INFORMATION: Description of Artificial Sequence: other
      nucleic acid

<400> SEQUENCE: 257
gcaacaagcn nnncncncgc t                                              21

<210> SEQ ID NO: 258
<211> LENGTH: 21
<212> TYPE: DNA
<213> ORGANISM: Artificial Sequence
<220> FEATURE:
<223> OTHER INFORMATION: Description of Artificial Sequence: other
      nucleic acid

<400> SEQUENCE: 258
cacacgctcc atggtcggta g                                              21
```

```
<210> SEQ ID NO: 259
<211> LENGTH: 35
<212> TYPE: DNA
<213> ORGANISM: Homo sapiens

<400> SEQUENCE: 259
acuuaucgac cauggagcgc gcguccugcu uguug                         35

<210> SEQ ID NO: 260
<211> LENGTH: 35
<212> TYPE: DNA
<213> ORGANISM: Mus sp.

<400> SEQUENCE: 260
aucuaccgac cauggagcgu gugcuuggcu uguug                         35

<210> SEQ ID NO: 261
<211> LENGTH: 35
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<223> OTHER INFORMATION: Any n = universal base

<400> SEQUENCE: 261
caacaagcnn nnnncncgct ccatggtcgn tannt                         35

<210> SEQ ID NO: 262
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<223> OTHER INFORMATION: Any n - universal base

<400> SEQUENCE: 262
ttcntcgtcn agctcncang g                                        21

<210> SEQ ID NO: 263
<211> LENGTH: 39
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<223> OTHER INFORMATION: Any n = universal base

<400> SEQUENCE: 263
actgccncng ntcngcntcn gnntcnacnc gcnttagaa                     39

<210> SEQ ID NO: 264
<211> LENGTH: 53
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<223> OTHER INFORMATION: Any n = universal base

<400> SEQUENCE: 264
agntnntcna gngtcagttc ctngaggcng gannncncna gnacacgcan ggc     53
```

```
<210> SEQ ID NO: 265
<211> LENGTH: 74
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<223> OTHER INFORMATION: Any n = universal base

<400> SEQUENCE: 265
gcngnnatca gtccncnntc gcccantnca ggattgtcag acaggtctan gntggnnagg      60
gcngggaann cgcg                                                       74

<210> SEQ ID NO: 266
<211> LENGTH: 44
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<223> OTHER INFORMATION: Any n = universal base

<400> SEQUENCE: 266
gcacacgccn ntgggcgtct ccatnccngn gttncgcagc gcta                      44

<210> SEQ ID NO: 267
<211> LENGTH: 42
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<223> OTHER INFORMATION: Any n = universal base

<400> SEQUENCE: 267
tncngnnncn cgcagngant tgtgnctnag gtctagncnn tg                        42

<210> SEQ ID NO: 268
<211> LENGTH: 50
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<223> OTHER INFORMATION: Any n = universal base

<400> SEQUENCE: 268
ctgttgnanc tgagatcnag cacnctgagc ttggcnggca gncctttagg                50

<210> SEQ ID NO: 269
<211> LENGTH: 49
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<223> OTHER INFORMATION: Any n = universal base

<400> SEQUENCE: 269
ccannaaggg attnccntnn agtgncaggt tnnccacntn gggcagctc                 49
```

```
<210> SEQ ID NO: 270
<211> LENGTH: 41
<212> TYPE: DNA
<213> ORGANISM: Homo sapiens

<400> SEQUENCE: 270
cuggaagccg ccgggugccg cuguguagga aagaagcuaa a                   41

<210> SEQ ID NO: 271
<211> LENGTH: 39
<212> TYPE: DNA
<213> ORGANISM: Homo sapiens

<400> SEQUENCE: 271
gguucggaag acuuaucgac cauggagcgc gcguccugc                      39

<210> SEQ ID NO: 272
<211> LENGTH: 29
<212> TYPE: DNA
<213> ORGANISM: Homo sapiens

<400> SEQUENCE: 272
gagcgcgcgu ccugcuuguu gcugcugcu                                 29

<210> SEQ ID NO: 273
<211> LENGTH: 40
<212> TYPE: DNA
<213> ORGANISM: Homo sapiens

<400> SEQUENCE: 273
agauccaaga cagaauaaug aauggacuca aacugccuug                     40

<210> SEQ ID NO: 274
<211> LENGTH: 21
<212> TYPE: DNA
<213> ORGANISM: Homo sapiens

<400> SEQUENCE: 274
ggacucaaac ugccuuggcu u                                         21

<210> SEQ ID NO: 275
<211> LENGTH: 54
<212> TYPE: DNA
<213> ORGANISM: Homo sapiens

<400> SEQUENCE: 275
cucaaacugc cuuggcuuca ggggaguccc gucaggacgu ugaggacuuu ucga     54

<210> SEQ ID NO: 276
<211> LENGTH: 50
<212> TYPE: DNA
<213> ORGANISM: Homo sapiens

<400> SEQUENCE: 276
ggacguugag gacuuuucga ccaauucaac ccuuugcccc accuuuauua          50

<210> SEQ ID NO: 277
<211> LENGTH: 16
<212> TYPE: DNA
<213> ORGANISM: Homo sapiens

<400> SEQUENCE: 277
cuugugagcu ggacga                                               16
```

<210> SEQ ID NO: 278
<211> LENGTH: 35
<212> TYPE: DNA
<213> ORGANISM: Homo sapiens

<400> SEQUENCE: 278
aagcgcgucg augcggacgc cgacccgcgg cagua       35

<210> SEQ ID NO: 279
<211> LENGTH: 15
<212> TYPE: DNA
<213> ORGANISM: Homo sapiens

<400> SEQUENCE: 279 ucacagugggg agccg       15

<210> SEQ ID NO: 280
<211> LENGTH: 45
<212> TYPE: DNA
<213> ORGANISM: Homo sapiens

<400> SEQUENCE: 280
cgugugcuag cguacucccg ccucaaggaa cugacgcucg aggac       45

<210> SEQ ID NO: 281
<211> LENGTH: 15
<212> TYPE: DNA
<213> ORGANISM: Homo sapiens

<400> SEQUENCE: 281
ggacuugcac uuucc       15

<210> SEQ ID NO: 282
<211> LENGTH: 35
<212> TYPE: DNA
<213> ORGANISM: Homo sapiens

<400> SEQUENCE: 282
uacugagcau ugcccaagca cacucgccug ccuuu       35

<210> SEQ ID NO: 283
<211> LENGTH: 19
<212> TYPE: DNA
<213> ORGANISM: Homo sapiens

<400> SEQUENCE: 283
acgcggacug auggcggcu       19

<210> SEQ ID NO: 284
<211> LENGTH: 45
<212> TYPE: DNA
<213> ORGANISM: Homo sapiens

<400> SEQUENCE: 284
uccagaaucu agcgcugcgc aacacaggaa uggagacgcc cacag       45

<210> SEQ ID NO: 285
<211> LENGTH: 55
<212> TYPE: DNA
<213> ORGANISM: Homo sapiens

<400> SEQUENCE: 285
ccccacagcc uagaccucag ccacaacucg cugcgcgcca ccguaaaccc uagcg       55

```
<210> SEQ ID NO: 286
<211> LENGTH: 55
<212> TYPE: DNA
<213> ORGANISM: Homo sapiens

<400> SEQUENCE: 286
gacugccagc caagcucaga gugcucgauc ucagcugcaa cagacugaac agggc         55

<210> SEQ ID NO: 287
<211> LENGTH: 45
<212> TYPE: DNA
<213> ORGANISM: Homo sapiens

<400> SEQUENCE: 287
gcugcccgag guggauaacc ugacacugga cgggaauccc uuccu                    45

<210> SEQ ID NO: 288
<211> LENGTH: 25
<212> TYPE: DNA
<213> ORGANISM: Homo sapiens

<400> SEQUENCE: 288
gugucgggaa cccuggugcu gcucc                                          25

<210> SEQ ID NO: 289
<211> LENGTH: 35
<212> TYPE: DNA
<213> ORGANISM: Artificial Sequence
<220> FEATURE:
<223> OTHER INFORMATION: Description of Artificial Sequence: Consensus
      Oligonucleotide
<220> FEATURE:
<223> OTHER INFORMATION: Any n = base difference

<400> SEQUENCE: 289
caacaagcnn nncncncgct ccatggtcgn tannt                               35
```

ANTISENSE COMPOUNDS TO CD14

This application is the national phase under 35 U.S.C. §371 of prior PCT International Application No. PCT/JP98/00953 which has an International filing date of Mar. 9, 1998 which designated the United States of America, the entire contents of which are hereby incorporated by reference.

TECHNICAL FIELD

The present invention relates to an oligonucleotide comprising a sequence complementary to a part of a gene encoding human CD14. Further, it relates to a pharmaceutical composition comprising said nucleotide and a pharmacologically acceptable carrier.

BACKGROUND TECHNOLOGY 500,000 people in the United States suffer from sepsis caused by bacterial infection and 175,000 people die. The disease is highly lethal and effective therapeutic method is not established (Science, Volume 264, page 365, 1994). The cause has been considered to be a direct effect of lipopolysuccharide (hereinafter designated as "LPS", which is almost synonymic for endotoxin). In 1985, Beutler et al. reported that anti-TNF antibody-administered mouse exhibits resistance to a lethal amount of endotoxin (Science, Volume 229, page 869, 1995). In the meanwhile, Tracy et al. discovered that endotoxin-analogous shock and organic impairment occur in recombinant TNFα-administered animal (Science, Volume 234, page 470, 1996), whereby it was found that the septic shock is caused not by direct effect of LPS, but by excess cytokine production from a macrophage activated by stimulation of LPS, namely hyper-cytokinemia. This discovery was an opportunity to try a therapeutic method targeting TNFα produced in an excess amount by stimulation of LPS. However, the clinical test targeting the TNFα conducted in the beginning of 1990's ended up with disappointing results, wherein good result was not obtained in indexes, e.g. a survival rate of 28 days after (Nature Medicine, Volume 3, page 1193, 1997).

At present, antibiotics are employed for the purpose preventing bacterial infection at present, whereas it is reported that these antibiotics destroy bacterial bodies and a large amount of LPS is released into blood (Scand. J. Infect. Dis., Volume 101, page 3, 1996). This means that the use of antibiotics may cause septic shock or endotoxic shock. Accordingly, in order to prevent the shock, it is important to block the stimulation of LPS simultaneously with the administration of antibiotics.

CD14 is a glycosyl phosphatidylinositol-linked glycoprotein with a molecular weight of 55 kd which is expressed with differentiation and maturation of bone marrow cell. Todd et al. reported the CD14 as surface antigen of human peripheral blood monocytes (New York, Springer-Verlag, pages 424 to 433, 1984). It has been clarified that CD14 is present on membrane of macrophage, monocyte, Kupffer cells, and neutrophil.

Goyert et al, reported the DNA sequence of human CD14 in 1988 (Nucleic Acid Research, Volume 16, No. 9, page 4173, 1988), and Yamamoto et al. reported the DNA sequence of mouse CD14 in 1988 (Somat. Cell Mol. Genet., Volume 14, page 427, 1988). It has been suggested that the CD14 gene is present in a gene cluster of fifth chromosome, where a hematopoietiesis differentiating proliferating factor group such as IL-3 or GM-CSF, G-CSF, etc. are present, and that CD14 gene is involved in the differentiation and maturation of hematopoietiesis tissue. However, detailed function thereof has been unknown.

In 1990, Wright et al. reported that the CD14 is a receptor of LPS of Gram-negative Bacillus endotoxin (Wright et al., Science, Volume 249, page 1431, 1990). Further, recent study discovered that the CD14 binds not only to LPS but also to proteoglycan (Gupta et al., J. Biol. Chem, Volume 271, No. 38, page 23310, 1996). It is also reported that the ingredients of Gram-negative bacteria and Gram-positive bacteria activate the cells through CD14 (Jerome et al., Immunity Volume 1, page 509, 1994). In other words, it is estimated that when organisms are infected with a bacteria, CD14 binds to the bacterial ingredients, whereby macrophage and monocyte expressing the CD14 are activated and various inflammatory factors (inflammatory cytokine, e.g. TNFα, IL-1, IL-6, IL-8, PAI-2, MCP-1, etc., arachidonic metabolites, PAF and nitrogen monoxide, etc.) are released and induced, whereby it contributes to the prevention of the bacterial infection in the early phase of infection (Matthew et al., J. Biol. Chem., Volume 60, page 728, 1996). On the other hand, it is also estimated that under disease conditions, such as sepsis, activation of macrophage due to a large quantity of LPS from bacteria leads to release of a large amount of TNFα into blood, and causes shock (Fearn. S et al., J. Exp. Med., Volume 181, page 857, 1995).

At present, the cytokine production mechanism by LPS via CD14 is estimated as described below. In short, aggregated LPS originated from bacterium together with LPS-binding protein (LBP) forms a complex in blood, and consequently, the LPS monomer becomes capable of efficiently binding to CD14 molecules on the macrophage in a proportion of 1:1. Signal of the LPS bound to the surface of the cells is transmitted into the cell through an unknown route analogous to ceramide; NFκB which is a transcription factor is activated in the cell; and the production of various cytokines including TNFα is induced (Ulevith et al., Annual Review of Immunology, 13, 437, 1995). These facts indicate that primary response of the host in the case of bacterial infection initiates from the response of the CD14 on monocyte/macrophage to LPS or Gram-positive bacterium ingredients.

By the way, there are two forms of the CD14 molecule, i.e. membrane-binding form and soluble-form. The production of the soluble CD14 is assumed that the membrane-binding CD14 is cleaved by protease to become soluble CD14 (Philip et al., Eur. J. Immunol., Volume 25, page 604, 1995).

It is reported that the soluble CD14 binds to LPS molecule in the blood and transports it to HDL, so that the soluble CD14 serves for the clearance of the LPS (Wurfel et al., J. Exp. Med., Volume 186, page 1743, 1995). On the other hand, it is assumed that the membrane CD14 binds to LPS, allows to transmit the signal into cells to induce inflammatory cytokine. In short, the CD14 possesses functions contrary to each other, i.e. the effect of removing LPS and the effect of inducing inflammatory factors.

JP-A 5-501399 discloses a method for treating sepsis by employing anti-CD14 antibody. The anti-CD14 antibody inhibits the binding between CD14 and LPS, to enable blockage of the signal via CD14 to thereby suppress the expression of the inflammatory cytokine. The sepsis is thereby treated. WO93/19772 and WO96/2057 disclose the treatment of sepsis by employing soluble CD14.

Nevertheless, when high mortality and numbers of patients of septic shock are taken into consideration, provision of more effective medicines is required.

DISCLOSURE OF THE INVENTION

The present inventors have investigated in order to provide more effective medicines against septic shock. The inventors have predicted that the inflammatory cytokine produced from Kupffer cells in liver by LPS stimulation plays an important role, and have assumed that specific blocking of the binding between the LPS and the CD14 on the Kupffer cell in a way of not affecting the soluble CD14 contributing the removal of LPS, or the CD14 on aveolar macrophage or peritoneal macrophage, or on other macrophages contributing for bacterial infection prevention on each site would be clinically effective. The inventors have assumed that the use of an antisense oligonucleotide accumulative in liver should act with the CD14 on the liver Kupffer cells at a high selectivity.

It is known that CD14 is very weakly expressed on mouse Kupffer cell in normal state whereas CD14 is strongly expressed when the cell is stimulated by LPS. On the other hand, it has been known that the liver is an organ most susceptible to shock, and that the reduction of liver function considerably affects constitutional symptom. The present inventors provide a medicine effective to sepsis or septic shock based on a new view of selectively inhibiting the CD14 on Kupffer cell whose expression is induced by LPS stimulation, and mainly inhibiting the production of inflammatory cytokine from Kupffer cells. In other words, the present inventors provide an antisense oligonucleotide to CD14 as medicament effective to sepsis or septic shock.

It has been totally unknown whether the antisense oligonucleotide of CD14 inhibits the expression of CD14 to the extent utilizable as a medicine or whether it is applicable to the treatment of sepsis or not. The inventors have investigated and confirmed that the antisense oligonucleotide of CD14 is utilizable as medicine. Further, the inventors have succeeded in the following manner to determine the region which is particularly effective as the target of antisense nucleotide within the gene of ca. 1.4 kb encoding the CD14.

The inventors have identified the active regions for 5' non-coding region and translation initiation region, by translation inhibition experiment using a human CD14 luciferase fusion protein expression system, and combination of CD14 protein expression inhibitory activity due to recombinant HeLa cell and TNFα production inhibitory activity due to human macrophage-like cell lines. With regard to the coding region and 3' non-coding region, the active region of which cannot easily identified, the inventors have succeeded to identify the active regions by employing a screening using RNaseH which specifically cleaves the duplex of a target RNA and an antisense oligonucleotide. Consequently, they have confirmed the effect and toxicity of these active regions by cell culture or animal system, and completed the invention.

In short, the present invention provides oligonucleotides hybridizing with at least a part of a gene encoding human CD14. Of the oligonucleotides, an oligonucleotide comprising a sequence complementary to at least a part of a gene encoding human CD14 is preferred.

Moreover, the invention provides oligonucleotides containing a sequence complementary to at least one sequence selected from the group consisting of 5' non-coding region, translation initiation region, coding region and 3' non-coding region of a human CD14 mRNA, and at least a part thereof.

Further, the invention provides oligonucleotides hybridizing with or being complementary to any one of the sequences or at least a part of the sequence selected from the group consisting of:
(1) a nucleotide sequence of 40 mer positioning from 23rd cytosine to 62nd adenine,
(2) a nucleotide sequence of 39 mer positioning from 93rd guanine to 131st cytosine,
(3) a nucleotide sequence of 29 mer positioning from 117th guanine to 145th uridine,
(4) a nucleotide sequence of 40 mer positioning from 1241st adenine to 1280th guanine,
(5) a nucleotide sequence of 22 mer positioning from 1264th guanine to 1285th cytosine,
(6) a nucleotide sequence of 54 mer positioning from 1267th cytosine to 1320th adenine,
(7) a nucleotide sequence of 50 mer positioning from 1301st guanine to 1350th adenine,
(8) a nucleotide sequence of 20 mer positioning from 184th cytosine to 203rd adenine,
(9) a nucleotide sequence of 20 mer positioning from 324th adenine to 343rd cytosine,
(10) a nucleotide sequence of 20 mer positioning from 394th uridine to 413th guanine,
(11) a nucleotide sequence of 46 mer positioning from 444th cytosine to 489th cytosine,
(12) a nucleotide sequence of 20 mer positioning from 534th guanine to 553rd uridine,
(13) a nucleotide sequence of 25 mer positioning from 644th uridine to 668th uridine,
(14) a nucleotide sequence of 75 mer positioning from 684th cytosine to 758th uridine,
(15) a nucleotide sequence of 35 mer positioning from 794th adenine to 828th guanine,
(16) a nucleotide sequence of 55 mer positioning from 864th cytosine to 918th guanine,
(17) a nucleotide sequence of 55 mer positioning from 994th guanine to 1048th cytosine,
(18) a nucleotide sequence of 45 mer positioning from 1064th guanine to 1108th uridine, and
(19) a nucleotide sequence of 30 mer positioning from 1194th guanine to 1223rd guanine, in a nucleotide sequence of SEQ.ID. No.1.

Of these oligonucleotides, oligonucleotides which inhibit the human CD14 expression are preferred. For instance, an oligonucleotide exhibiting a high binding activity with a human CD14 gene in an RNase H cleavage experiment, and an oligonucleotide capable of suppressing the expression of human CD14 by at least 30% in a translation inhibition experiment are preferred.

The nucleotide number of present oligonucleotides is preferably in the range of 10 to 50, and most preferably in the range of 15 to 30.

The present invention also provides oligonucleotides wherein at least one of the internucleotides linkages contains a sulphur atom.

Further, the present invention provides an oligonucleotide which comprises at least one nucleotide sequence selected from the group consisting of SEQ.ID. Nos. 10, 11, 12, 13, 16, 19, 20, 21, 22, 23, 24, 25, 26, 27, 28, 29, 32, 33, 34, 35, 36, 37, 39, 40, 41, 42, 45, 46, 47, 48, 49, 50, 51, 52, 53, 54, 55, 56, 57, 58, 59, 61, 62, 63, 64, 70, 71, 72, 73, 74, 75, 76, 77, 78, 79, 81, 83, 85, 86, 87, 88, 89, 90, 102, 103, 109, 123, 124, 125, 130, 135, 136, 137, 138, 144, 155, 156, 159, 160, 161, 162, 163, 164, 165, 170, 171, 172, 177, 178, 179, 180, 181, 190, 191, 192, 193, 194, 196, 197, 198, 199, 209, 210, 215, 216, 220, 221, 224, 225, 226, 227, 228, 229, 230, 231, 232, 233, 234, 235, 236, 237, 238, 239, 240, 241, 242, 243, 244, 245, 246, 247 and 248; and comprises up to 30 nucleotides.

Further, the present invention provides a pharmaceutical composition comprising an oligonucleotide hybridizing with a gene encoding the CD14 as its effective component. In addition to the oligonucleotides hybridizing with a gene encoding the CD14, if necessary, the present pharmaceutical composition may comprise a pharmacologicaly acceptable carrier. The pharmaceutical composition is preferably a prophylactic/therapeutic agent against sepsis or septic shock, or disorders caused by an inflammatory factor induced by human CD14.

BRIEF EXPLANATION OF THE DRAWINGS

FIG. 10: A drawing comparing the human antisense oligonucleotide (SEQ ID NO: 259) and the mouse antisense oligonucleotide (SEQ ID NO: 260) around the translation initiation region. (Consensus sequence SEQ ID NO: 259)

FIG. 11: A graph indicating inhibitory activity of consensus oligonucleotides to the expression of the human CD14/luciferase fusion protein.

FIG. 12: A graph indicating mouse TNFα production inhibitory activity of the consensus oligonucleotides.

SUMMARY OF THE INVENTION

Figure 1:
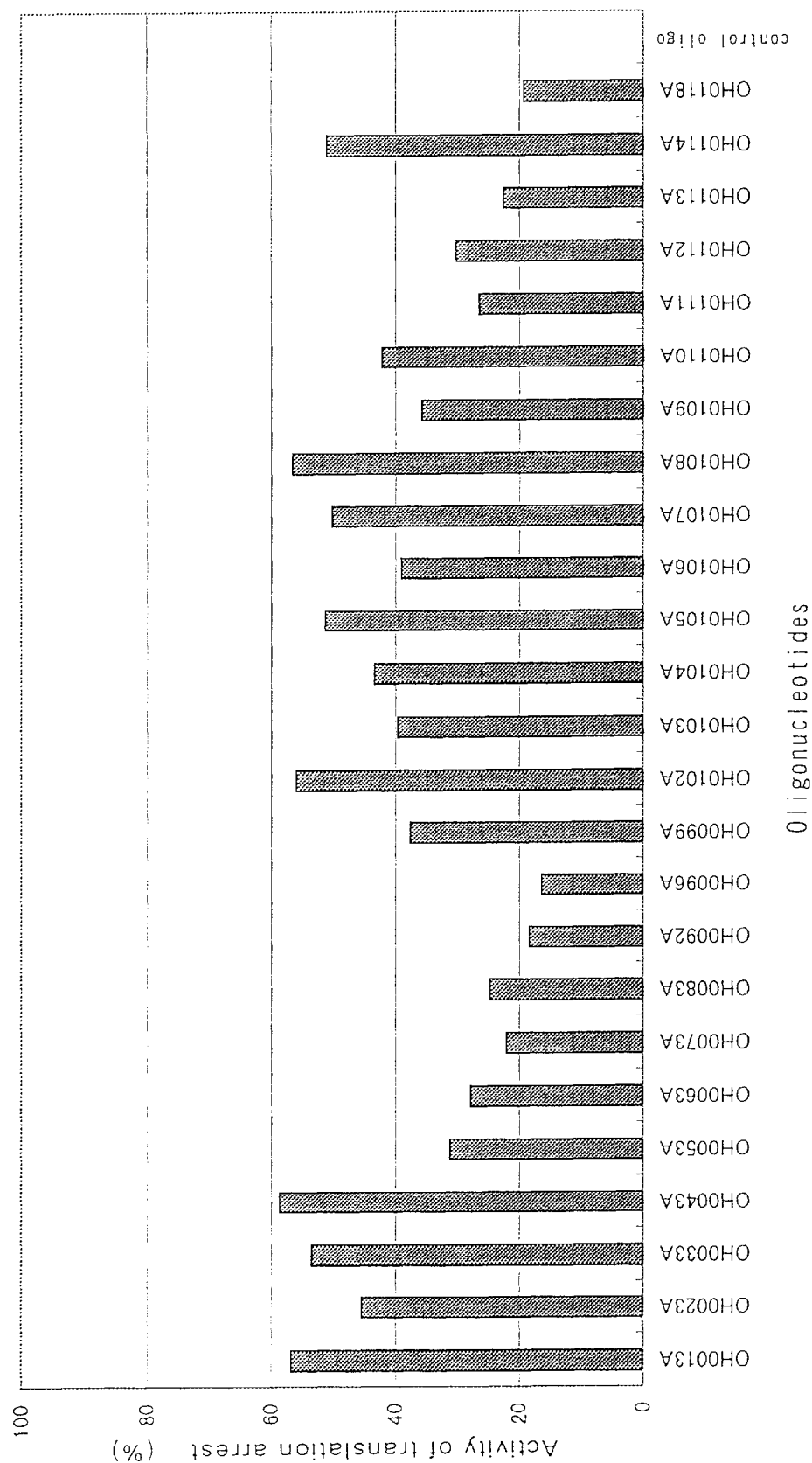
FIG. 1: A graph indicating CD14 translation-inhibitory activity of the antisense oligonucleotides complementary to a gene encoding human CD14.

Hereinafter, the present invention is illustrated.

The oligonucleotides of the present invention hybridizes with at least a part of the gene encoding human CD14. Preferably, the oligonucleotides is the one which comprises a sequence complementary to at least a part of the gene encoding human CD14.

In the description of the present invention, the term "oligonucleotide" includes all of the oligonucleotides wherein a plurality of nucleotides each composed of a base, a phosphate and a sugar are bound, and derivatives thereof. The representative oligonucleotides are DNA and RNA. The oligonucleotide derivatives include all of those wherein steric structure and function are analogous to the oligonucleotides. Exemplary, derivatives include those wherein other substance is bound to 3'-end or 5'-end of the oligonucleotide, those wherein any one of the base, the sugar and the phosphate of the oligonucleotide is substituted or modified, those wherein the base, the sugar or the phosphate is the one not present in nature, and those having a skeleton other than sugar-phosphate framework (backbone).

The term "gene" in the present specification means a chromosome DNA or a transcript (mRNA or a precursor thereof). The word "gene encoding CD14" means the structural gene defining the CD14 amino acid sequence, an intervening sequence (introns) present in the midst of the structural gene, a ucleotide sequence concerning the expression of CD14 which is present in the upstream of the structural gene (promoter, operator, etc.), and a ucleotide sequence in the downstream of the structural gene. Typical sequences of the gene encoding human CD14 are indicated by SEQ.ID. No. 1 and No. 2 in the Sequence Listing.

The term "to hybridize" in the present specification means to form a specific binding between bases of the DNA or the RNA. The strength of the hybridization is not limited as long as Tm value is at least 45° C. in 0.15M phosphate buffer. Preferably, the strength is such that the Tm value is at least 55° C. The specific binding is generally formed by complementary binding. However the type of the binding is not limited. In other words, the oligonucleotides of the present invention may not necessarily have a sequence fully complementary to the target sequence as long as the oligonucleotide specifically binds to at least a part of the gene encoding human CD14; may contain a universal base, for example, inosine or 5-nitroindole; and may partially contain a base or a sequence which is not complementary to the target sequences. The term "to hybridize" used herein also includes the cases wherein a double-strand or a triple-strand is formed in Watson-Crick base pairing or Hoogsteen base pairing or of the both base pairings. The term "complementary sequence" designates the sequence wherein complementary base pairs are formed in a base-specific manner to the ucleotide sequence of the DNA or the RNA. In general, the complementary base pairs are formed between C (cytosine) and G (guanine), between T (thymine) and A (adenine), and between U (uracil) and A (adenine).

The oligonucleotide of the present invention preferably hybridizes with at least a part of the mRNA encoding human CD14 or a precursor thereof.

The length of the present oligonucleotides is not particularly limited. In general, any nucleotide sequence containing at least 10 nucleotide is considered to have a specific sequence. Accordingly, all of the present oligonucleotides having a nucleotide sequence of at least 10 uncleotides are expected to be hybridizable specifically to the gene encoding the human CD14.

On the other hand, an excessively long oligonucleotide is not suitable for incorporation into a cell. The oligonucleotides of the invention may have any length. In consideration of the incorporation of the present oligonucleotides in the cell in order to inhibit the expression of the human CD14, it is preferred that the present oligonucleotide hybridizes with a gene encoding human CD14, and the nucleotide has a length of 10 mer to 50 mer, and preferably 15 mer to 30 mer. In other words, the antisense oligonucleotide of the present invention is, for instance, a oligonucleotide which hybridizes with or which is complementary to the sequence of n to n+10th, n to n+11th, n to n+12th, n to n+13th, n to n+14th, n to n+15th, n to n+16th, n to n+17th, n to n+18th, n to n+19th, n to n+20th, n to n+21st, n to n+22nd, n to n+23rd . . . , or n to n+50th (n=1 to 1341) within SEQ. ID. No. 1 or No. 2.

The oligonucleotide of the present invention may target any site of the gene encoding human CD14, the mRNA encoding human CD14, or a precursor thereof. In other words, the site to which the present oligonucleotide is bound is not particularly limited. However, it is preferable that the oligonucleotide of the present invention binds to any of translation initiation regions, coding regions, 5' non-coding regions, 3' non-coding regions, ribosome-binding regions, capping regions, splicing regions, and loop portions forming a hairpin structure of the mRNA or the mRNA precursors. Among these, the translation initiation region of the human CD14 mRNA is most suitable for the target of the present oligonucleotides in view of the high effect. A coding region is preferred in view of the accumulation of the present oligonucleotide in nucleus.

Specifically, the oligonucleotide of the present invention is preferably designed to target one region chosen from the group consisting of the following (1) to (19) within the mRNA to human CD14 of SEQ. ID. No. 1.

(1) a nucleotide sequence of 40 nucleotides from 23rd cytosine to 62nd adenine,
(2) a nucleotide sequence of 39 nucleotides from 93rd guanine to 131st cytosine,
(3) a nucleotide sequence of 29 nucleotides from 117th guanine to 145th uridine,
(4) a nucleotide sequence of 40 nucleotides from 1241st adenine to 1280th guanine,
(5) a nucleotide sequence of 22 nucleotides from 1264th guanine to 1285th cytosine,
(6) a nucleotide sequence of 54 nucleotides from 1267th cytosine to 1320th adenine,
(7) a nucleotide sequence of 50 nucleotides from 1301st guanine to 1350th adenine,
(8) a nucleotide sequence of 20 nucleotides from 184th cytosine to 203rd adenine,
(9) a nucleotide sequence of 20 nucleotides from 324th adenine to 343rd cytosine,
(10) a nucleotide sequence of 20 nucleotides from 394th uridine to 413th guanine,
(11) a nucleotide sequence of 46 nucleotides from 444th cytosine to 489th cytosine,
(12) a nucleotide sequence of 20 nucleotides from 534th guanine to 553rd uridine,
(13) a nucleotide sequence of 25 nucleotides from 644th uridine to 668th uridine,
(14) a nucleotide sequence of 75 nucleotides from 684th cytosine to 758th uridine,
(15) a nucleotide sequence of 35 nucleotides from 794th adenine to 828th guanine,
(16) a nucleotide sequence of 55 nucleotides from 864th cytosine to 918th guanine,
(17) a nucleotide sequence of 55 nucleotides from 994th guanine to 1048th cytosine,
(18) a nucleotide sequence of 45 nucleotides from 1064th guanine to 1108th uridine, and
(19) a nucleotide sequence of 30 nucleotides from 1194th guanine to 1223rd guanine.

Of the above nucleotide sequences (1) to (19), the region comprising any one of the nucleotide sequences (1), (2), (4), (5), (7), (8), (11), (16) and (19) is considered to be particularly effective as the target of the present oligonucleotides.

Accordingly, the preferable embodiments of the present oligonucleotide are the oligonucleotides hybridizing with any one of sequence selected from the above (1) to (19), and the oligonucleotides hybridizing with at least a part of any one of the sequence selected from the above (1) to (19). Preferably, the oligonucleotide is the one hybridizing with any one of the sequence selected from the nucleotide sequences (1), (2), (4), (5), (7), (8), (11), (16) and (19), and oligonucleotides hybridizing with at least a part of any one of the sequence selected from the nucleotide sequences (1), (2), (4), (5), (7), (8), (11), (16) and (19). More preferably, the present oligonucleotide is the one having a nucleotide sequence complementary to any one of the sequence selected from the above (1) to (19), or the nucleotide sequence complementary to at least a part of any one of the sequence selected from the above (1) to (19), preferably the nucleotide sequence complementary to any one of the sequence selected from the nucleotide sequences (1), (2), (4), (5), (7), (8), (11), (16) and (19), and the nucleotide sequence complementary to at least a part of any one of the sequence selected from the nucleotide sequences (1), (2), (4), (5), (7), (8), (11), (16) and (19). Such oligonucleotide may preferably comprise 10 to 50 nucleotides. A preferred example of the present oligonucleotides is an oligonucleotide having a nucleotide sequence hybridizing with or complementary to at least 10 consecutive nucleotides within any nucleotide sequence selected from the above (1) to (19).

Of above sequences, sequences (1) to (3) are located within the region of the 5' non-coding region to the translation initiation site of the mRNA encoding human CD14, and sequences (8) to (19) are located within the coding region, and sequences (4) to (8) are located within the 3' non-coding region.

The oligonucleotide of the present invention may preferably exhibit an inhibitory activity to the expression of the human CD14. The present inventors discovered as indicated in Example 13 that the RNaseH cleavage experiment is effective as an indicator in selecting the oligonucleotide effective for inhibiting the expression of the CD14. Accordingly, among the oligonucleotides hybridizing with, or having the sequences complementary to at least a part of the human CD14 mRNA, the preferable oligonucleotides exhibit the score of at least 1, and preferably, at least 2 in the RNase H cleavage experiment. Furthermore, the oligonucleotides capable of inhibiting at least 20%, and preferably at least 40% of the human CD14 expression in human CD14/luciferase fusion protein expression-inhibition experiment; the oligonucleotides capable of inhibiting the TNFα production in TNFα production-inhibition experiment, and the oligonucleotides capable of inhibiting at least 30% of the CD14 translation in CD14 translation-inhibition experiment are preferred.

Further, the present invention provides an oligonucleotide having at least one nucleotide sequence selected from the group consisting of SEQ ID Nos. 10, 11, 12, 13, 16, 19, 20, 21, 22, 23, 24, 25, 26, 27, 28, 29, 32, 33, 34, 35, 36, 37, 39, 40, 41, 42, 45, 46, 47, 48, 49, 50, 51, 52, 53, 54, 55, 56, 57, 58, 59, 61, 62, 63, 64, 70, 71, 72, 73, 74, 75, 76, 77, 78, 79, 81, 83, 85, 86, 87, 88, 89, 90, 102, 103, 109, 123, 124, 125, 130, 135, 136, 137, 138, 144, 155, 156, 159, 160, 161, 162, 163, 164, 165, 170, 171, 172, 177, 178, 179, 180, 181, 190, 191, 192, 193, 194, 196, 197, 198, 199, 209, 210, 215, 216, 220, 221, 224, 225, 226, 227, 228, 229, 230, 231, 232, 233, 234, 235, 236, 237, 238, 239, 240, 241, 242, 243, 244, 245, 246, 247 and 248 of the Sequence Listing. It should be noted that phosphorothioate oligonucleotide and phosphodiester oligonucleotide are admixed in the above sequence list. However, the list indicates oligonucleotides having nucleotide sequences of the above sequence Nos., regardless of the presence or the absence of modification or the type of derivative. The oligonucleotide of the present invention has the above nucleotide sequence, and preferably, a length of 30 nucleotides or less.

With the development in the antisense technology, various derivatives have been discovered for the purpose of improving the medical effects of the oligonucleotides. At present, various oligonucleotide derivatives having high binding affinity to the target DNA or mRNA, histo-selectivity, ability of transmission through cell wall, nuclease resistance, and stability in the cell have been obtained. As explained above, the present oligonucleotides include all kinds of derivatives including the one composed of the base, the phosphate, or the backbone structure which is not present in nature. The examples of the derivatives of the present invention include the derivatives having phosphodiester linkage, phosphorothioate linkage, methylphosphonate linkage, phosphoroamidate linkage, phosphorodithioate linkage, and morpholino group in all or a part of its backbone structure (Shôji Yôko, et al., "Gan to Kagakuryoho", Volume 20, pp. 1899 to 1907, 1993).

Also included in the examples of the derivatives are deoxyribonucleotide guanidine (DNG) (Robert P, et al., Proc. Natl. Acad. Sci. USA, Volume 92, page 6097, 1995), the one wherein 2'-position of the sugar moiety is substituted with another atom or a substituent, and the one wherein the sugar moiety is modified, such as α-ribose (Bertrand J R. Biochem. Biophys. Res. Commun., Volume 164, page 311, 1989).

Also included in the present invention are oligonucleotide derivatives wherein the sugar moiety is substituted with another substance, those wherein some of the bases are substituted with inosine or a universal bases (a base capable of binding to any of A, T, C and G), those wherein cholesterol, acridine, poly-L-lysine, psoralen, or a long chain alkyl is bound to the 5' or 3'-end or within the oligonucleotide (G. Degols, et al., Nucleic Acid Research, Volume 17, page 9341, 1989; A. McConnaghie, et al., J. Med. Chem., Volume 38, page 3488, 1993; G. Godard, et al., Eur. J. Biochem., Volume 232, page 404, 1995).

As a preferred example of the above-described derivatives, the present invention provides derivatives having phosphorothioate linkage as its backbone structure, i.e. an oligonucleotide wherein at least one internucleotides linkage contains sulphur atom.

Suitable examples of such oligonucleotides are the oligonucleotide selected from SEQ. ID. Nos. 10, 11, 12, 13, 16, 19, 20, 21, 22, 23, 24, 25, 26, 27, 28, 29, 32, 33, 34, 35, 36, 37, 39, 40, 41, 42, 45, 46, 47, 48, 49, 50, 51, 52, 53, 54, 55, 56, 57, 58, 59, 225, 226, 227, 228, 229, 230, 231, 232, 233, 234, 235, 236, 237, 238, 239, 240, 241, 242, 243, 244, 245, 246, 247, and 248 (in other words, the oligonucleotides having phosphorothioate linkage, and having a sequence selected from the sequences of above SEQ ID numbers).

As explained above, as long as the present oligonucleotide hybridizes with the target sequence as described above, the oligonucleotide may not necessarily contain a sequence fully complementary to a part of the nucleotide sequence of the target region. On the contrary, in consideration of the animal experiments that will be necessary in the development of the pharmaceuticals, an oligonucleotide which hybridizes not only with the gene encoding the human CD14 but also the gene encoding the CD14 of the model animal will be necessary. Such oligonucleotides may be obtained by targeting the region exhibiting a high homology between the human and the model animal in the nucleotide sequences encoding the CD14. For example, SEQ. ID. No. 3 and No. 4 in the Sequence Listing are nucleotide sequences encoding mouse CD14. An oligonucleotides which hybridizes with both of the gene encoding the mouse CD14 and the gene encoding the human CD14 can be prepared by identifying the region exhibiting high homology between the human and the mouse and using the complementary nucleotide sequence for the consensus bases between the human and the mouse, and universal bases such as inosine and 5-nitroindole for the mismatched bases. Oligonucleotides capable of hybridizing with the gene encoding the human CD14 and also with the genes encoding the CD14 of any two or more non-human animals can be prepared in the same manner. As matter of course, if necessary, phosphorothioate linkage may be introduced to backbone. Among such oligonucleotides, the preferable oligonucleotides which are expected to exhibit a high CD14 expression-inhibitory activity can be produced by designing the oligonucleotide to target the regions comprising the nucleotide sequence selected from (1) to (9). For the purpose improving the complementarity of the oligonucleotides with the human CD14 and other animals' CD14, the targeting region may be extend to several nucleotides downstream or several nucleotides upstream of said region. Examples of such antisense oligonucleotides include oligonucleotides having the nucleotide sequence wherein at least one base is substituted with a universal base in the nucleotide sequence complementary to the nucleotide sequence selected from the following nucleotide sequences (1) to (9). Also included as exemplary antisense oligonucleotides are oligonucleotides having the nucleotide sequence wherein at least one base is substituted with a universal base in the nucleotide sequence complementary to arbitrary portion comprising at least 10 consecutive nucleotides within the nucleotide sequence selected from the following nucleotide sequences (1) to (9).

(1) a nucleotide sequence of 29 nucleotides from 103rd adenine to 131st cytosine in SEQ. ID. No.1,
(2) a nucleotide sequence of 20 nucleotides from 184th cytosine to 203rd adenine in SEQ. ID. No.1,
(3) a nucleotide sequence of 20 nucleotides from 324th adenine to 343rd cytosine in SEQ. ID. No.1,
(4) a nucleotide sequence of 46 nucleotides from 444th cytosine to 489th cytosine in SEQ. ID. No.1,
(5) a nucleotide sequence of 75 nucleotides from 684th cytosine to 758th uridine in SEQ. ID. No.1,
(6) a nucleotide sequence of 35 nucleotides from 794th adenine to 828th adenine in SEQ. ID. No.1,
(7) a nucleotide sequence of 45 nucleotides from 864th cytosine to 908th adenine in SEQ. ID. No.1,
(8) a nucleotide sequence of 53 nucleotides from 994th guanine to 1046th guanine and in SEQ. ID. No.1,
(9) a nucleotide sequence of 45 nucleotides from 1064th guanine to 1108th uridine in SEQ. ID. No.1.

More specifically, the oligonucleotide is the one having the entire region of the nucleotide sequence selected from the following (10) to (18), or the one having any consecutive partial sequence comprising at least 10 contiguous oligonucleotides. These sequences have been designed to be hybridized able to any of human, mouse and simian CD14 mRNA.

(10) CAA CAA GCX XXX XXC XCG CTC CAT GGT CGX TAX XT (SEQ ID NO: 261)
(11) TTC XTC GTC XAG CTC XCA XGG (SEQ ID NO: 261)
(12) ACT GCC XCX GXT CXG CXT CXG XXT CXA CXC GCX TTA GAA (SEQ ID NO: 263)
(13) AGX TXX TCX AGX GTC AGT TCC TXG AGG CXG GAX XXC XCX AGX ACA CGC AXG GC (SEQ ID NO: 264)
(14) GCX GXX ATC AGT CCX CXX TCG CCC AXT XCA GGA TTG TCA GAC AGG TCT AXG XTG GXX AGG GCX GGG AAX XCG CG (SEQ ID NO: 266)
(15) GCA CAC GCC XXT GGG CGT CTC CAT XCC XGX GTT XCG CAG CGC TA (SEQ ID NO: 266)
(16) TXC XGX XXC XCG CAG XGA XTT GTG XCT XAG GTC TAG XCX XTG (SEQ ID NO: 266)

(17) CTG TTG XAX CTG AGA TCX AGC ACX CTG AGC TTG GCX GGC AGX CCT TTA GG (SEQ ID NO: 268)
(18) CCA XXA AGG GAT TXC CXT XXA GTG XCA GGT TXX CCA CXT XGG GCA GCT C (SEQ ID NO: 269)

(In the above sequences (10) to (18), X stands for a universal base.)

More specifically, the exemplary oligonucleotides are those having the nucleotide sequences of SEQ ID Nos. 242, 243, 244, 245, 246, 247, 248, 249, 250, 251, 252, 253, 254, 255, 256 and 257.

Next, the process for preparing the present oligonucleotides is explained.

Oligonucleotides and derivatives thereof may be prepared by a known method (e.g. S. Agrawal, et al., Protocol for oligonucleotides and Analogs, Method in Molecular Biology series, Volume 20, Humana Press; S. Agrawal, et al., Antisense Research and Development, Volume 4, page 185, 1994).

When the oligonucleotide is a natural DNA or RNA, the oligonucleotides may be prepared by chemical synthesis using a synthesizer, or by PCR using the gene encoding the human CD14 for the template. Some derivatives, such as methylphosphonate modification and phosphorothioate modification, can be synthesized using a chemical synthesizer (e.g. model 394, manufactured by Perkin-Elmer Japan K.K.). In such a case, the synthesis may be conducted in accordance with the manual attached to the chemical synthesiser, and the thus obtained product may be purified by HPLC using reverse phase chromatography or the like to thereby obtain the desired oligonucleotide derivative.

In the case of the oligonucleotide which hybridizes with at least a part of the gene encoding the human CD14, the inhibitory activities of the oligonucleotides synthesized by the above-described procedure in the expression of human CD14 may be confirmed by a translation-inhibition experiment using a human CD14/luciferase fusion protein expression system. Also, the effect of inhibiting the expression of the inflammatory factor induced via the human CD14 can be confirmed using a cell-based evaluation system. This cell-based evaluation system elucidaes the effectivity of the oligonucleotide differenciating THP-1 cell into macrophage-like cell by treating it with PMA and vitamin D3 as inducer, stimulating the cell by LPS to produce TNFα, adding various oligonucleotides to inspect their effect by the inhibitory activity of the TNFα as indicator. The present oligonucleotides may also be evaluated or chosen by using its activity to inhibit the human CD14 expression as indicator using a recombinant cell expressing the human CD14. Alternatively, the oligonucleotide may be evaluated and chosen by using binding activity values in RNaseH cleavage experiment as index.

Next, the use of the present oligonucleotides is explained.

The present oligonucleotides are characterized by its binding to the gene encoding the human CD14, and therefore, they can be employed as diagnosis probe for detecting the human CD14 gene in the specimen. In case of the use of the present oligonucleotides as the diagnosis probe, they are labeled with radio isotope, enzyme, fluorescent substance, luminous substance, etc. by the method known in the art. Subsequently, DNA or mRNA is prepared from the cell of a patient whose CD14 expression is to be examined in the known manner. A marker probe is added to this sample and the mixture is incubated, followed by washing to remove the unreacted marker probe. If the specimen contains the human CD14 DNA or RNA, the marker probe will be bound to such DNA or RNA. Binding of the marker can be detected by luminescence, fluorescence, radioactivity, etc. using a labeled enzyme, fluorescent substance, luminescent substance or radioisotope as the indicator.

Therefore, the present oligonucleotides can be used as a diagnosis probe for detecting increase or decrease in CD14 expression level in tissues or cells as a response against external stimulation, for diagnosing disorders caused by inflammatory factor generated via CD14, such as systemic inflammatory response syndrome, sepsis and septic shock, ulcerative colitis, Crohn's disease, autoimmune reaction and disease, allergic disease, cancer, graft-versus-host reaction, periodontosis or osteoporosis. The oligonucleotides can also be used for the diagnosis wherein inflammation degree, therapeutical method and prognosis are determined.

In the use of the present oligonucleotides for medical use, the one with a purity suitable for medical use may be used in a dosage form suitable for human administration, if necessary, together with a pharmacologically acceptable additive. Such use will be described in detail in the following section where the pharmaceutical compositions are described.

Next, the pharmaceutical composition of the present invention are explained. The pharmaceutical composition of the present invention comprises the oligonucleotides as described above as its active component. In other words, the pharmaceutical composition of the present invention comprises the oligonucleotide which binds to the gene encoding the human CD14 and which is capable of inhibiting the human CD14 expression as its active ingredient. The pharmaceutical composition of the present invention may be used by directly dissolving or suspending the oligonucleotide of the purity suitable for medical use in a suitable solvent, or by enclosing in liposome, or by inserting into a suitable vector. If necessary, a pharmaceutically acceptable addtive may be added to the oligonucleotide of the present invention, and the mixture may be formed to a suitable dosage form such as injection, tablet, capsule, collyrium, creme, suppository, spray, cataplasm, etc. Exemplary pharmacologically acceptable carriers include solvent, base, stabiliser, antiseptic, dissolution agent, excipient, buffer, etc.

As already mentioned, the CD14 is a LPS receptor present on the membrane of macrophage, monocyte, Kupffer cells, and neutrophil. It is estimated that, when the cell is infected with a bacteria, the macrophage or the neutrophil is activated via CD14, to induce the generation of the inflammatory factor. Accordingly, the pharmaceutical compositions of the present invention comprising the oligonucleotide inhibiting the expression of the human CD14 as its active ingredient can be employed as a prophylactic/therapeutic agent against the disorders caused by the inflammatory factor generated through CD14 mediation. Exemplary such disorders include systemic inflammatory response syndrome, sepsis or endotoxinia, septic shock or endotoxin shock, ulcerative colitis, Crohn's disease, autoimmune response or disease, allergy disease, cancer, peritonitis, graft-versus-host reaction, periodontosis or osteoporosis. Since it is assumed that the present pharmaceutical composition more selectively effects on the CD14 on liver Kupffer cell, a high effect is expectable particularly as preventive or remedy against sepsis and septic shock, and constitutional symptom and organ insufficiency caused by the sepsis and septic shock.

Of the above disorders, the systemic inflammatory response syndrome (SIRS) is a condition triggered by bacteremia, trauma, burns, pancreatitis and operation invasion, and the grave SIRS lead to multiple organ dysfunction and multiple organ failure and to death. SIRS with implicit bacteria infection is sepsis, and the typical sepsis is endotoxemia. In addition to exogenous LPS invasion by trauma, burns, operation invasion, there are reported some cases, i.e. that the invasion of endogeneous LPS from enterobacterial fiord result from hyper permeability of intestinal mucosa (Ravin A., et al., Fed. Proc., Volume 21, page 65, 1962). For instance, there has been reported that, even if the infection is not recognized, reduced blood flow rate of mesenteric artery owing to shock after injury and collapse of the physiological barrier of the intestinal tract cause bacterial translocation, and hence, endotoxinia due to the endogenous LPS (Surgery, Volume 110, page 154, 1991). In all cases of hepatitis with significant liver dysfunction, such as alcoholic hepatitis, fulminating hepatitis or hepatocirrhosis, if endogenous LPS enters from intestine to portal vein without being sufficiently metabolized by liver Kupffer cells as the result of the liver dysfunction and the LPS further enters into systemic circulation, DIC and multiple organ failure may be induced to invite the death (Tanigawa Hisakazu, et al., Kan-Tan-Sui, Volume 27, page 381, 1993). In the case of burns injury, it has been reported that complication is induced at the lesion, and the increased plasma LPS level invites production of inflammatory cytokines such as TNF to result in diseased conditions (Endo Shige-atsu, et al., Burns, Volume 19, page 124, 1993). In the case of peritonitis, the major cause is infection with Gram-negative bacteria, but sometimes peritonitis are caused by enterobacterium. The graft-versus-host disease is a disorder most frequently occurs in bone marrow transplantation. It has been reported that, in the case of the graft-versus-host disease, transplanted lymphocyte attacks the host tissue, in particular, the digestive tract, and, LPS enters systemic circulation from the intestine to cause the endotoxemia (Moor K H., et al., Transplantation, Volume 44, page 249, 1987). Examples of grave diseases caused by endotoxemia include severe infectious diseases such as adult respiratory distress syndrome (ARDS), acute pyopoietic cholangeitis, pandemic peritonitis, postoperative celiac cystoma, etc.

When the oligonucleotide of the present invention is prepared in dosage forms as described above the administration method and the dosage may be adjusted depending on the patient's age, sex, type and seriousness of the disorder. In other words, the present oligonucleotides may be orally or parenterally administered in an amount suitable for adjustment of the CD14 expression level and improvement of disease condition. For example, 0.001 to 2000 mg/kg may be administered continuously or at one to several times at divided dose per one day. In the case of intravenous injection, a dose of 0.01 to 100 mg/kg is preferred. The present oligonucleotides are sufficiently safe in the dosage. The oral administration may be conducted by subglossal administration. The parenteral administration may be adequately selected aspiration, transdermal administration, collyrium, intravaginal administration, intra-articular administration, intrarectal administration, intra-artery administration, intravenous administration, topical administration, intramascular administration, subcutaneous administration, intraperitoneal administratoin and the like.

BEST MODE FOR CARRYING OUT THE INVENTION

Next, the present invention is more specifically illustrated by examples which are disclosed by way of examples and not by way of limiting the invention. Abbreviations used in the following description are abbreviations commonly used in the art. The examples were mainly conducted in accordance with Molecular Cloning, A Laboratory Manual 2nd ed. (Sambrook J., et al., Cold Spring Harbor Laboratory, 1989), which is hereby incorporated by reference.

The present invention is hereinafter described in further detail by the examples as described below.

EXAMPLE 1

Cloning of Human CD14 Gene

THP-1 cells were inoculated in a 2 well and a 6 well plates at $7.1 \times 10^5$ cells/well, incubated at 37° C. for one day. 1α,25-Dihydroxyvitamin $D_3$ (manufactured by BIOMOL Research) was added to the well to a final concentration of 0.1 μM, and the cells were further cultured for one day. The THP-1 cells were collected, and RNA was extracted from the collected cells using 1 ml of ISOGEN (manufactured by TELTEST) in accordance with the protocol. Subsequently, a cDNA library was constructed by Superscript Preamplification System (manufactured by GIBCO) using the extracted RNA using oligo dT primers as the template.

PCR was carried out using 1.5 μg of the thus prepared cDNA library, sense primer (5' ACGCGTCGAC GAGTTCACAA GTGTGAAGCC TG 3': SEQ.ID. No. 5), antisense primer (5' ACATGCATGC TTAATAAAGG TGGGGCAAAG GG 3': SEQ.ID. No. 6), and Pfu DNA synthetic enzyme (manufactured by Stratagene), and repeating 30 cycles of 94° C. for 30 seconds, 55° C. for 30 seconds, and 72° C. for 180 seconds. The thus amplified DNA fragment and pUC118 plasmid were digested with SalI restriction enzyme and SphI restriction enzyme, respectively, and purified by 1% agarose gel electrophoresis. Subsequently, DNA fragment digested from pUC118 and the PCR product were mixed at a proportion of 2:1, and ligated using Ligation kit (manufactured by Takara). Subsequently, this reaction mixture was transfected in JM109 cell, inoculated on agar plate, and incubated at 37° C. overnight. The generated colonies were collected and checked by PCR to confirm that the desired recombinant clone (pUCH14P-4 plasmid) was obtained.

EXAMPLE 2

Construction of the Plasmid for Expression of the Human CD14/Luciferase Fusion Protein In order to obtain an expression vector necessary for the synthesis of RNA for use in vitro translation, DNA fragment cleaved at HindIII and BamHI sites of pUCH14P-4 plasmid was inserted in an expression vector (pGEMluc plasmid), and cloned to obtain pGEMlucH14-9. Subsequently, PCR was carried out using pGEMlucH14-9 plasmid as the template, as well as sense primer (5' CCCAAGCTTA AGTGTGAAGC CTGAAGCCGC CGG 3': SEQ. ID. No. 7) and antisense primer (5' ATGGCGCCGG GCCTTTCTTT ATGTTTTTGG CGTCTTCCAG TTGG 3': SEQ. ID. No.8).

The reaction product was precipitated with ethanol, and digested with BbeI restriction enzyme and HindIII restriction enzyme, respectively. The PCR product was ligated with the DNA fragment of pGEMluc preliminarily digested with the BbeI and the HindIII by the conventional manner, and cloned by using HB101 cell to obtain pGEMluc(ctg) H14-3.

EXAMPLE 3

Synthesis of Oligonucleotides

Phosphodiester oligonucleotides and phosphorothioate oligonucleotides purified on OPC column obtained from Sawady Technology were employed in the following examples. Phosphorothioate oligonucleotides employed in Examples 10 and 11 purified with micro bondasphere C8 (300 Å) were obtained from Nisshinbô. Oligonucleotides complementary to human CD14 and oligonucleotides complementary to mouse CD14 are listed in Tables 1, 2, 3, 5 and 6. In Tables 1, 2, 3, 5 and 6, P=S stands for substitution of one oxygen atom (O) in phosphodiester linkage with a sulphur atom (S), and P=O stands for no substitution.

A mixture of random-sequence phosphodiester oligonucleotides or a mixture of random-sequence phosphorothioate oligonucleotides made by sequence-undefined random DNA synthesis using a mixture of four types of amidites, were used for the control oligonucleotide in the following examples.

Oligonucleotides complementary to the gene encoding human CD14 (part 1)

TABLE 1-1

| oligonucleotide | sequence | base length | modification | SEQ. ID. No. |
|---|---|---|---|---|
| SH0013A | CGGCTTCCAGGCTTCACACT | 20mer | P=S | 9 |
| SH0023A | CGGCACCCGGCGGCTTCCAG | 20mer | P=S | 10 |
| SH0033A | TCCTACACAGCGGCACCCGG | 20mer | P=S | 11 |
| SH0038A | TTCTTTGCTACACAGCGGCA | 20mer | P=S | 12 |
| SH0043A | TTAGCTTCTTTCCTACACAG | 20mer | P=S | 13 |
| SH0048A | GTGCTTTAGCTTCTTTCCTA | 20mer | P=S | 14 |
| SH0053A | TGGAAGTGCTTTAGCTTCTT | 20mer | P=S | 15 |
| SH0063A | GGACAGGCTCTGGAAGTGCT | 20mer | P=S | 16 |
| SH0073A | TCTGAGCTCCGGACAGGCTC | 20mer | P=S | 17 |
| SH0083A | CTTCCGAACCTCTGAGCTCC | 20mer | P=S | 18 |
| SH0093A | GTCGATAAGTCTTCCGAACC | 20mer | P=S | 19 |
| SH0096A | ATGGTCGATAAGTCTTCCGA | 20mer | P=S | 20 |
| SH0099A | TCCATGGTCGATAAGTCTTC | 20mer | P=S | 21 |
| SH0102A | CGCTCCATGGTCGATAAGTC | 20mer | P=S | 22 |
| SH0104A | CGCGCTCCATGGTCGATAAG | 20mer | P=S | 23 |
| SH0105A | GCGCGCTCCATGGTCGATAA | 20mer | P=S | 24 |
| SH0106A | CGCGCGCTCCATGGTCGATA | 20mer | P=S | 25 |
| SH0107A | ACGCGCGCTCCATGGTCGAT | 20mer | P=S | 26 |
| SH0108A | GACGCGCGCTCCATGGTCGA | 20mer | P=S | 27 |
| SH0109A | GGACGCGCGCTCCATGGTCG | 20mer | P=S | 28 |
| SH0112A | GCAGGACGCGCGCTCCATGG | 20mer | P=S | 29 |
| SH0114A | AAGCAGGACGCGCGCTCCAT | 20mer | P=S | 30 |
| SH0116A | ACAAGCAGGACGCGCGCTCC | 20mer | P=S | 31 |

Oligonucleotides complementary to the gene encoding human CD14 (part 2)

TABLE 1-2

| oligonucleotide | sequence | base length | modification | SEQ. ID. No. |
|---|---|---|---|---|
| SH0117A | AACAAGCAGGACGCGCGCTC | 20mer | P=S | 32 |
| SH0118A | CAACAAGCAGGACGCGCGCT | 20mer | P=S | 33 |
| SH0120A | AGCAACAAGCAGGACGCGCG | 20mer | P=S | 34 |
| SH0122A | GCAGCAACAAGCAGGACGCG | 20mer | P=S | 35 |
| SH0124A | CAGCAGCAACAAGCAGGACG | 20mer | P=S | 36 |
| SH0126A | AGCAGCAGCAACAAGCAGGA | 20mer | P=S | 37 |
| SH1231A | TCTTGGATCTTAGGCAAAGC | 20mer | P=S | 38 |
| SH1241A | CATTATTCTGTCTTGGATCT | 20mer | P=S | 39 |
| SH1256A | CAGTTTGAGTCCATTCATTA | 20mer | P=S | 40 |
| SH1259A | AGGCAGTTTGAGTCCATTCA | 20mer | P=S | 41 |
| SH1261A | CAAGGCAGTTTGAGTCCATT | 20mer | P=S | 42 |
| SH1262A | CCAAGGCAGTTTGAGTCCAT | 20mer | P=S | 43 |
| SH1263A | GCCAAGGCAGTTTGAGTCCA | 20mer | P=S | 44 |
| SH1264A | AGCCAAGGCAGTTTGAGTCC | 20mer | P=S | 45 |
| SH1265A | AAGCCAAGGCAGTTTGAGTC | 20mer | P=S | 46 |
| SH1266A | GAAGCCAAGGCAGTTTGAGT | 20mer | P=S | 47 |
| SH1267A | TGAAGCCAAGGCAGTTTGAG | 20mer | P=S | 48 |
| SH1268A | CTGAAGCCAAGGCAGTTTGA | 20mer | P=S | 49 |
| SH1269A | CCTGAAGCCAAGGCAGTTTG | 20mer | P=S | 50 |
| SH1270A | CCCTGAAGCCAAGGCAGTTT | 20mer | P=S | 51 |
| SH1271A | CCCCTGAAGCCAAGGCAGTT | 20mer | P=S | 52 |
| SH1273A | CTCCCCTGAAGCCAAGGCAG | 20mer | P=S | 53 |
| SH1276A | CGACTCCCCTGAAGCCAAGG | 20mer | P=S | 54 |
| SH1281A | TGACGGGACTCCCCTGAAGC | 20mer | P=S | 55 |

Oligonucleotides complementary to the gene encoding human CD14 (part 3)

TABLE 1-3

| oligonucleotide | sequence | base length | modification | SEQ. ID. No. |
|---|---|---|---|---|
| SH1291A | CTCAACGTCCTGACGGGACT | 20mer | P=S | 56 |
| SH1301A | TCGAAAAGTCCTCAACGTCC | 20mer | P=S | 57 |
| SH1311A | GTTGAATTGGTCGAAAAGTC | 20mer | P=S | 58 |
| SH1331A | TAATAAAGGTGGGCAAAGG | 20mer | P=S | 59 |
| OH0013A | CGGCTTCCAGGCTTCACACT | 20mer | P=O | 60 |
| OH0023A | CGGCACCCGGCGGCTTCCAG | 20mer | P=O | 61 |
| OH0033A | TCCTACACAGCGGCACCCGG | 20mer | P=O | 62 |
| OH0043A | TTAGCTTCTTTCCTACACAG | 20mer | P=O | 63 |

TABLE 1-3-continued

| oligonucleotide | sequence | base length | modification | SEQ. ID. No. |
|---|---|---|---|---|
| OH0053A | TGGAAGTGCTTTAGCTTCTT | 20mer | P=O | 64 |
| OH0063A | GGACAGGCTCTGGAAGTGCT | 20mer | P=O | 65 |
| OH0073A | TCTGAGCTCCGGACAGGCTC | 20mer | P=O | 66 |
| OH0083A | CTTCCGAACCTCTGAGCTCC | 20mer | P=O | 67 |
| OH0092A | GTCGATAAGTCTTCCGAACC | 20mer | P=O | 68 |
| OH0096A | ATGGTCGATAAGTCTTCCGA | 20mer | P=O | 69 |
| OH0099A | TCCATGGTCGATAAGTCTTC | 20mer | P=O | 70 |
| OH0102A | CGCTCCATGGTCGATAAGTC | 20mer | P=O | 71 |
| OH0103A | GCGCTCCATGGTCGATAAGT | 20mer | P=O | 72 |
| OH0104A | CGCGCTCCATGGTCGATAAG | 20mer | P=O | 73 |

TABLE 1-3-continued

| oligonucleotide | sequence | base length | modification | SEQ. ID. No. |
|---|---|---|---|---|
| OH0105A | GCGCGCTCCATGGTCGATAA | 20mer | P=O | 74 |
| OH0106A | CGCGCGCTCCATGGTCGATA | 20mer | P=O | 75 |
| OH0107A | ACGCGCGCTCCATGGTCGAT | 20mer | P=O | 76 |
| OH0108A | GACGCGCGCTCCATGGTCGA | 20mer | P=O | 77 |
| OH0109A | GCACGCGCGCTCCATGGTCG | 20mer | P=O | 78 |
| OH0110A | AGGACGCGCGCTCCATGGTC | 20mer | P=O | 79 |

Oligonucleotides complementary to the gene encoding human CD14 (part 4)

TABLE 1-4

| Oligonucleotide | sequence | base length | modification | SEQ. ID. No. |
|---|---|---|---|---|
| OH0111A | CAGGACGCGCGCTCCATGGT | 20mer | P=O | 80 |
| OH0112A | GCAGGACGCGCGCTCCATGG | 20mer | P=O | 81 |
| OH0113A | AGCAGGACGCGCGCTCCATG | 20mer | P=O | 82 |
| OH0114A | AAGCAGGACGCGCGCTCCAT | 20mer | P=O | 83 |
| OH0118A | CAACAAGCAGGACGCGCGCT | 20mer | P=O | 84 |
| OH0102A-15mer | CATGGTCGATAAGTC | 15mer | P=O | 85 |
| OH0102A-18mer | CTCCATGGTCGATAAGTC | 18mer | P=O | 86 |
| OH0102A-19mer | GCTCCATGGTCGATAAGTC | 19mer | P=O | 87 |
| OH0102A | CGCTCCATGGTCGATAAGTC | 20mer | P=O | 71 |
| OH0102A-21mer | GCGCTCCATGGTCGATAAGTC | 21mer | P=O | 88 |
| OH0102A-22mer | CGCGCTCCATGGTCGATAAGTC | 22mer | P=O | 89 |
| OH0102A-25mer | ACGCGCGCTCCATGGTCGATAAGTC | 25mer | P=O | 90 |
| OH0102A-30mer | GCAGGACGCGCGCTCCATGGTCGATAAGTC | 30mer | P=O | 224 |

Oligonucleotides complementary to the gene encoding mouse CD14

TABLE 2

| Oligonucleotide | sequence | base length | modification | SEQ. ID. No. |
|---|---|---|---|---|
| SM0097A | CATGGTCGGTAGATTCTGAA | 20mer | P=S | 91 |
| SM0101-0220A | CACACGCTCCATGGTCGGTAGATTC | 25mer | P=S | 92 |
| SM0102A-25mer | GCACACGCTCCATGGTCGGTAGATT | 25mer | P=S | 93 |
| SM0103A-25mer | AGCACACGCTCCATGGTCGGTAGAT | 25mer | P=S | 94 |
| SM0104A-25mer | AAGCACACGCTCCATGGTCGGTAGA | 25mer | P=S | 95 |

TABLE 2-continued

| Oligonucleotide | sequence | base length | modification | SEQ. ID. No. |
|---|---|---|---|---|
| SM0105A-25mer | CAAGCACACGCTCCATGGTCGGTAG | 25mer | P=S | 96 |
| SM0106A-25mer | CCAAGCACACGCTCCATGGTCGGTA | 25mer | P=S | 97 |
| SM0107-0226A-25mer | GCCAAGCACACGCTCCATGGTCGGT | 25mer | P=S | 98 |
| SM0109-25mer | AAGCCAAGCACACGCTCCATGGTCG | 25mer | P=S | 99 |
| SM0111-25mer | ACAAGCCAAGCACACGCTCCATGGT | 25mer | P=S | 100 |
| SM0105A-21mer | CACACGCTCCATGGTCGGTAG | 21mer | P=S | 258 |

EXAMPLE 4

Synthesis of Human CD14 RNA

In vitro transcription reaction was conducted using Ribo max system (manufactured by Promega) in accordance with the attached protocol. pGEMluc(ctg)H14-3 plasmid was digested with XhoI, and blunted with Klenow fragment. Subsequently, in vitro transcription was performed employing 20 µg of this pGEMluc(ctg)H14-3 for the template, and SP6 polymerase in the presence of 7-methyl guanine and incubating the mixture at 37° C. for 4 hours. The reaction product was treated with DNase, and extracted with phenol. The reaction mixture was subjected to ethanol precipitation, and the resulting RNA pellets were dried in air, and dissolved in distilled water. By denaturing agarose gel electrophoresis the thus synthesized RNA was confirmed to be a single band of 1.4 kb.

EXAMPLE 5

Detection of the Inhibitory Activities for CD14 Translation by Oligonucleotide Complementary to Human Non-coding Region In vitro transcription reaction was performed using Rabbit Reticulocyte Lysate System (manufactured by Promega) in accordance with the attached protocol. More specifically, synthesized RNA from pGEMluc(ctg)H14-3 and unmodified oligonucleotides to be tested were mixed at a ratio of 1:10, and heated at 60° C. for 2 minutes. Subsequently, amino acids, and Rabbit Reticulocyte Lysate were added to the mixture, and the mixture was incubated at 30° C. for 2 hours. 10 µl of reaction mixture and an equivalent amount of luminous substrate solution (luciferase assay system, manufactured by Promega) were mixed, and allowed to react at room temperature for 5 seconds, the luminous intensity of the reaction solution was measured by a luminescence meter (Lumat LB96P). The results are shown in FIG. 1. The inhibitory activity of the oligonucleotides was calculated by assuming the fluorescent amount of the control oligonucleotide (20mer phosphodiester oligonucleotide having a random sequence) in the treatment as 100%. The sequences exhibiting at least 30% inhibitory activity were OH0013A, OH0023A, OH0033A, OH0043A, OH0053A, OH0099A, OH0102A, OH0103A, OH0104A, OH0105A, OH0106A, OH0107A, OH0108A, OH0109A, OH0110A, OH0112A and OH0114A. In particular, the antisense oligonucleotides near the translational initiation site showed high inhibitory activity.

EXAMPLE 6

Figure 2:
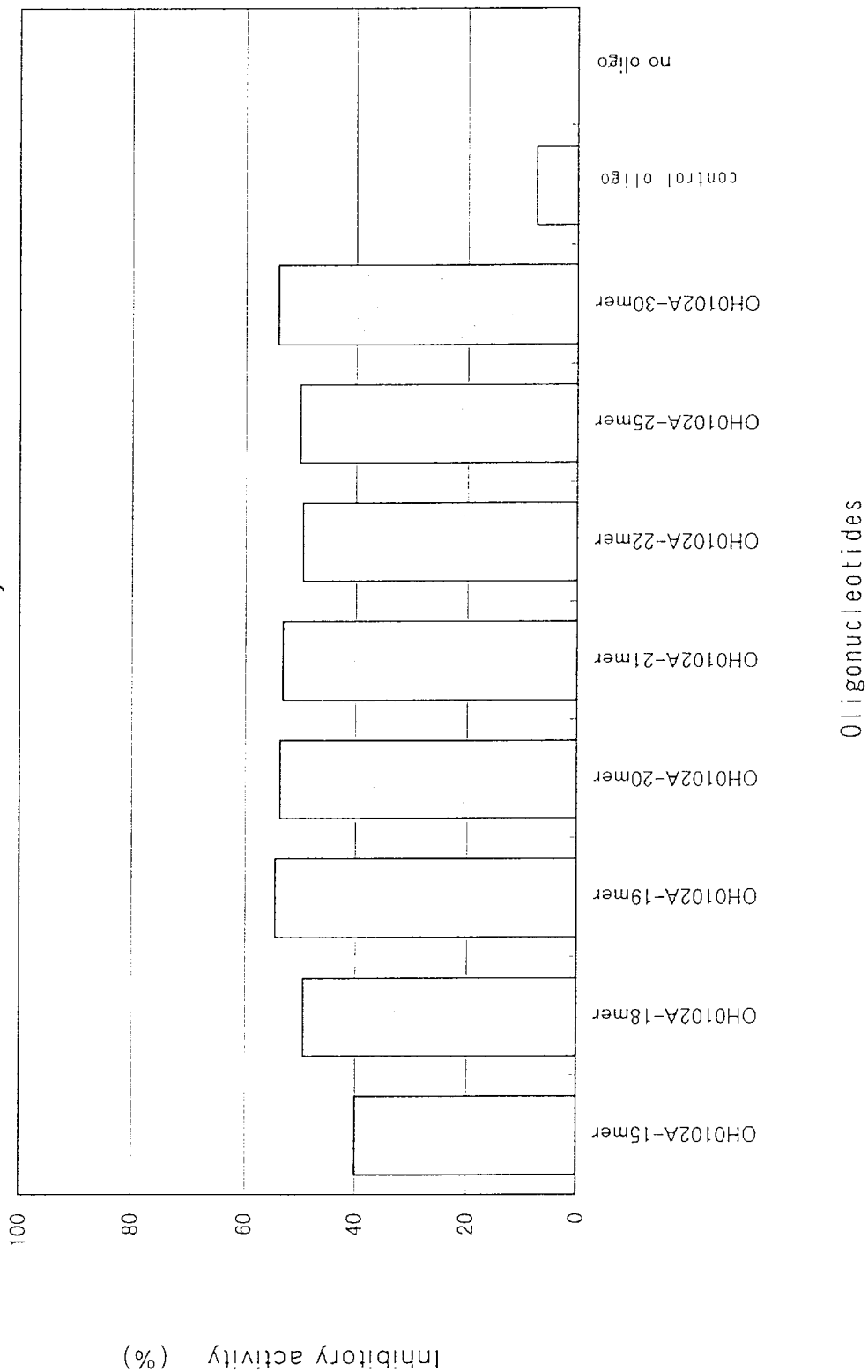
FIG. 2: A graph indicating the effects of the nucleotide length of the antisense oligonucleotides complementary to a gene encoding human CD14.

The Inhibitory Activities for CD14 Translation by Oligonucleotides of Different Length 8 types of antisense oligonucleotides with different lengths (OH0102A-15mer, OH0102A-18mer, OH0102A-19mer, OH0102A, OH0102A-21mer, OH0102A-22mer, OH0102A-25mer, and OH0102A-30mer, having nucleotide lengths of 15mer, 18mer, 19mer, 20mer, 21mer, 22mer, 25mer and 30mer, respectively) and the control oligonucleotide were tested, and the activity of the translation arrest was evaluated in the manner of Example 5. It was then found that the inhibitory activity in the translation was detected in all nucleotides independent on the nucleotide length (FIG. 2).

EXAMPLE 7

Measurement of the Inhibitory Activities for Human TNFα Production (5' Non-coding Region and Neighbor Region of Translation Initiational Site)

THP-1 cells were suspended in RPMI1640 medium containing 10% inactivated fetal bovine serum, inoculated at $1 \times 10^5$ cells/well into the 24 well plates, and cultured in the presence of 10 ng/ml of Phorbol 12-Myristate 13-Acetate (manufactured by SIGMA) for 24 hours. After exchanging the medium, the oligonucleotides were added to a final concentration of 100 nM. After incubating for 4 hours, the culture supernatant was removed and the cells were washed. The cells were again cultured in a RPMI1640 medium containing 10% inactivated fetal bovine serum in the presence of 40 ng/ml of 1α,25-Dihydroxyvitamin D3 (manufactured by BIOMOL Research) for 20 hours. After washing the cells, the medium were replaced with RPMI1640 containing 2% human serum to which 1 ng/ml of lipopolysuccharide (E. coli 055: B5, manufactured by Difco) has been added. After incubation for 4 hours, the culture supernatant was collected. TNFα in the culture supernatant was measured with human TNFα ELISA SYSTEM (manufactured by Amersham).

Figure 3:
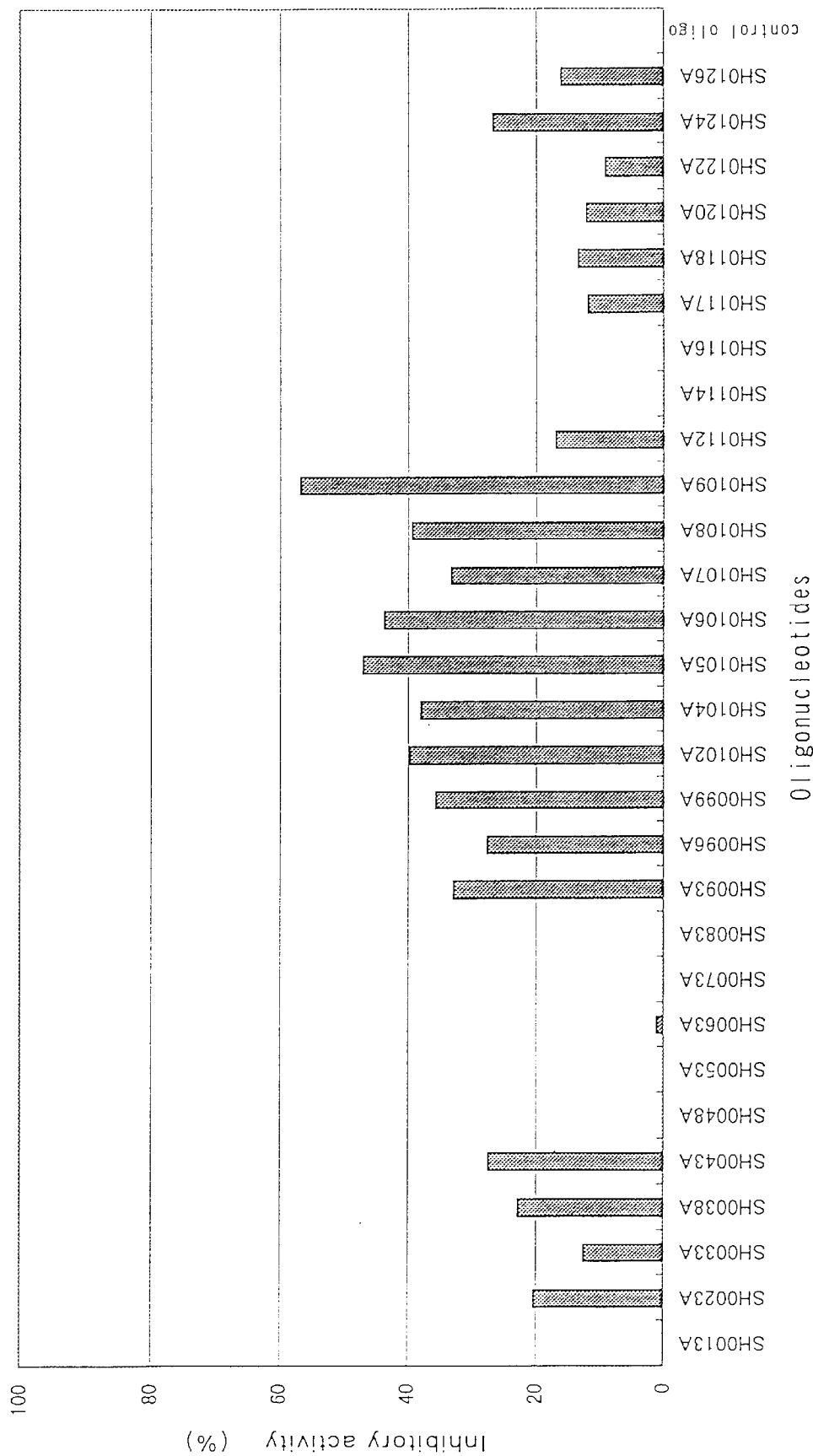
FIG. 3: A graph indicating human TNFα production-inhibitory activity of the antisense oligonucleotides complementary to 5' non-coding region and AUG neighboring region of mRNA of human CD14.

The measurement of TNFα was performed in accordance with protocol attached to the human TNFα ELISA SYSTEM. In other words, 50 µl of suitably diluted culture supernatant were transferred to a reaction plate, 50 µl of biotinylated antibody solution were added, and stood at room temperature for 2 hours. The reaction solution was removed, and wells were washed with 400 µl/well of wash buffer three times. 100 μl of suitably diluted streptavidin-peroxidose conjugate were added, and the mixture was further left to stand for 30 minutes. After washing, 100 μl of chromogenic solution were added, and reacted for 15 minutes. 100 μl of stop solution were added to terminate the reaction, and absorbance at 450 nm was measured in order to calculate the TNFα value in the sample. FIG. 3 indicates the results.

Inhibitory activity in the TNFα production was detected in SH0023A, SH0033A, SH0038A, SH0043A, SH0063A, SH0093A, SH0096A, SH0099A, SH0102A, SH0104A, SH0105A, SH0106A, SH0107A, SH0108A, SH0109A, SH0112A, SH0117A, SH0118A, SH0120A, SH0122A, SH0124A and SH0126A. The results showed good correlation with the results of the oligonucleotides of Example 4 which showed inhibitory activity for translation.

It was found that, when roughly categorized, the active sequences were complementary to three regions which are in the 5' non-coding region and the regions in the neighbor of the translation initiation site. The active region 1 was indicated by the oligonucleotides which complementarily bound to a part of the sequence CUGGAAGCCGC-CGGGUGCCGCUGUGUAGGAAAGAAGCUAAA (SEQ ID NO: 270). The active region 2 was indicated by the oligonucleotides which complementarily bound to a part of the sequence GGUUCGGAAGACUUAUCGACCAUG-GAGCGCGCGUCCUGC (SEQ ID NO: 271). The active region 3 overlapped with the active region 2, and the active regions were indicated by the oligonucleotides which complementarily bound to a part of the sequence GAGCGCGCGUCCUGCUUGUUGCUGCUGCU (SEQ ID NO: 272).

EXAMPLE 8

Measurement of the Inhibitory Activities in Human TNFα Production (3' Non-coding Region)

Figure 4:
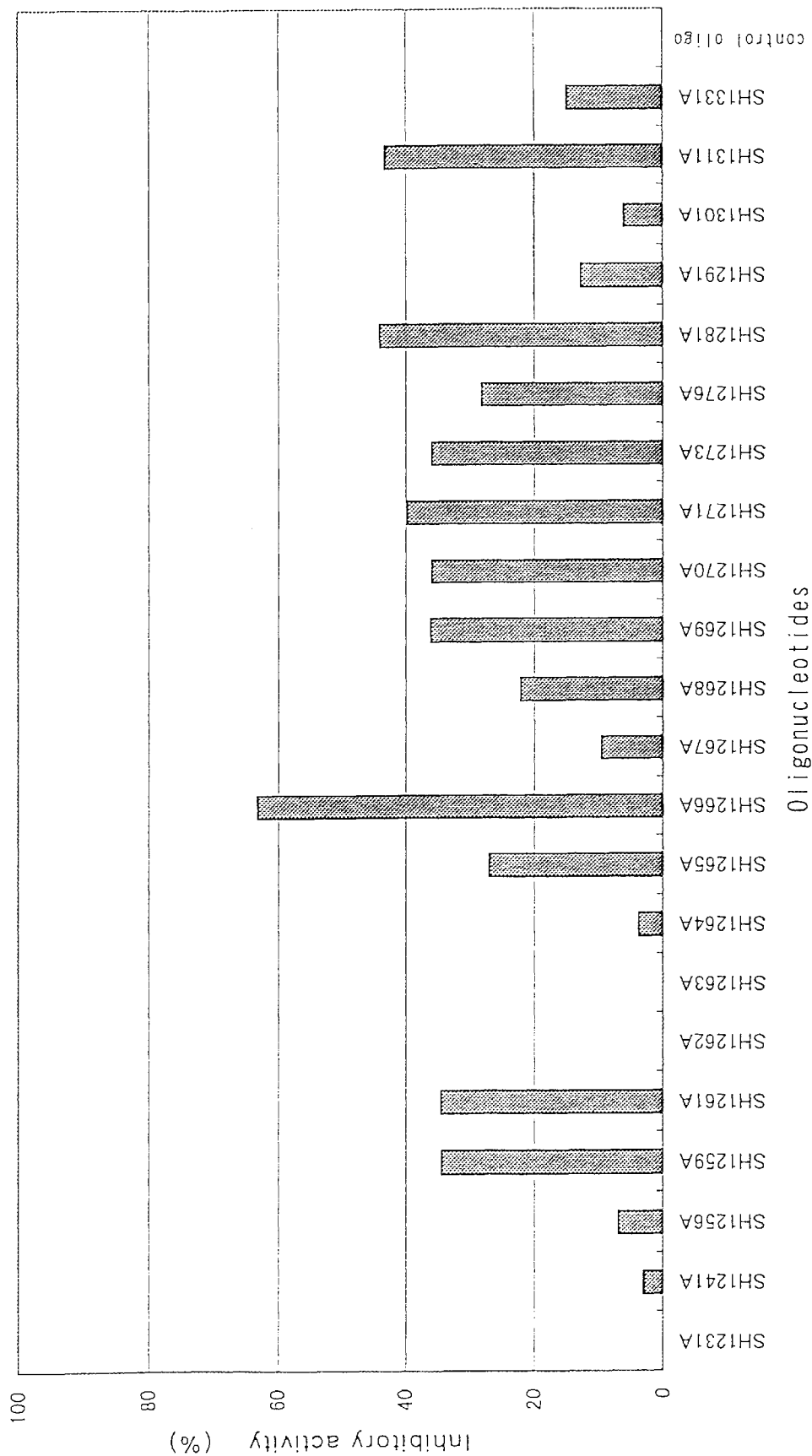
FIG. 4: A graph indicating human TNFα production-inhibitory activity of the antisense oligonucleotides complementary to 3' non-coding region of mRNA of human CD14.

Inhibitory activity for TNFα production by oligonucleotides complementary to the 3' non-coding region of human CD14 mRNA was evaluated in the same manner as Example 7. The results of the experiments are shown in FIG. 4.

Inhibitory activity for TNFα production was detected in SH1241A, SH1256A, SH1259A, SH1261A, SH1264A, SH1265A, SH1266A, SH1267A, SH1268A, SH1269A, SH1270A, SH1271A, SH1273A, SH1276A, SH1281A, SH1291A, SH1301A, SH1311A and SH1331A. It was found that the active sequences were complementary to roughly four regions. The active region 4 was indicated by the oligonucleotides which complementarily bound to a part of AGAUCCAAGACAGAAUAAUGAAUGGACU-CAAACUGCCUUG (SEQ ID NO: 273). The active region 5 was indicated by the oligonucleotides which complementarily bound to a part of GGACUCAAACUGCCUUG-GCUU (SEQ ID NO: 274). The active region 6 overlapped with the active region 5, and these regions were indicated by the oligonucleotides which complementarily bound to a part of the sequence CUCAAACUGCCUUGGCUUCAGGG-GAGUCCCGUCAGGACGUUGAGGACUUUUCGA (SEQ ID NO: 275). The active region 7 was indicated by the oligonucleqtides which complementarily bound to a part of GGACGUUGAGGACUUUUCGACCAAUU-CAACCCUUUGCCCCACCUUUAUUA (SEQ ID NO: 276)

EXAMPLE 9

The Measurement of Inhibitory Activities for Mouse TNFα Production (5' Non-coding Region and the Neighbor Region of the Translational Initiation Site)

J774A.1 cells were suspended in DMEM medium containing 10% inactivated fetal bovine serum, inoculated in the 24 well plate at $0.5 \times 10^5$ cells/well, and cultivated for 24 hours. After exchanging the medium, the oligonucleotides were added to the culture medium to a final concentration of 100 nM. After incubating for 4 hours, the culture supernatant was removed, and the cells were washed. Then cells were again cultured in RPMI1640 medium containing 10% inactivated fetal bovine serum for 20 hours. After washing the cells, the medium was substituted with DMEM containing 2% mouse serum to which lipopolysuccharide (LPS) (E. coli 0111: B4, manufactured by DIFCO) was added to a final concentration of 100 ng/ml. After incubating for 4 hours, the culture supernatant was collected. TNFα in the culture supernatant was measured with mouse TNFα ELISA SYSTEM (manufactured by Amersham).

Figure 5:
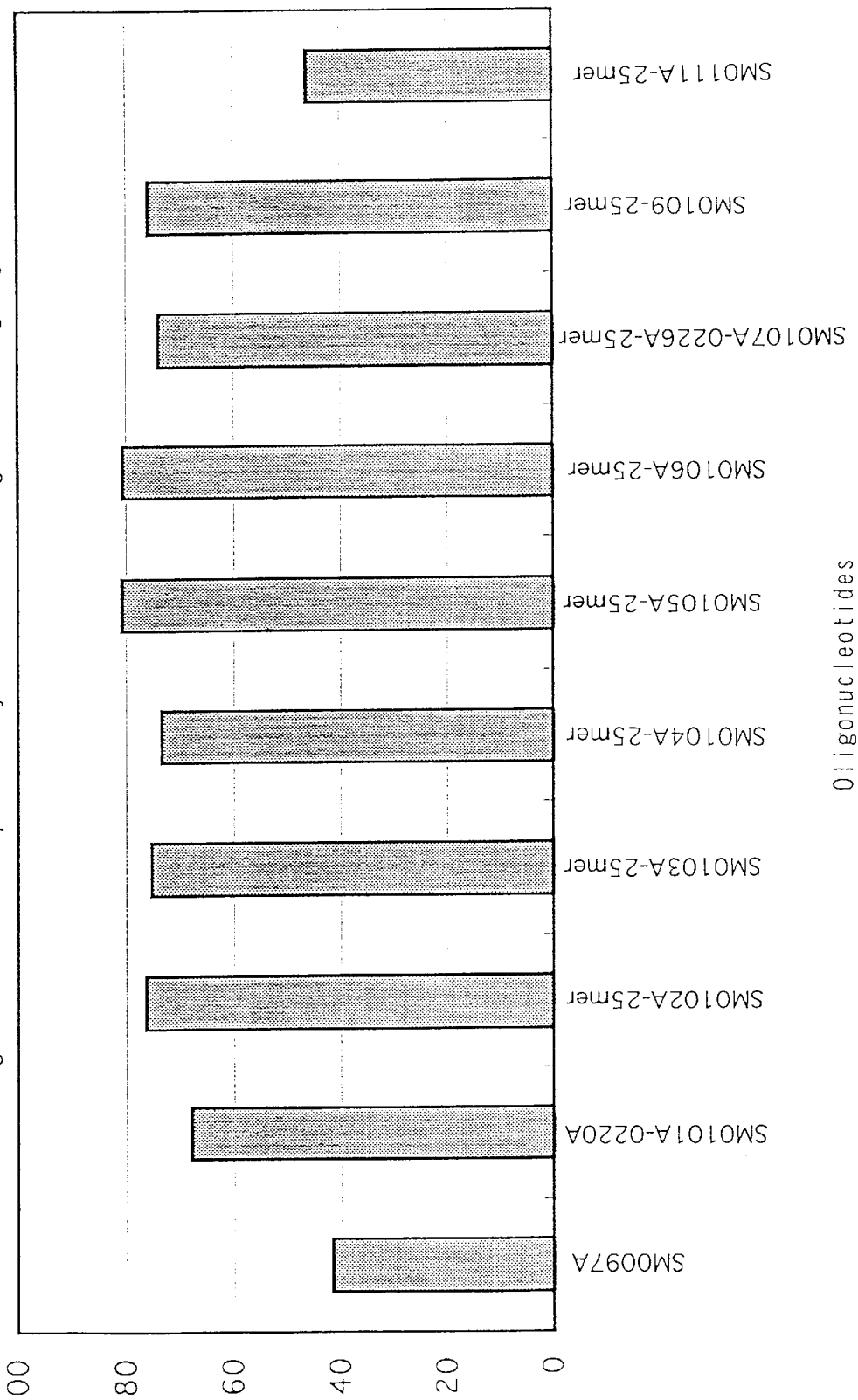
FIG. 5: A graph indicating mouse TNFα production-inhibitory activity of the antisense oligonucleotides complementary to 5' non-coding region and AUG neighbouring region of mRNA of mouse CD14.

The measurement of TNFα was carried out in accordance with protocol attached to mouse TNFα ELISA SYSTEM. In other words, 50 μl of suitably diluted culture supernatant were transferred to a reaction plate, 50 μl of biotinylated antibody solution were added, and left to stand at room temperature for 2 hours. The reaction solution was removed, wells were washed with wash buffer fluid of 400 μl/well three times. 100 μl of suitably diluted streptavidin-peroxidase conjugate were added, and the mixture was further left to stand for 30 minutes. After washing, 100 μl of chromogenic solution were added, and reacted for 15 minutes. 100 μl of stop solution were added to terminate the reaction, and absorbance at 450 nm was measured in order to calculate the TNFα value in the sample. FIG. 5 indicates the results.

A high inhibitory activity for mouse TNFα production was detected in the antisense compounds having a sequence complementary to the neighbor region of the mouse CD14 mRNA translation initiation site, e.g. SM0101-0220A, SM0102A-25mer, SM0103A-25mer, SM0104A-25mer, SM0105A-25mer, SM0106A-25mer, SM0107-0226A-25mer and SM0109-25mer.

EXAMPLE 10

Effect of SM0105A in Mouse Shock Model

Antisense oligonucleotide SM0105A-21mer to the gene encoding the mouse CD14 was used in the following experiments.

(1) Effect in Mortal Endotoxin Shock Model

Balb/c male mice at the age of 6 weeks (manufactured by Charles River Japan) were divided into 7 groups (each group consisting of 10 animals) based on body weight. The mouse was administered once from its tail vein. Subsequently, 3 mg/kg to 0.3 mg/kg of SM0105A oligonucleotide, 3 mg/kg to 0.3 mg/kg of control oligonucleotide (a 21mer phosphorothioate oligonucleotide having a random sequence), or 10 ml/kg of physiological saline (for negative control, manufactured by Ôtsuka).

At 24 hours after the administration of the test substance, 5 μg/kg of LPS (E. coli 055: B5, manufactured by Difco) and 700 mg/kg of galactosamine (D-Galactosamine hydrochloride, manufactured by Wakô) were administered to the mouse from its tail vein to induce shock. 0.3 mg/kg of methyl prednisolone was administered immediately before the LPS injection. The survival rate was continuously checked until 24 hours after the shock induction.

Figure 6:
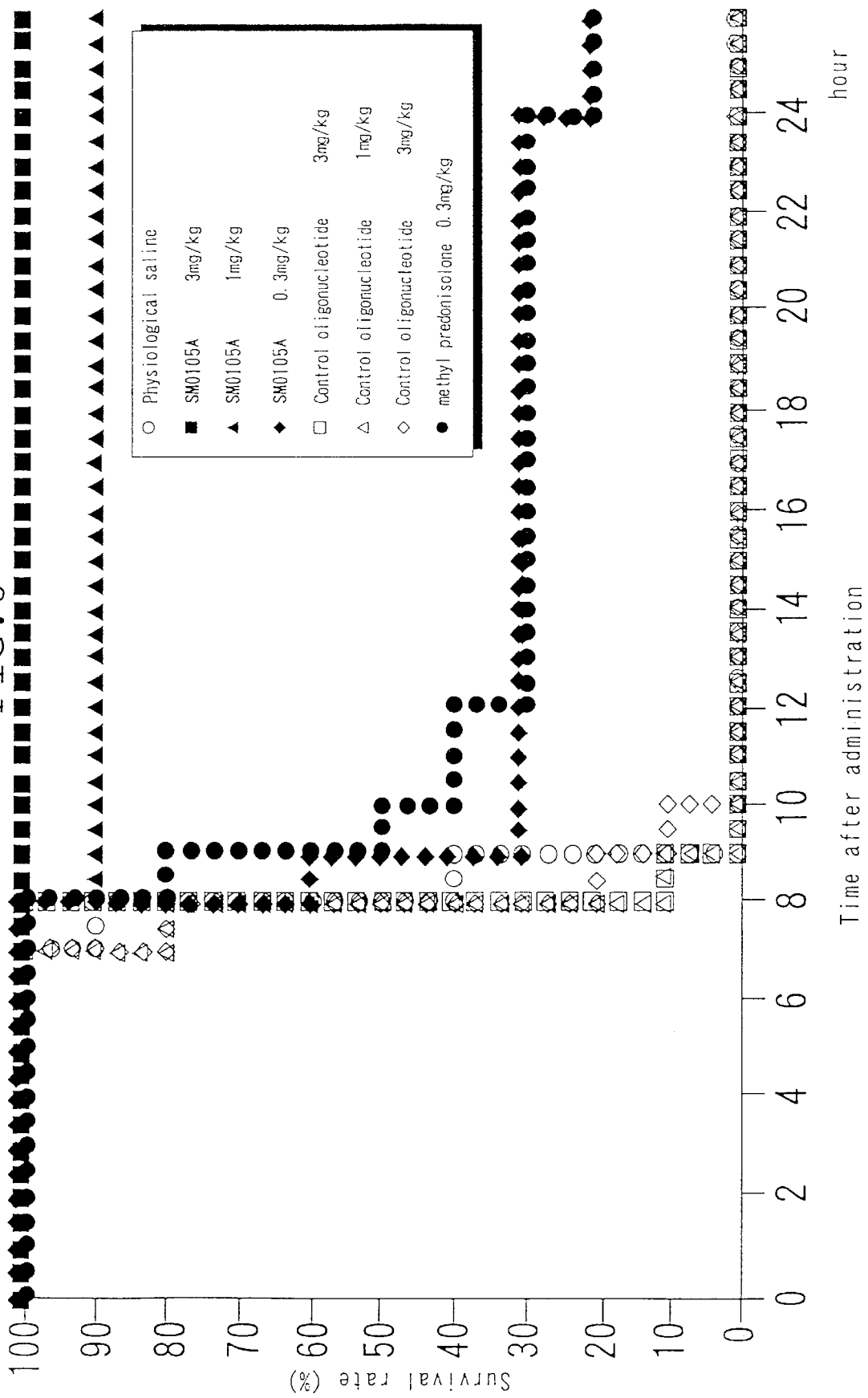
FIG. 6: A graph indicating the effect of oiligonucleotide SMO105A in endotoxin shock model.

FIG. 6 indicates the results. All animals of the group administered with the physiological saline as negative control group were dead 9 hours after the shock induction. All animals of the group administered with the control oligonucleotide were dead before 10 hours after the shock induction, irrespective of the dosage amount. On the other hand, in the group administered with the SM0105A oligonucleotide, all animals of the group administered with 3 mg/kg survived even after 24 hours, 9 animals of the group administered with 1 mg/kg survived, and 2 animals of the group administered with 0.3 mg/kg survived. Survival rate at the dosage of 0.3 mg/kg of SM0105A-administered was equivalent with the survival rate of the animal administered with the same amount of methyl prednisolone. Improvement of survival rate by SM0105A in dosage-dependent manner was confirmed from these results.

(2) Effect of SM0105A in Mortal Endotoxin Pre-shock Model

This evaluation was conducted in accordance with method of Matsumoto, T., et al. (FEMS Immunology and Medical Microbiology 17, 171–178 (1997)). 200 mg/kg of cyclophosphamide (hereinafter designated as "CPA") were administered to the tail vein of 6 weeks male Balb/c mice which had been freely water-fed and dieted. At 7 days after the CPA administeration, 5 mg of iota carrageenan (manufactured by Sigma) in physiological saline were intraperitonally administered. At 12 hours after the iota carrageenan injection, LPS (*E. coli* 127: B8, manufactured by Difco) was administered from the tail vein at the dosage of 30 µg/kg. At 1 hour and 24 hours after the LPS administration, 50 µl of blood was collected from eyeground vein using a glass capillary pretreated with heparin solution (1000 IU/ml)(manufactured by Mochida), and the blood was centrifuged to collect the plasma. GPT activity was determined using blood GPT activity measurement slide, GPT/ALT-P (manufactured by Fuji Film) and Fuji DRI-CHEM 5000 (manufactured by Fuji Film). Physiological saline (which was also used as the medium for the oligonucleotide), control oligonucleotide and SM0105A were administered at a dose of 10 ml/kg to the tail vein 24 hours before the LPS administration and water-soluble prednisolone was administered immediately before the LPS administration in the same manner.

Figure 7:
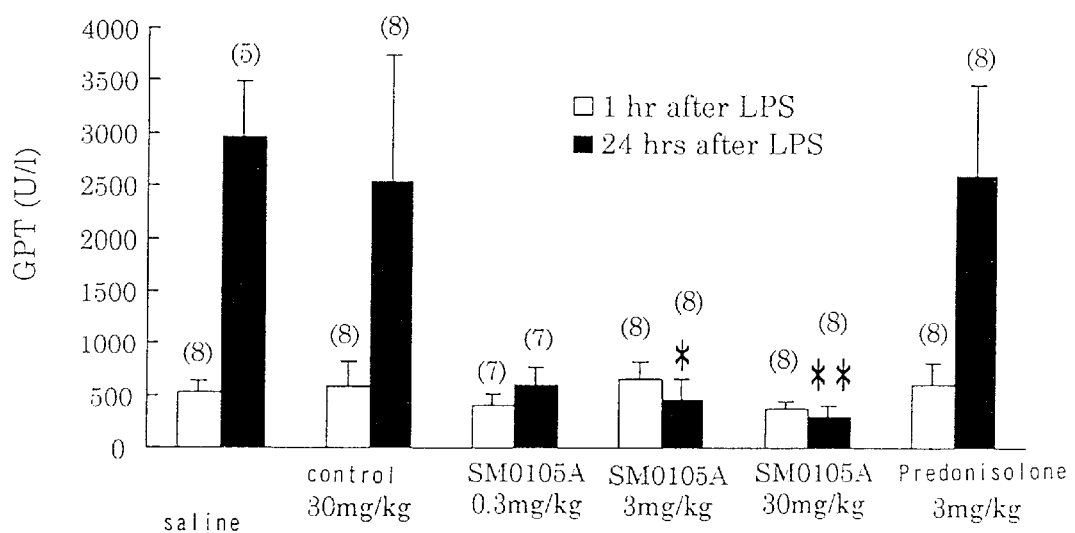
FIG. 7: A graph indicating the effect of oiligonucleotide SMO105A on liver function in endotoxin shock model.

As a consequence, in comparison with the 50% survival rate of the group administered with the physiological saline administration group, the group administered with the SM0105A or prednisolone exhibited 100% survival rate. Significant increase in GTP was suppressed in the liver of the animal administered with SM0105A, whereas such effect was not recognized in the animal administered with the prednisolone (FIG. 7).

EXAMPLE 11

Acute Toxicity in Mouse

The following experiment was carried out using SM105A-21mer.

Balb/c male mice (supplied by Charlse-Liver Japan) of 6 weeks old were divided into 2 groups (4 animals per group) by taking the body weight into considaration. Subsequently, SM0105A and control oligonucleotide (a 21mer phosphorothioate oligonucleotide having a random sequence) at a dose of 30 mg/kg, or 10 ml/kg of physiological saline (negative control, manufactured by Ôtsuka) was administered to the tail vein by single administration. The survival rate and the blood GOT value were measured until 7 days after the injection.

All animals were alive in both the groups administered with the physiological saline and the oligonucleotide. The blood GOT value was within the normal range and no significant difference was found between the groups.

EXAMPLE 12

Measurement of the Inhibitory Activities for the Expression of Human CD14/Luciferase Fusion Protein (1) Establishment of a HeLa Transformant Which Expresses Human CD14/Luciferase Fusion Protein In order to establish a HeLa transformant which is used for the inhibitory assay where human CD14/luciferase fusion protein expression is inhibited, a plasmid for expressing a human CD14/luciferase fusion protein (pM1651) was constructed. More specifically, the pGEMlucH14-9 prepared in Example 2 was digested with HindIII and XhoI, and the resulting DNA fragment was inserted in HindIII/XhoI site of pcDNA3.1(+) (manufactured by Invitrogen) by a conventional manner. pM1651 was obtained by cloning with JM109 cell.

The pM1651 was transfected in HeLa cell which is a cell derived from endocervix cancer, to establish a HeLa transformant expressing human CD14/luciferase fusion protein. More specifically, $5\times10^5$ of HeLa cells were inoculated in a dish of 100 mm diameter, cultured over night, and subsequently, the cells were transfected with 10 µg of pM1651 by calcium phosphate method. The cell was cultured in DMEM medium supplemented with 10% fetal bovine serum over night. The cells were seeded on a 96 well plate at 100 or 500 cells/well. From the next day, the transformants were selected in the medium containing G-418. Among the thus obtained G-418-resistant strains, Hel651d3-20 clone which exhibited luciferase activity was employed for the inhibitory assay wherein the expression of the fusion protein is inhibited by antisense oligonucleotides.

(2) Measurement of the Inhibitory Activity for the Expression of Human CD14/Luciferase Fusion Protein (5' Non-coding Region, Neighbor Region of Translational Initiation Site and 5'-coding Region)

Figure 8:
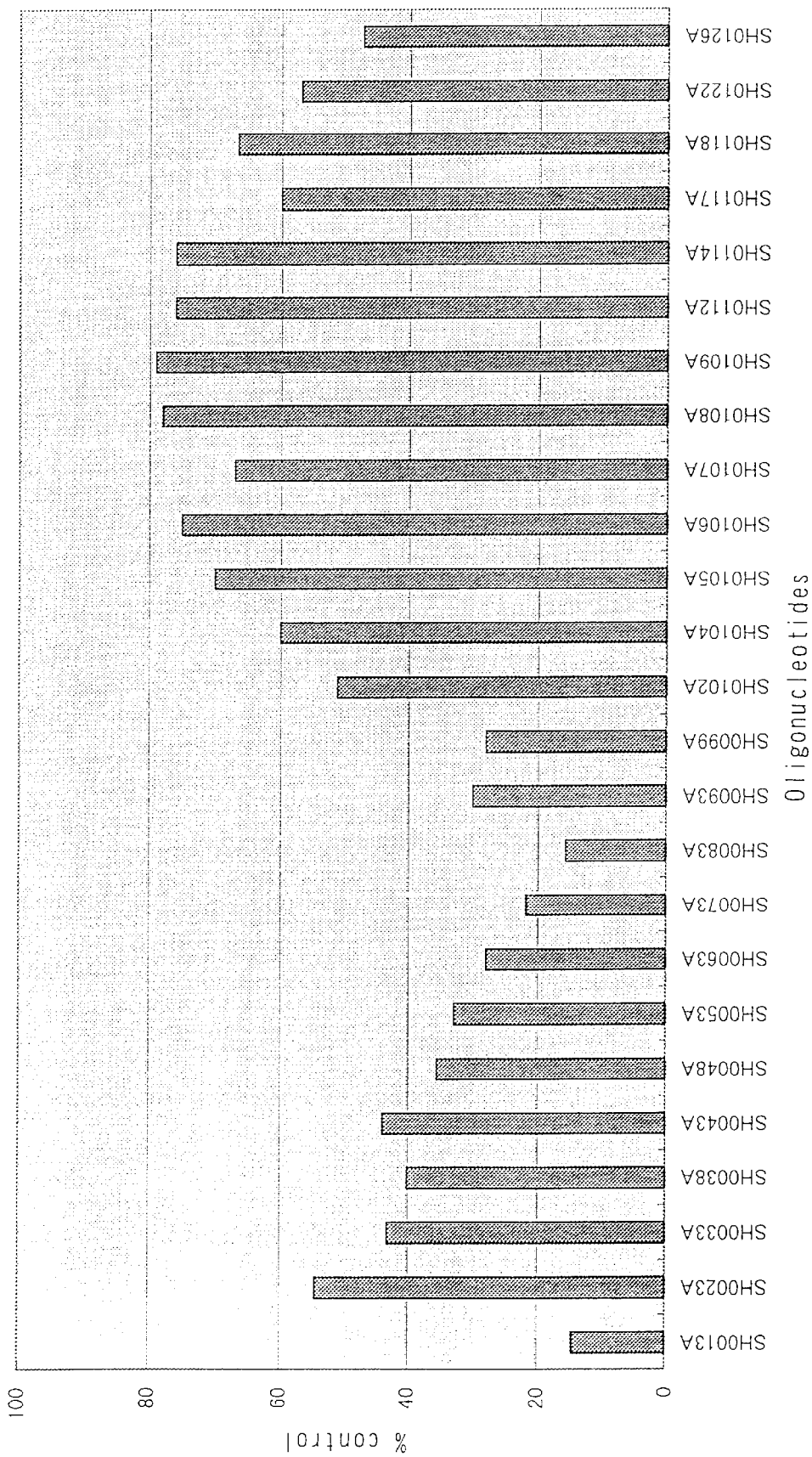
FIG. 8: A graph indicating the inhibitory activity of the antisense oligonucleotides to a gene encoding human CD14 to the expression of human CD14/luciferase fusion protein.

HeLa transformant (Hel65ld3-20) prepared in (1) were suspended in the DMEM medium supplemented with 10% fetal bovine serum and 0.6 mg/mL of G-418, and the cells were seeded into the 24 well plate at $1\times10^5$ cells/well, and cultured over night. The cells were washed with saline (manufactured by Ôtsuka) twice, and 450 µL/well of Opti-MEM medium (manufactured by Gibco BRL) were added to the well. Subsequently, lipofectin reagent and the oligonucleotide of SEQ. ID. Nos. 9, 10, 11, 12, 13, 14, 15, 16, 17, 18, 19, 21, 22, 23, 24, 25, 26, 27, 28, 29, 30, 32, 33, 35, or 37 were added to a final concentration 100 nM in accordance with the manual of Gibco BRL. The cells were incubated at 37° C. for 6 hours, the culture supernatant was removed, and the cells were washed. The cells were further cultured overnight in the DMEM medium supplemented with 10% fetal bovine serum and 0.6 mg/mL of G418. After washing the cells, the cells were lysed in Passive Lysis Buffer (manufactured by Promega). Employing 20 µL of the solution, the luciferase activity of the cell lysate was measured in accordance with the protocol of Promega. More specifically, the cell lysate and Luciferase Assay Reagent II (manufactured by Promega) were mixed in a plate for fluoroeschence measurement (manufactured by DYNEX; Microlite 2 plate) to initiate the reaction, and luminescence intensity for 10 seconds was determined. Luminometer manufactured by berthold (LB96P) was employed for the measurement. The inhibitory activity for protein expression of the oligonucleotides was calculated in relation to the luminescence intensity of the control sample without the oligonucleotide at 100%. FIG. 8 indicates the results. Antisense oligonucleotides exhibiting the inhibitory activity of at least 40% in 5' non-coding region were SH0023A, SH0033A, SH0038A and SH0043A. On the other hand, antisense oligonucleotides exhibiting at least 40% of inhibitory activity in the region containing translation initiation site were SH0102A, SH0104A, SH0105A, SH0106A, SH0107A, SH0108A, SH0109A, SH0112A, SH0114A, SH0117A, SH0118A, SH0122A and SH0126A. These results of the inhibitory activity for protein expression were well consistent with the results of inhibitory activity for CD14 translation by in vitro translation in Example 5.

EXAMPLE 13

Measurement of the Binding Activity of Antisense Oligonucleotide by RNase H Cleavage Test 2 μg of human CD14 RNA obtained in Example 4 and an unmodified oligonucleotide to be tested, which is the one listed in Table 3, were mixed at a molar ratio of 1:1, and 1 μl of RNaseH buffer of 5-fold concentration and a suitable amount of distilled water were added to prepare 4 μl of the mixture solution. This mixture was heated to 75° C., and cooled, and 0.05 U of RNaseH were added. The mixture was maintained at 37° C. for 15 minutes to promote the reaction. 10 μl of stop solution of 2-fold concentration (95% formamide, 0.5 mM EDTA with pH 8.0, 0.025% of SDS, 0.025% of Xylene Cyanol, 0.025% of BPB) were added to terminate the reaction. 4 μl of the sample were pre-treated at 65° C., and electrophoresed using 6 M urea-denatured 5% polyacrylamide gel (160 mm width, 330 mm height, 0.35 mm thickness) at 15 mA/plate. The band generated by staining with 5000-fold diluted SYBER Green II (manufactured by Wakô Pure Chemicals Industries ltd.) was measured with Fluor Imager SI (manufactured by Molecular Dynamics). The score of the binding activity was calculated by the following formula:

Binding value = (fluorescence value of sample oligonucleotide - fluorescence value of control oligonucleotide)/(fluorescence value of SH0102A - fluorescence value of control oligonucleotide)

| score | binding value |
|---|---|
| 0 | 0.5 > X |
| 1 | 0.9 > X ≧ 0.5 |
| 2 | 1.3 > X ≧ 0.9 |
| 3 | X ≧ 1.3 |

TABLE 3-1

| oligonu-cleotide | sequence | modification | base length | sequence ID No. |
|---|---|---|---|---|
| OH0083A-15mer | GAACCTCTGAGCTCC | P=O | 15mer | 101 |
| OH0102A-15mer | CATGGTCGATAAGTC | P=O | 15mer | 85 |
| OH0104A-15mer | TCCATGGTCGATAAG | P=O | 15mer | 102 |
| OH0114A-15mer | GGACGCGCGCTCCAT | P=O | 15mer | 103 |
| OH0134A-15mer | AGCAGCAGCAGCAAC | P=O | 15mer | 104 |
| OH0144A-15mer | CACCAGCGGCAGCAG | P=O | 15mer | 105 |
| OH0154A-15mer | CAGAGACGTGCACCA | P=O | 15mer | 106 |
| OH0164A-15mer | GGCGTGGTCGCAGAG | P=O | 15mer | 107 |
| OH0174A-15mer | ACAAGGTTCTGGCGT | P=O | 15mer | 108 |
| OH0184A-15mer | CGTCCAGCTCACAAG | P=O | 15mer | 109 |
| OH0194A-15mer | AAATCTTCATCGTCC | P=O | 15mer | 110 |
| OH0204A-15mer | GACGCAGCGGAAATC | P=O | 15mer | 111 |
| OH0214A-15mer | AGAAGTTGCAGACGC | P=O | 15mer | 112 |
| OH0224A-15mer | TGAGGTTCGGAGAAG | P=O | 15mer | 113 |
| OH0234A-15mer | CCAGTCGGGCTGAGG | P=O | 15mer | 114 |
| OH0244A-15mer | AGGCTTCGGACCAGT | P=O | 15mer | 115 |
| OH0254A-15mer | ACACACTGGAAGGCT | P=O | 15mer | 116 |
| OH0264A-15mer | TACTGCAGACACACA | P=O | 15mer | 117 |
| OH0274A-15mer | TCTCCACCTCTACTG | P=O | 15mer | 118 |
| OH0284A-15mer | CCGGCATGGATCTCC | P=O | 15mer | 119 |
| OH0294A-15mer | GTTGAGACCGCCGGC | P=O | 15mer | 120 |
| OH0304A-15mer | ACGGCTCTAGGTTGA | P=O | 15mer | 121 |

TABLE 3-2

| oligonu-cleotide | sequence | modification | base length | sequence ID No. |
|---|---|---|---|---|
| OH0314A-15mer | CGCTTTAGAAACGGC | P=O | 15mer | 122 |
| OH0324A-15mer | CGCATCGACGCGCTT | P=O | 15mer | 123 |
| OH0334A-15mer | GGTCGGCGTCCGCAT | P=O | 15mer | 124 |
| OH0344A-15mer | TACTGCCGCGGGTCG | P=O | 15mer | 125 |
| OH0354A-15mer | CGTGTCAGCATACTG | P=O | 15mer | 126 |
| OH0364A-15mer | GAGCCTTGACCGTGT | P=O | 15mer | 127 |
| OH0374A-15mer | CGCACGCGGAGAGCC | P=O | 15mer | 128 |
| OH0384A-15mer | TGTGAGCCGCCGCAC | P=O | 15mer | 129 |
| OH0394A-15mer | CGGCTCCCACTGTGA | P=O | 15mer | 130 |
| OH0404A-15mer | GGAACCTGTGCGGCT | P=O | 15mer | 131 |
| OH0414A-15mer | TAGCTGAGCAGGAAC | P=O | 15mer | 132 |
| OH0424A-15mer | CGCCTACCAGTAGCT | P=O | 15mer | 133 |
| OH0434A-15mer | ACACGCAGGGCGCCT | P=O | 15mer | 134 |
| OH0444A-15mer | GTACGCTAGCACACG | P=O | 15mer | 135 |
| OH0454A-15mer | TGAGGCGGGAGTACG | P=O | 15mer | 136 |
| OH0464A-15mer | GTCAGTTCCTTGAGG | P=O | 15mer | 137 |
| OH0474A-15mer | GTCCTCGAGCGTCAG | P=O | 15mer | 138 |
| OH0484A-15mer | TTATCTTTAGGTCCT | P=O | 15mer | 139 |
| OH0494A-15mer | ATGGTGCCGGTTATC | P=O | 15mer | 140 |
| OH0504A-15mer | CAGCGGAGGCATGGT | P=O | 15mer | 141 |

TABLE 3-3

| oligonu-cleotide | sequence | modification | base length | sequence ID No. |
|---|---|---|---|---|
| OH0514A-15mer | CTTCCAGAGGCAGCG | P=O | 15mer | 142 |
| OH0524A-15mer | AGTCCTGTGGCTTCC | P=O | 15mer | 143 |
| OH0534A-15mer | GGAAAGTGCAAGTCC | P=O | 15mer | 144 |
| OH0544A-15mer | GGCGCAAGCTGGAAA | P=O | 15mer | 145 |
| OH0554A-15mer | ACGTTGCGTAGGCGC | P=O | 15mer | 146 |
| OH0564A-15mer | CGCCCACGACACGTT | P=O | 15mer | 147 |
| OH0574A-15mer | AACGCCCTGTCGCCC | P=O | 15mer | 148 |
| OH0584A-15mer | GCGAGCCAAGAACGC | P=O | 15mer | 149 |
| OH0594A-15mer | CTGCAGCTCGGCGAG | P=O | 15mer | 150 |
| OH0604A-15mer | TGAGCCACTGCTGCA | P=O | 15mer | 151 |
| OH0614A-15mer | AGGCCTGGCTTGAGC | P=O | 15mer | 152 |
| OH0624A-15mer | CAGTACCTTGAGGCC | P=O | 15mer | 153 |
| OH0634A-15mer | GGGCAATGCTCAGTA | P=O | 15mer | 154 |
| OH0644A-15mer | GAGTGTGCTTGGGCA | P=O | 15mer | 155 |
| OH0654A-15mer | AAAGGCAGGCGAGTG | P=O | 15mer | 156 |
| OH0664A-15mer | GTTCGTAGGAAAAGG | P=O | 15mer | 157 |
| OH0674A-15mer | GCGCGAACCTGTTCG | P=O | 15mer | 158 |
| OH0684A-15mer | GGCCGGGAAGGCGCG | P=O | 15mer | 159 |
| OH0694A-15mer | GGCTGGTAAGGGCCG | P=O | 15mer | 160 |
| OH0704A-15mer | GACAGGTCTAGGCTG | P=O | 15mer | 161 |

TABLE 3-4

| oligonu-cleotide | sequence | modification | base length | sequence ID No. |
|---|---|---|---|---|
| OH0714A-15mer | AGGATTGTCAGACAG | P=O | 15mer | 162 |
| OH0724A-15mer | CGCCCAGTCCAGGAT | P=O | 15mer | 163 |
| OH0734A-15mer | AGTCCGGGTTCGCCC | P=O | 15mer | 164 |
| OH0744A-15mer | AGCCGCCATCAGTCC | P=O | 15mer | 165 |
| OH0754A-15mer | GGGGACAGAGAGCCG | P=O | 15mer | 166 |
| OH0764A-15mer | GGGAACTTGTGGGGA | P=O | 15mer | 167 |
| OH0774A-15mer | CTGGATGGCCGGGAA | P=O | 15mer | 168 |
| OH0784A-15mer | GCGCTAGATTCTGGA | P=O | 15mer | 169 |
| OH0794A-15mer | GTGTTGCGCAGCGCT | P=O | 15mer | 170 |
| OH0804A-15mer | CTCCATTCCTGTGTT | P=O | 15mer | 171 |
| OH0814A-15mer | CTGTGGGCGTCTCCA | P=O | 15mer | 172 |
| OH0824A-15mer | GCGCACACGCCTGTG | P=O | 15mer | 173 |
| OH0834A-15mer | CGCCAGTGCGGCGCA | P=O | 15mer | 174 |
| OH0844A-15mer | CACCTGCCGCCGCCA | P=O | 15mer | 175 |
| OH0854A-15mer | TGGGGCTGCACACCT | P=O | 15mer | 176 |
| OH0564A-15mer | GTCTAGGCTGTGGGG | P=O | 15mer | 177 |
| OH0874A-15mer | TGTGGCTGAGGTCTA | P=O | 15mer | 178 |
| OH0884A-15mer | CGCAGCGAGTTGTGG | P=O | 15mer | 179 |
| OH0894A-15mer | TACGGTGGCGCGCAC | P=O | 15mer | 180 |
| OH0904A-15mer | CGCTAGGGTTTACGG | P=O | 15mer | 181 |
| OH0914A-15mer | CATCTCGGAGCGCTA | P=O | 15mer | 182 |
| OH0924A-15mer | GGACCACATGCATCT | P=O | 15mer | 183 |
| OH0934A-15mer | TCAGGGCGCTGGACC | P=O | 15mer | 181 |
| OH0944A-15mer | TTGAGGGAGTTCAGG | P=O | 15mer | 185 |
| OH0954A-15mer | GAACGACAGATTGAG | P=O | 15mer | 186 |

TABLE 3-5

| oligonu-cleotide | sequence | modification | base length | sequence ID No. |
|---|---|---|---|---|
| OH0964A-15mer | CCAGCCCAGCGAACG | P=O | 15mer | 187 |
| OH0974A-15mer | GGCACCTGTTCCAGC | P=O | 15mer | 188 |
| OH0984A-15mer | CAGTCCTTTAGGCAC | P=O | 15mer | 189 |
| OH0994A-15mer | GCTTGGCTGGCAGTC | P=O | 15mer | 190 |
| OH1004A-15mer | AGCACTCTGAGCTTG | P=O | 15mer | 191 |
| OH1014A-15mer | GCTGAGATCGAGCAC | P=O | 15mer | 192 |
| OH1024A-15mer | GTCTGTTGCAGCTGA | P=O | 15mer | 193 |
| OH1034A-15mer | GCCCTGTTCAGTCTG | P=O | 15mer | 194 |
| OH1054A-15mer | GCAGCTCGTCAGGCT | P=O | 15mer | 195 |
| OH1064A-15mer | TCCACCTCGGGCAGC | P=O | 15mer | 196 |
| OH1074A-15mer | TGTCAGGTTATCCAC | P=O | 15mer | 197 |
| OH1084A-15mer | TCCCGTCCAGTGTCA | P=O | 15mer | 198 |
| OH1094A-15mer | AGGAAGGGATTCCCG | P=O | 15mer | 199 |
| OH1104A-15mer | TCCAGGGACCAGGAA | P=O | 15mer | 200 |
| OH1114A-15mer | GGAGGGCAGTTCCAG | P=O | 15mer | 201 |
| OH1124A-15mer | CCCTCGTGGGGAGG | P=O | 15mer | 202 |
| OH1134A-15mer | GTTCATTGAGCCCTC | P=O | 15mer | 203 |
| OH1144A-15mer | CCACGCCGGAGTTCA | P=O | 15mer | 204 |
| OH1154A-15mer | CAGGCTGGGACCACG | P=O | 15mer | 205 |
| OH1164A-15mer | CGAACGTGCACAGGC | P=O | 15mer | 206 |
| OH1174A-15mer | CCGACAGGCTCGAAC | P=O | 15mer | 207 |

TABLE 3-5-continued

| oligonucleotide | sequence | modification | base length | sequence ID No. |
|---|---|---|---|---|
| OH1184A-15mer | GACACCCCCACCGAC | P=O | 15mer | 208 |
| OH1194A-15mer | CAGGGTTCCCGACAC | P=O | 15mer | 209 |
| OH1204A-15mer | GGAGCAGCACCAGGG | P=O | 15mer | 210 |

TABLE 3-6

| oligonucleotide | sequence | modification | base length | sequence ID NO. |
|---|---|---|---|---|
| OH1214A-15mer | CGGGCCCCTTGGAGC | P = O | 15mer | 211 |
| OH1224A-15mer | GGCAAAGCCCCGGGC | P = O | 15mer | 212 |
| OH1234A-15mer | TTGGATCTTAGGCAA | P = O | 15mer | 213 |
| OH1244A-15mer | TTATTCTGTCTTGGA | P = O | 15mer | 214 |
| OH1254A-15mer | AGTCCATTCATTATT | P = O | 15mer | 215 |
| OH1264A-15mer | AGGCAGTTTGAGTCC | P = O | 15mer | 216 |
| OH1274A-15mer | CCTGAAGCCAAGGCA | P = O | 15mer | 217 |
| OH1284A-15mer | ACGGGACTCCCCTGA | P = O | 15mer | 218 |
| OH1294A-15mer | CAACGTCCTGACGGG | P = O | 15mer | 219 |
| OH1304A-15mer | GAAAAGTCCTCAACG | P = O | 15mer | 220 |
| OH1314A-15mer | TGAATTGGTCGAAAA | P = O | 15mer | 221 |
| OH1324A-15mer | GGCAAAGGGTTGAAT | P = O | 15mer | 222 |
| OH1334A-15mer | ATAAAGGTGGGCAA | P = O | 15mer | 223 |

TABLE 4-1

| oligonucleotide | sequence ID No. | binding activity (score) |
|---|---|---|
| OH0083A-15mer | 101 | 0 |
| OH0102A-15mer | 85 | 1 |
| OH0104A-15mer | 102 | 2 |
| OH0114A-15mer | 103 | 1 |
| OH0134A-15mer | 104 | 0 |
| OH0144A-15mer | 105 | 0 |
| OH0154A-15mer | 106 | 0 |
| OH0164A-15mer | 107 | 0 |
| OH0174A-15mer | 108 | 0 |
| OH0184A-15mer | 109 | 2 |
| OH0194A-15mer | 110 | 0 |
| OH0204A-15mer | 111 | 0 |
| OH0214A-15mer | 112 | 0 |
| OH0224A-15mer | 113 | 0 |
| OH0234A-15mer | 114 | 0 |
| OH0244A-15mer | 115 | 0 |
| OH0254A-15mer | 116 | 0 |
| OH0264A-15mer | 117 | 0 |
| OH0274A-15mer | 118 | 0 |
| OH0284A-15mer | 119 | 1 |
| OH0294A-15mer | 120 | 0 |
| OH0304A-15mer | 121 | 0 |

TABLE 4-2

| oligonucleotide | sequence ID No. | binding activity (score) |
|---|---|---|
| OH0314A-15mer | 122 | 0 |
| OH0324A-15mer | 123 | 1 |
| OH0334A-15mer | 124 | 1 |
| OH0344A-15mer | 125 | 2 |
| OH0354A-15mer | 126 | 0 |
| OH0364A-15mer | 127 | 0 |
| OH0374A-15mer | 128 | 0 |
| OH0384A-15mer | 129 | 0 |
| OH0394A-15mer | 130 | 1 |
| OH0404A-15mer | 131 | 0 |
| OH0414A-15mer | 132 | 0 |
| OH0424A-15mer | 133 | 0 |
| OH0434A-15mer | 134 | 0 |
| OH0444A-15mer | 135 | 1 |
| OH0454A-15mer | 136 | 1 |
| OH0464A-15mer | 137 | 2 |
| OH0474A-15mer | 138 | 2 |
| OH0484A-15mer | 139 | 0 |
| OH0494A-15mer | 140 | 0 |
| OH0504A-15mer | 141 | 0 |

TABLE 4-3

| oligonucleotide | sequence ID No. | binding activity (score) |
|---|---|---|
| OH0514A-15mer | 142 | 0 |
| OH0524A-15mer | 143 | 0 |
| OH0534A-15mer | 144 | 1 |
| OH0544A-15mer | 145 | 0 |
| OH0554A-15mer | 146 | 0 |
| OH0564A-15mer | 147 | 0 |

TABLE 4-3-continued

| oligonucleotide | sequence ID No. | binding activity (score) |
|---|---|---|
| OH0574A-15mer | 148 | 0 |
| OH0584A-15mer | 149 | 0 |
| OH0594A-15mer | 150 | 0 |
| OH0604A-15mer | 151 | 0 |
| OH0614A-15mer | 152 | 0 |
| OH0624A-15mer | 153 | 0 |
| OH0634A-15mer | 154 | 0 |
| OH0644A-15mer | 155 | 1 |
| OH0654A-15mer | 156 | 1 |
| OH0664A-15mer | 157 | 0 |
| OH0674A-15mer | 158 | 0 |
| OH0684A-15mer | 159 | 1 |
| OH0694A-15mer | 160 | 1 |

TABLE 4-4

| oligonucleotide | sequence ID No. | binding activity (score) |
|---|---|---|
| OH0704A-15mer | 161 | 2 |
| OH0714A-15mer | 162 | 2 |
| OH0724A-15mer | 163 | 2 |
| OH0734A-15mer | 164 | 1 |
| OH0744A-15mer | 165 | 1 |
| OH0754A-15mer | 166 | 0 |
| OH0764A-15mer | 167 | 0 |
| OH0774A-15mer | 168 | 0 |
| OH0784A-15mer | 169 | 0 |
| OH0794A-15mer | 170 | 1 |
| OH0804A-15mer | 171 | 2 |
| OH0814A-15mer | 172 | 2 |
| OH0824A-15mer | 173 | 0 |
| OH0834A-15mer | 174 | 0 |
| OH0844A-15mer | 175 | 0 |
| OH0854A-15mer | 176 | 0 |
| OH0864A-15mer | 177 | 2 |
| OH0874A-15mer | 178 | 2 |
| OH0884A-15mer | 179 | 2 |
| OH0894A-15mer | 180 | 2 |
| OH0904A-15mer | 181 | 2 |

TABLE 4-5

| oligonucleotide | sequence ID No. | binding activity (score) |
|---|---|---|
| OH0914A-15mer | 182 | 0 |
| OH0924A-15mer | 183 | 1 |
| OH0934A-15mer | 184 | 0 |
| OH0944A-15mer | 185 | 1 |
| OH0954A-15mer | 186 | 0 |
| OH0964A-15mer | 187 | 0 |
| OH0974A-15mer | 188 | 1 |
| OH0984A-15mer | 189 | 0 |
| OH0994A-15mer | 190 | 1 |
| OH1004A-15mer | 191 | 1 |
| OH1014A-15mer | 192 | 1 |
| OH1024A-15mer | 193 | 2 |
| OH1034A-15mer | 194 | 2 |
| OH1054A-15mer | 195 | 0 |
| OH1064A-15mer | 196 | 2 |
| OH1074A-15mer | 197 | 2 |
| OH1084A-15mer | 198 | 1 |
| OH1094A-15mer | 199 | 1 |
| OH1104A-15mer | 200 | 0 |
| OH1114A-15mer | 201 | 0 |
| OH1124A-15mer | 202 | 0 |
| OH1134A-15mer | 203 | 0 |
| OH1144A-15mer | 204 | 0 |

TABLE 4-6

| oligonucleotide | sequence ID No. | binding activity (score) |
|---|---|---|
| OH1154A-15mer | 205 | 0 |
| OH1164A-15mer | 206 | 1 |
| OH1174A-15mer | 207 | 0 |
| OH1184A-15mer | 208 | 0 |
| OH1194A-15mer | 209 | 2 |
| OH1204A-15mer | 210 | 3 |
| OH1214A-15mer | 211 | 0 |
| OH1224A-15mer | 212 | 0 |
| OH1234A-15mer | 213 | 0 |
| OH1244A-15mer | 214 | 0 |
| OH1254A-15mer | 215 | 3 |
| OH1264A-15mer | 216 | 3 |
| OH1274A-15mer | 217 | 0 |
| OH1284A-15mer | 218 | 0 |
| OH1294A-15mer | 219 | 0 |
| OH1304A-15mer | 220 | 2 |
| OH1314A-15mer | 211 | 2 |
| OH1324A-15mer | 222 | 0 |
| OH1334A-15mer | 223 | 0 |

Of the antisense oligonucleotides which indicated the cleavage activity, the antisense oligonucleotides which were complementary to the neighbor region of the translation initiation site were OH0102A-15mer, OH0104A-15mer, and OH0114A-15mer, and the antisense oligonucleotides for the 3' non-coding region were OH1254A-15mer, OH1264A-15mer, OH1304A-15mer and OH1314A-15mer. These oligonucleotides are these having the sequences complementary to a part of active regions 2, 4 and 7, which were postulated to be effective in inhibiting the TNFα production according to the measurement results of inhibitory activity for human TNFα production in Examples 7 and 8. Accordingly, the results of RNaseH cleavage test were well consistent with the results of inhibitory activity in TNFα production.

EXAMPLE 14

Measurement of Inhibitory Activity for Human TNFα Production (Coding Region)

For each of the antisense oligonucleotide-binding regions that had been demonstrated in Example 13, typical antisense oligonucleotides for each region (see Table 5) were synthesized by the procedure of Example 3. The evaluation was conducted by the method described in Example 7. In other words, THP-1 cell was treated with SH0108A, SH0184A, SH0324A, SH0394A, SH0444A, SH0457A, SH0457A, SH0534A, SH0649A, SH0714A, SH0720A, SH0809A, SH0864A, SH0899A, SH1014A, SH1074A, SH1199A, SH1204A, SH1259A, SH1311A and the control oligonucleotide at the final concentration of 30 nM. After incubating for 4 hours, the culture supernatant was collected. TNFα in the culture supernatant was measured by human TNFα ELISA SYSTEM (manufactured by Amersham).

TABLE 5

| oligonucleotide | sequence | base length | modification | sequence No. |
|---|---|---|---|---|
| SH0108A | GACGCGCGCTCCATGGTCGA | 20mer | P = S | 27 |
| SH0184A | TTCATCGTCCAGCTCACAAG | 20mer | P = S | 225 |
| SH0324A | GCGTCCGCATCGACGCGCTT | 20mer | P = S | 226 |
| SH0394A | CTGTGCGGCTCCCACTGTGA | 20mer | P = S | 227 |
| SH0444A | CGGGAGTACGCTAGCACACG | 20mer | P = S | 228 |
| SH0457A | CAGTTCCTTGAGGCGGGAGT | 20mer | P = S | 229 |
| SH0470A | GGTCCTCGAGCGTCAGTTCC | 20mer | P = S | 230 |
| SH0534A | AAGCTGGAAAGTGCAAGTCC | 20mer | P = S | 231 |
| SH0649A | AAAGGCAGGCGAGTGTGCTT | 20mer | P = S | 232 |
| SH0714A | AGTCCAGGATTGTCAGACAG | 20mer | P = S | 233 |
| SH0720A | TCGCCCAGTCCAGGATTGTC | 20mer | P = S | 234 |
| SH0809A | CTGTGGGCGTCTCCATTCCT | 20mer | P = S | 235 |
| SH0864A | CTGAGGTCTAGGCTGTGGGG | 20mer | P = S | 236 |
| SH0899A | CGCTAGGGTTTACGGTGGCG | 20mer | P = S | 237 |
| SH1014A | TTGCAGCTGAGATCGAGCAC | 20mer | P = S | 238 |
| SH1074A | TCCAGTGTCAGGTTATCCAC | 20mer | P = S | 239 |
| SH1199A | GGAGCAGCACCAGGGTTCCC | 20mer | P = S | 240 |
| SH1204A | CCCTTGGAGCAGCACCAGGG | 20mer | P = S | 241 |
| SH1259A | AGGCAGTTTGAGTCCATTCA | 20mer | P = S | 41 |
| SH1311A | GTTGAATTGGTCGAAAAGTC | 20mer | P = S | 58 |

Figure 9:
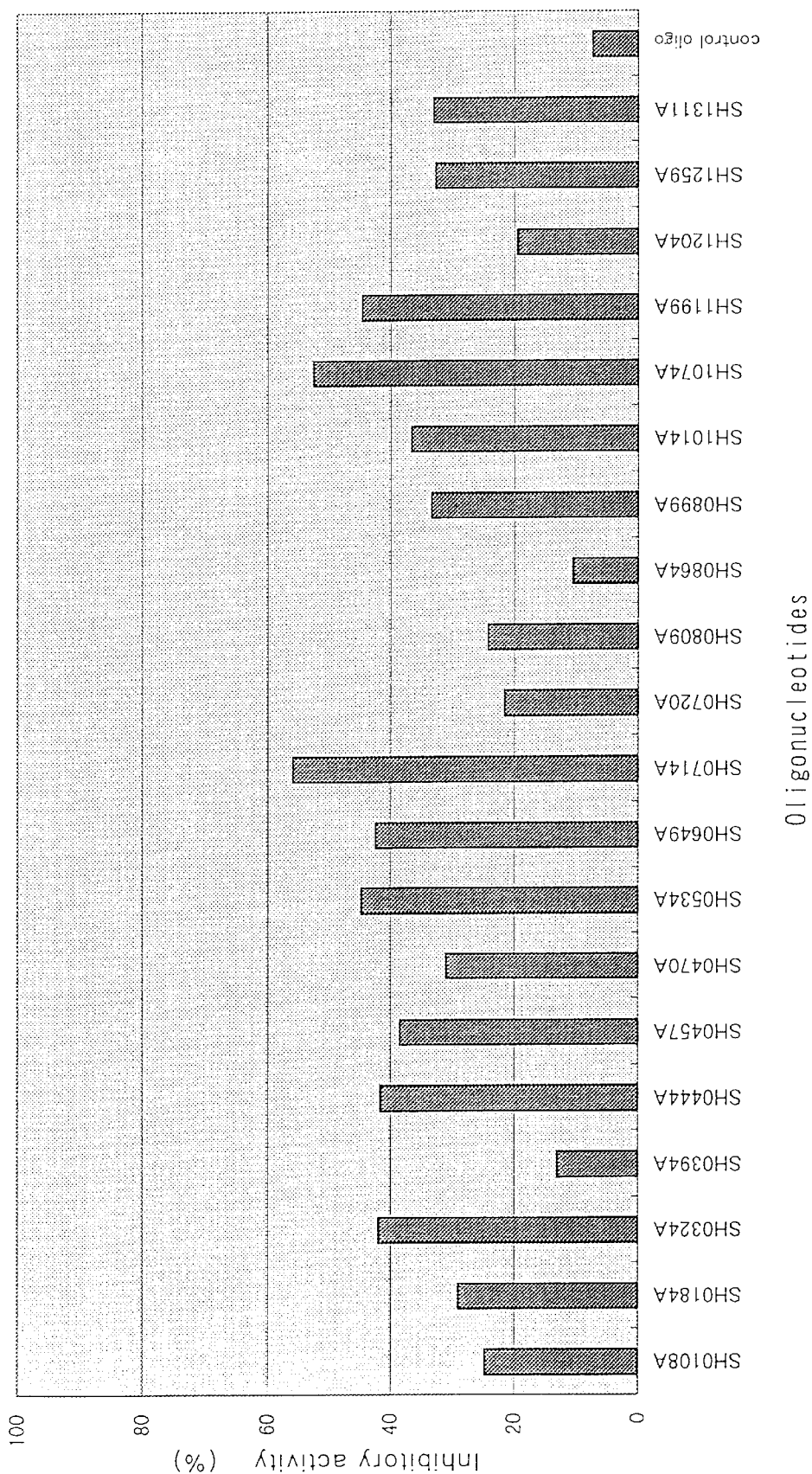
FIG. 9: A graph indicating inhibitory activity of the antisense oligonucleotides complementary to the coding region of mRNA encoding human CD14 to human TNFα production.

FIG. 9 indicates the results. The results confirmed the inhibitory activity for the twelve regions as described below. Active region 8 was indicated by oligonucleotide SH0184A which complementarily binds to a part of the sequence: CUUGUGAGCUGGACGA (SEQ ID NO:277).
Active region 9 was indicated by oligonucleotide SH0324A which complementarily binds to a part of the sequence AAGCGCGUCGAUGCGGACGCCGAC-CCGCGGCAGUA (SEQ ID NO: 278).
Active region 10 was indicated by oligonucleotide SH0394A which complementarily binds to a part of the sequence UCACAGUGGGAGCCG (SEQ ID NO: 279).
Active region 11 was indicated by oligonucleotides SH0444A, SH0457A and SH0470A which complementarily bind to a part of the sequence: CGUGUGC-UAGCGUACUCCGCGCUCAAG-GAACUGACGCUCGAGGAC (SEQ ID NO: 280).
Active region 12 was indicated by oligonucleotide SH0534A which complementarily binds to a part of the sequence GGACUUGCACUUUCC (SEQ ID NO: 281).
Active region 13 was indicated by oligonucleotide SH0649A which complementarily binds to a part of the sequence: UACUGACCAUUGCCCAACCACACUCGC-CUGCCUUU (SEQ ID NO: 282).
Active region 14 was indicated by oligonucleotides SH0714A and SH0720A which complementarily bind to a part of the sequence CGCGCCUUCCCGGCCCUUAC-CAGCCUAGACCUGUCUGACAAUCCUG-GACUGGGCGA ACGCGGACUGAUGGCGGCU (SEQ ID NO: 283).

Active region 15 was indicated by oligonucleotide SH0809A which complementarily binds to a part of the sequence CCAGAAUCUAGCGCUGCGCAACACAG-GAAUGGAGACGCCCACAG (SEQ ID NO: 284).
Active region 16 was indicated by oligonucleotide SH0899A which complementarily binds to a part of the sequence CCCCACAGCCUAGACCUCAGCCA-CAACUCGCUGCGCGCCACCGUAAACCCUAGCG (SEQ ID NO: 285).
Active region 17 was indicated by oligonucleotide SH1014A which complementarily binds to a part of the sequence GACUGCCAGCCAAGCUCAGAGUGCUC-GAUCCAGCUGCAACAGACUGAACAGC (SEQ ID NO: 286).
Active region 18 was indicated by oligonucleotide SH1074A which complementarily binds to a part of the sequence GCUGCCCGAGGUGGAUAACCUGACACUG-GACGGGAAUCCCUUCCU (SEQ ID NO: 287).
Active region 19 was indicated by oligonucleotides SH1199A and SH1204A which complementarily bind to a part of the sequence GUGUGGGGAACCCUG-GUGCUGCUCC SEQ ID NO.

EXAMPLE 15

Designing of Consensus Oligonucleotides, and Measurement of the Inhibitory Activities for the CD14 Expression (1) Designing of Consensus Oligonucleotides
Oligonucleotides, which binds to both the gene encoding the human CD14 and the gene encoding the CD14 of non-human animals, (hereinafter called "consensus oligonucleotide") were prepared by the procedure as described below. First, by paying attention to the region of SEQ ID No. 1 from 93th guanine to 145th uridine, which was the suspected effective binding region, the sequences was compared between the human and the mouse sequence. When 5 types of 21mer antisense oligonucleotides complementary to the sequence from 103th uridine to 137th uridine which exhibited a high activity in Examples 8 and 12 were designed, all of the mismatch bases between the human and the mouse sequences (bases indicated as X in FIG. 10) were the bases wherein cytosine or uridine was substituted with pyrimidine. In view of such situation, antisense oligonucleotides wherein the bases indicated by X were substituted with inosine which is a base binding to a pyrimidine base was designed, and synthesized in the procedure described in Example 3. Table 6 shows the synthesized consensus oligonucleotides.

Next, inhibitory activities of SU0104A-21mer, SU0105A-21mer, SU0106A-21mer and SU0108A-21mer for mouse TNFα production were measured. The measurement was performed in accordance with the procedure of Example 9 using RAW264.7 cell instead of the J774A.1 cell. TNFα in the culture supernatant was measured by mouse TNFα ELISA SYSTEM (manufactured by Amersham). FIG. 11 indicates the results.

Inhibitory activity of the SU0104A-21mer, SU0105A-21mer, SU0106A-21mer and SU0108A-21mer for the mouse TNFα production was 24%, 33%, 54% and 69%, respectively. Control oligonucleotide exhibited the inhibition of 3%. The results demonstrate that the oligonucleotides SU0104A-21mer, SU0105A-21mer, SU0106A-21mer and SU0108A-21mer are those acting on both the mouse and the human.

TABLE 6

| oligonucleotide | sequence | base length | modification | SEQ. ID. No. |
|---|---|---|---|---|
| SU0103A-21mer | CICGCTCCATGGTCGITAIIT | 21mer | P = S | 242 |
| SU0104A-21mer | ICICGCTCCATGGTCGITAII | 21mer | P = S | 243 |
| SU0105A-21mer | CICICGCTCCATGGTCGITAI | 21mer | P = S | 244 |
| SU0106A-21mer | ICICICGCTCCATGGTCGITA | 21mer | P = S | 245 |
| SU0107A-21mer | IICICICGCTCCATGGTCGIT | 21mer | P = S | 246 |
| SU0108A-21mer | IIICICICGCTCCATGGTCGI | 21mer | P = S | 247 |
| SU0109A-21mer | IIIICICICGCTCCATGGTCG | 21mer | P = S | 248 |
| SU0110A-21mer | CIIIICICICGCTCCATGGTC | 21mer | P = S | 249 |
| SU0111A-21mer | GCIIIICICICGCTCCATGGT | 21mer | P = S | 250 |
| SU0112A-21mer | AGCIIIICICICGCTCCATGG | 21mer | P = S | 251 |
| SU0113A-21mer | AAGCIIIICICICGCTCCATG | 21mer | P = S | 252 |
| SU0114A-21mer | CAAGCIIIICICICGCTCCAT | 21mer | P = S | 253 |
| SU0115A-21mer | ACAAGCIIIICICICGCTCCA | 21mer | P = S | 254 |
| SU0116A-21mer | AACAAGCIIIICICICGCTCC | 21mer | P = S | 255 |
| SU0117A-21mer | CAACAAGCIIIICICICGCTC | 21mer | P = S | 256 |
| SU0118A-21mer | GCAACAAGCIIIICICICGCT | 21mer | P = S | 257 |

(2) Measurement of Inhibitory Activities of Consensus Oligonucleotides for Expression of Human CD14/Luciferase Fusion Protein and Production of Mouse TNFα

Inhibitory Activity of the following oligonucleotides: SU103A-21mer, SU0104A-21mer, SU0105A-21mer, SU0106A-21mer, SU0107A-21mer, SU0108A-21mer, SU0109A-21mer, SU0110A-21mer, SU0111A-21mer, SU0112A-21mer, SU0113A-21mer, SU0114A-21mer, SU0115A-21mer, SU0116A-21mer, SU0117-21mer and SU0118A-21mer for inhibiting the expression of the CD14/luciferase fusion protein was compared between the oligonucleotides using HeLa transformant expressing the human CD14/luciferase fusion protein described in Example 12. FIG. 10 indicates the results. Consensus oligonucleotides exhibiting at least 40% of the inhibitory activity were SU0103A-21mer, SU0104A-21mer, SU0105A-21mer, SU0106A-21mer, SU0107A-21mer, SU0108A-21mer, and SU0109A-21mer.

INDUSTRIAL UTILITY

The present invention provides oligonucleotides comprising the sequence which hybridizes with a part of the gene encoding the human CD14. The present invention also provides pharmaceutical compositions comprising such oligonucleotide and a pharmacologically acceptable carrier. Effective suppression of the inflammatory factor is thereby realized. In other words, the oligonucleotide which inhibits the human CD14 expression is useful as a prophylactic/therapeutic agent for various disorders caused by the inflammatory factor induced by the mediation of CD14 such as systemic inflammatory response syndrome, endotoxemia and endotoxic shock, ulcerative colitis, Crohn's disease, autoimmune response, allergy disease, cancer, graft-versus-host reaction, peritonitis, or osteoporosis.

What is claimed is:

1. An antisense oligonucleotide having a nucleotide number of 10–55 residues which specifically hybridizes with a transcript encoding human CD14, and which inhibits expression of CD14.

2. The oligonucleotide according to claim 1, comprising a sequence complementary to a transcript encoding human CD14.

3. The oligonucleotide according to claim 1, wherein the oligonucleotide comprises at least a sequence which is complementary to a sequence selected from the group consisting of a 5' non-coding region, translation initiation region, coding region and 3' non-coding region of a mRNA encoding human CD14.

4. The oligonucleotide according to claim 1, wherein the oligonucleotide comprises a nucleotide sequence, which specifically hybridizes with or is complementary to any one of nucleotide sequences selected from the group consisting of following (1)–(19):

(1) positions 23 to 62 of nucleotide sequence SEQ ID NO:1,
(2) positions 93 to 131 of nucleotide sequence SEQ ID NO:1,
(3) positions 117 to 145 of nucleotide sequence SEQ ID NO:1,
(4) positions 1241 to 1280 of nucleotide sequence SEQ ID NO:1,
(5) positions 1264 to 1285 of nucleotide sequence SEQ ID NO:1,
(6) positions 1267 to 1320 of nucleotide sequence SEQ ID NO:1,
(7) positions 1301 to 1350 of nucleotide sequence SEQ ID NO:1,
(8) positions 184 to 203 of nucleotide sequence SEQ ID NO:1,
(9) positions 324 to 343 of nucleotide sequence SEQ ID NO:1,
(10) positions 394 to 413 of nucleotide sequence SEQ ID NO:1,
(11) positions 444 to 489 of nucleotide sequence SEQ ID NO:1,
(12) positions 534 to 553 of nucleotide sequence SEQ ID NO:1,
(13) positions 644 to 668 of nucleotide sequence SEQ ID NO:1,
(14) positions 684 to 828 of nucleotide sequence SEQ ID NO:1,
(15) positions 794 to 828 of nucleotide sequence SEQ ID NO:1,
(16) positions 864 to 918 of nucleotide sequence SEQ ID NO:1,
(17) positions 994 to 1048 of nucleotide sequence SEQ ID NO:1,

(18) positions 1064 to 1108 of nucleotide sequence SEQ ID NO:1,
(19) positions 1194 to 1223 of nucleotide sequence SEQ ID NO:1.

5. The oligonucleotide according to claim 1, wherein the oligonucleotide comprises a nucleotide sequence complementary to any one of nucleotide sequences selected from the group consisting of the following (1)–(19):
(1) positions 23 to 62 of nucleotide sequence SEQ ID NO:1,
(2) positions 93 to 131 of nucleotide sequence SEQ ID NO:1,
(3) positions 117 to 145 of nucleotide sequence SEQ ID NO:1,
(4) positions 1241 to 1280 of nucleotide sequence SEQ ID NO:1,
(5) positions 1264 to 1285 of nucleotide sequence SEQ ID NO:1,
(6) positions 1267 to 1320 of nucleotide sequence SEQ ID NO:1,
(7) positions 1301 to 1350 of nucleotide sequence SEQ ID NO:1,
(8) positions 184 to 203 of nucleotide sequence SEQ ID NO:1,
(9) positions 324 to 343 of nucleotide sequence SEQ ID NO:1,
(10) positions 394 to 413 of nucleotide sequence SEQ ID NO:1,
(11) positions 444 to 489 of nucleotide sequence SEQ ID NO:1,
(12) positions 534 to 553 of nucleotide sequence SEQ ID NO:1,
(13) positions 644 to 668 of nucleotide sequence SEQ ID NO:1,
(14) positions 684 to 828 of nucleotide sequence SEQ ID NO:1,
(15) positions 794 to 828 of nucleotide sequence SEQ ID NO:1,
(16) positions 864 to 918 of nucleotide sequence SEQ ID NO:1,
(17) positions 994 to 1048 of nucleotide sequence SEQ ID NO:1,
(18) positions 1064 to 1108 of nucleotide sequence SEQ ID NO:1,
(19) positions 1194 to 1223 of nucleotide sequence SEQ ID NO:1.

6. The oligonucleotide according to claim 4, wherein the oligonucleotide specifically hybridizes with any one of nucleotide sequences selected from the group consisting of (1), (2), (4), (5), (7), (8), (11), (16) and (19) among the nucleotide sequences according to claim 4.

7. The oligonucleotide according to claim 5, wherein the oligonucleotide has a nucleotide sequence complementary to any one of nucleotide sequences selected from the group consisting of (1), (2), (4), (5), (7), (8), (11), (16) and (19) among the nucleotide sequences according to claim 5.

8. The oligonucleotide according to claim 1, wherein the oligonucleotide suppresses the expression of human CD14 in a host cell in vitro.

9. The oligonucleotide according to claim 8, wherein the oligonucleotide suppresses the expression of human CD14 by at least 30% in a translation inhibition experiment.

10. The oligonucleotide according to claim 8, wherein the oligonucleotide exhibits a binding ability score of at least 1 with a mRNA encoding human CD14 in an RNase H cleavage experiment.

11. The oligonucleotide according to claim 5, wherein said oligonucleotide has a nucleotide number of 10 to 50 residues.

12. The oligonucleotide according to claim 11, wherein said oligonucleotide has a nucleotide number of 15 to 30 residues.

13. The oligonucleotide according to claim 1, wherein at least one linkage between nucleotides contains a sulfur atom.

14. An oligonucleotide which comprises a nucleotide sequence selected from the group consisting of SEQ ID NOS. 10, 11, 12, 13, 16, 19, 20, 21, 22, 23, 24, 25, 26, 27, 28, 29, 32, 33, 34, 34, 35, 37, 39, 40, 41, 42, 45, 46, 47, 48, 49, 50, 51, 52, 53, 54, 55, 56, 57, 58, 59, 61, 62, 63, 64, 70, 71, 72, 76, 74, 75, 76, 77, 78, 79, 81, 83, 85, 86, 87, 88, 89, 90, 102, 103, 109, 123, 124, 125, 130, 135, 136, 137, 138, 144, 155, 156, 159, 160, 161, 162, 163, 164, 165, 170, 171, 172, 177, 178, 179, 180, 181, 190, 191, 192, 193, 194, 196, 197, 198, 199, 209, 210, 215, 216, 220, 221, 224, 225, 226, 227, 228, 229, 230, 231, 232, 233, 234, 235, 236, 237, 238, 239, 240, 241, 242, 243, 244, 245, 246, 247 and 248.

15. An antisense oligonucleotide having a nucleotide number of 10–55 residues which specifically hybridizes with a transcript encoding CD14 of mouse or simian.

16. A pharmaceutical composition comprising an oligonucleotide according to claim 1, and a pharmacologically acceptable carrier.

17. A method for inhibiting inflammation induced through human CD14, by administering physiologically acceptable amount of a pharmaceutical composition according to claim 16 to a patient in need thereof.

18. A method for treating sepsis or endotoxemia, or septic shock or endotoxin shock, by administering physiologically acceptable amount of a pharmaceutical composition according to claim 16 to a patient in need thereof.

19. A method for treating sepsis or endotoxemia, or septic shock or endotoxin shock, which comprises administering to a patient in need thereof an oligonucleotide which specifically hybridizes to a transcript encoding human CD14 and suppresses the expression of the human CD14, as its effective ingredient, and a pharmacologically acceptable carrier.

20. The oligonucleotide according to claim 1, wherein said oligonucleotide has a nucleotide number of 10 to 50 residues.

* * * * *